(12) United States Patent
Sheehan et al.

(10) Patent No.: US 9,221,835 B2
(45) Date of Patent: Dec. 29, 2015

(54) SPIROCYCLIC DERIVATIVES AS ANTIPARASITIC AGENTS

(71) Applicant: Zoetis Services LLC, Florham Park, NJ (US)

(72) Inventors: Susan M. K. Sheehan, Kalamazoo, MI (US); Valerie A. Vaillancourt, Kalamazoo, MI (US)

(73) Assignee: Zoetis Services LLC, Florham Park, NJ (US)

( * ) Notice: Subject to any disclaimer, the term of this patent is extended or adjusted under 35 U.S.C. 154(b) by 0 days.

(21) Appl. No.: 14/423,919

(22) PCT Filed: Sep. 4, 2013

(86) PCT No.: PCT/US2013/057940
§ 371 (c)(1),
(2) Date: Feb. 25, 2015

(87) PCT Pub. No.: WO2014/039489
PCT Pub. Date: Mar. 13, 2014

(65) Prior Publication Data
US 2015/0210710 A1    Jul. 30, 2015

Related U.S. Application Data

(60) Provisional application No. 61/698,380, filed on Sep. 7, 2012, provisional application No. 61/699,017, filed on Sep. 10, 2012.

(51) Int. Cl.
*C07D 491/107*    (2006.01)

(52) U.S. Cl.
CPC .................................. *C07D 491/107* (2013.01)

(58) Field of Classification Search
CPC ................................................... C07D 491/107
See application file for complete search history.

(56) References Cited

FOREIGN PATENT DOCUMENTS

| WO | 2010/084067 | | 7/2010 |
|---|---|---|---|
| WO | 2012/017359 | | 2/2012 |
| WO | WO 2012017359 A1 | * | 2/2012 |
| WO | 2012/120399 | | 9/2012 |
| WO | WO 2012120399 A1 | * | 9/2012 |
| WO | WO 2013116230 A1 | * | 8/2013 |
| WO | WO 2014036056 A1 | * | 3/2014 |
| WO | WO 2014039422 A1 | * | 3/2014 |
| WO | WO 2014039475 A1 | * | 3/2014 |
| WO | WO 2014039484 A1 | * | 3/2014 |
| WO | WO 2014081800 A1 | * | 5/2014 |
| WO | WO 2014189837 A1 | * | 11/2014 |

OTHER PUBLICATIONS

Wermuth, C.G. "Molecular Variations Based on Isosteric Replacements" in "The Practice of Medicinal Chemistry" 1996, Academic Press Limited, pp. 203-237.*

Patani et al. Chem. Rev. 1996, 96, 3147-3176.*
PCT International Search Report, PCT/US2013/057940 filed Sep. 4, 2013 (3 pages).

* cited by examiner

*Primary Examiner* — Matthew Coughlin
(74) *Attorney, Agent, or Firm* — Paul M. Misiak; Barbara L. Renda

(57) ABSTRACT

The invention recites spirocyclic derivatives of Formula (V.1) or (V.2), stereoisomers thereof, veterinary acceptable salts thereof, compositions thereof, processes for making, and their use as a parasiticide for an animal. The variables A, B, V, Z, Y, $W^1$, $W^2$, $W^3$, $R^{1a}$, $R^{1b}$, $R^{1c}$, $R^2$, $R^3$, $R^4$, n, and "- - -" are as described herein.

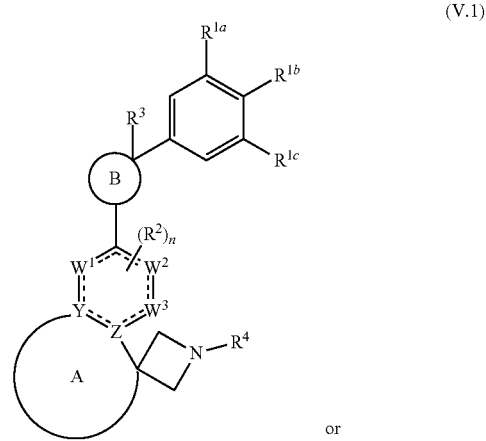

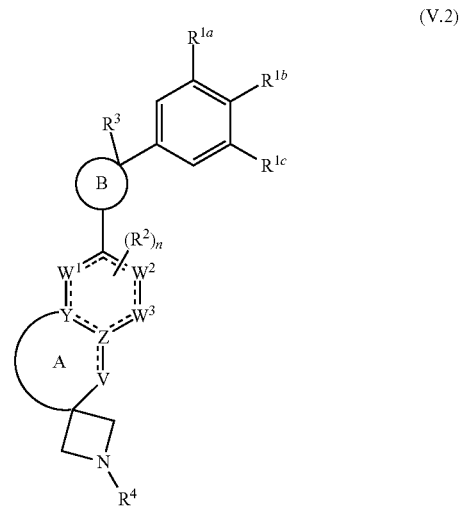

17 Claims, No Drawings

SPIROCYCLIC DERIVATIVES AS ANTIPARASITIC AGENTS

CROSS-REFERENCE TO RELATED APPLICATIONS

This application is a 371 filing of International Application No. PCT/US2013/057940 filed Sep. 4, 2013, which claims the benefit of U.S. Provisional Application 61/698,380 filed Sep. 7, 2012; and U.S. Provisional Application 61/699,017 filed Sep. 10, 2012.

FIELD OF THE INVENTION

This invention relates to spirocyclic derivatives having parasiticidal activity. The compounds of interest are spirocyclic derivatives with a saturated or partially saturated heterocyclic moiety containing nitrogen and/or oxygen heteroatoms. The invention also relates to processes of making said spirocyclic derivatives, compositions, and methods of use thereof.

BACKGROUND

There is a need for improved antiparasitics for use with animals, and in particular there is a need for improved insecticides and acaricides. Furthermore there is a need for improved topical and oral products with convenient administration and which contain one or more of such antiparasitics which can be used to effectively treat against parasites. Such products would be particularly useful for the treatment of animals including: birds (e.g., chickens and turkeys), fish, companion animals (e.g., cats, dogs, llamas, and horses), and livestock (e.g., cattle, bison, swine, sheep, deer, elk, and goats).

The compounds currently available for insecticidal and acaricidal treatment of animals do not always demonstrate good activity, good speed of action, or a long duration of action. Most treatments contain hazardous chemicals that can have serious consequences, including neurotoxicity and lethality from accidental ingestion. Persons applying these agents are generally advised to limit their exposure. Pet collars and tags have been utilized to overcome some problems, but these are susceptible to chewing, ingestion, and subsequent toxicological affects to the animal. Thus, current treatments achieve varying degrees of success which depend partly on toxicity, method of administration, and efficacy. Currently, some agents are actually becoming ineffective due to parasitic resistance.

Isoxazoline derivatives have been disclosed in the art as having insecticidal and acaricidal activity. For example, WO2007/105814, WO2008/122375, and WO2009/035004 recite certain alkylene linked amides. WO2010/032437 discloses that the benzyl amide can be moved to the position ortho to the isoxazoline. Further, WO2007/075459 discloses phenyl isoxazolines substituted with 5- to 6-membered heterocycles, and WO2010/084067 and WO2010/025998 disclose phenyl isoxazolines substituted with 10- to 11-membered fused aryl and heteroaryls. Chiral processes for manufacturing isoxazolines have been reported in WO2011/104089 and WO2009/063910. Isoxazoline azetidine derivatives were published in WO2012/017359. Some spiro-azetidine isobenzofuran derivatives for the treatment of diabetes and hyperlipidemia were described in WO2008/096746. In addition, spirocyclic isoxazolines were recently published in WO2012/120399. However, none of these citations exemplify non-isoxazoline spirocyclic molecules, or processes of manufacturing the spirocyclic compounds, nor does the prior art indicate that such compounds would be useful against a spectrum of parasitic species relevant to companion animals, livestock, birds, or fish against the range of parasitic morphological lifecycle stages.

Despite the availability of effective, broad spectrum antiparasitic, there remains a need for a safer, convenient, efficacious, and environmentally friendly product that will overcome the ever-present threat of resistance development.

The present invention overcomes one or more of the various disadvantages of, or improves upon, the properties of existing compounds. In particular the present invention develops new non-isoxazoline spirocyclic derivatives which demonstrate such properties.

SUMMARY

The present invention provides Formula (V.1) and Formula (V.2) compounds, stereoisomers thereof, veterinary acceptable salts thereof, which act as parasiticides, in particular, ectoparasiticides; therefore may be used to prevent, treat, repel, and control acarids and insect infection and infestation in animals. In addition, the invention contemplates the control and prevention of tick borne diseases, for example, Lyme disease, canine and bovine anaplasmosis, canine ehrlichiosis, canine rickettsiosis, canine and bovine babesiosis, epizootic bovine abortion, leishmaniasis, and theileriosis. Thus, according to the invention, there is provided a compound of Formula (V.1) and Formula (V.2)

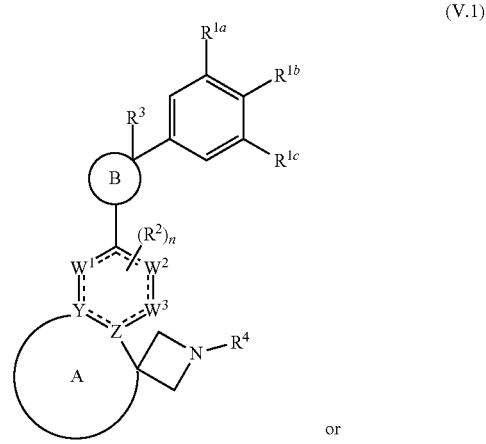

or (V.2)

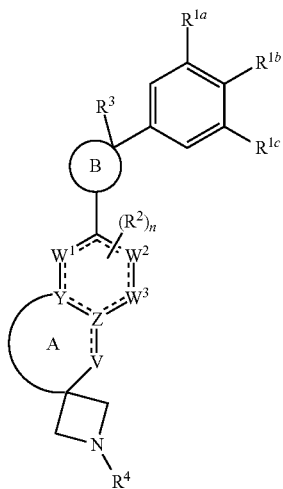

wherein
Y and Z are each independently C or N;
$W^1$, $W^2$, and $W^3$ are each independently C or N;
V is C, N, O, or S;

A taken together with Y and Z or Y, Z, and V is a 5- to 7-membered partially saturated or saturated carbocyclic or heterocyclic ring where the heterocyclic ring contains at least 1 to 3 heteroatoms selected from N, O, or S, and where ring A is optionally substituted with at least one substituent selected from oxo, =S, =$NR^7$, halo, hydroxyl, cyano, $C_1$-$C_6$alkyl, $C_1$-$C_6$haloalkyl, and $C_1$-$C_6$alkoxy;

B is

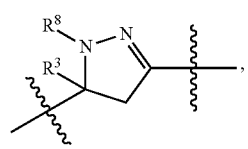 B1

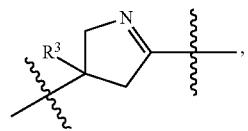 B2

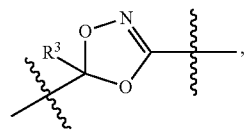 B3

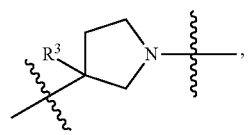 B4

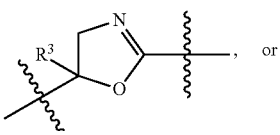 B5, or

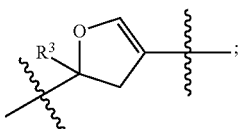 B6 wherein "⁓" represents the point of attachment;

$R^{1a}$, $R^{1b}$, and $R^{1c}$ are each independently hydrogen, halo, cyano, hydroxyl, nitro, $C_1$-$C_6$alkyl, $C_1$-$C_6$haloalkyl, $C_1$-$C_6$alkoxy, $C_0$-$C_3$alkyl$C_3$-$C_6$cycloalkyl, $C_1$-$C_6$haloalkoxy, —C(O)$NH_2$, —$SF_5$, or —S(O)$_p$R;

$R^2$ is halo, cyano, $C_1$-$C_6$alkyl, $C_1$-$C_6$haloalkyl, nitro, hydroxyl, —C(O)$NR^aR^b$, $C_2$-$C_6$alkenyl, $C_2$-$C_6$alkynyl, —S(O)$_p$R, or —OR;

$R^3$ is cyano, $C_1$-$C_6$alkyl, $C_1$-$C_6$haloalkyl, —C(O)$NR^aR^b$, $C_2$-$C_6$alkenyl, $C_2$-$C_6$alkynyl, $C_2$-$C_6$haloalkenyl, or $C_2$-$C_6$haloalkynyl;

$R^4$ is hydrogen, $C_1$-$C_6$alkyl, $C_0$-$C_6$alkyl$C_3$-$C_6$cycloalkyl, —C(O)$R^5$, —C(S)$R^5$, —C(O)$NR^aR^5$, —C(O)C(O)$NR^aR^5$, —S(O)$_p$$R^c$, —S(O)$_2$$NR^aR^5$, —C($NR^7$)$R^5$, —C($NR^7$)$NR^aR^5$, $C_0$-$C_6$alkylphenyl, $C_0$-$C_6$alkylheteroaryl, or $C_0$-$C_6$alkylheterocycle;

$R^5$ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;

$R^7$ is hydrogen, $C_1$-$C_6$alkyl, hydroxyl, cyano, nitro, —S(O)$_p$$R^c$, or $C_1$-$C_6$alkoxy;

$R^8$ is hydrogen, $C_1$-$C_6$alkyl, hydroxyl, cyano, —S(O)$_p$$R^c$, or $C_1$-$C_6$alkoxy;

R is $C_1$-$C_6$alkyl or $C_3$-$C_6$cycloalkyl optionally substituted with at least one halo substituent;

$R^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

$R^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$$NR^aR^b$, —$NR^aR^b$, —$NR^aC(O)R^b$, —SC(O)R, —SCN, or —C(O)$NR^aR^b$;

each of $R^4$ and $R^5$ $C_1$-$C_6$alkyl or $C_0$-$C_6$alkyl$C_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxyl$C_1$-$C_6$alkyl-, —S(O)$_p$$R^c$, —SH, —S(O)$_p$$NR^aR^b$, —$NR^aR^b$, —$NR^aC(O)R^b$, —SC(O)R, —SCN, or —C(O)$NR^aR^b$; and wherein each of $R^4$ and $R^5$ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =$NR^7$, hydroxyl, $C_1$-$C_6$alkoxy, $C_1$-$C_6$alkyl, hydroxyl$C_1$-$C_6$alkyl-, $C_1$-$C_6$haloalkyl, —SH, —S(O)$_p$R, and $C_1$-$C_6$haloalkoxy;

n is the integer 0, 1, or 2, and when n is 2, each $R^2$ may be identical or different from each other;

p is the integer 0, 1, or 2; and

---- is a single or double bond;

stereoisomers thereof, and veterinary acceptable salts thereof.

In another aspect of the invention are spirocyclic derivatives of Formula (V.1), stereoisomers, and veterinary acceptable salts thereof.

In another aspect of the invention are spirocyclic derivatives of Formula (V.2), stereoisomers, and veterinary acceptable salts thereof.

In another aspect of the invention are spirocyclic dihydrofuranyl compounds of Formula (V.1) that are Formula (V.1.1) compounds

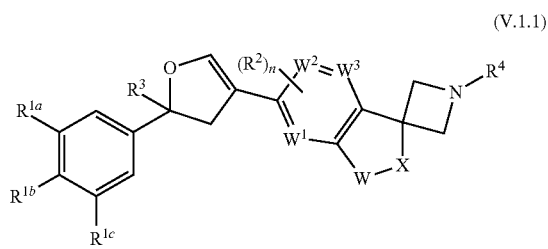

(V.1.1)

wherein $R^{1a}$, $R^{1b}$, $R^{1c}$, $W^1$, $W^2$, $W^3$, $R^2$, $R^3$, $R^4$, and n are as defined above; X and W are each independently —O—, —S(O)$_p$—, —NR$^6$—, —CH$_2$—, —C(O)—, —C(NR$^7$)—, or —C(S)—; when X is —O—, —S(O)$_p$—, or —NR$^6$—, then W is —CH$_2$—, —C(O)—, —C(NR$^7$)—, or —C(S)—; and when W is —O—, —S(O)$_p$—, or —NR$^6$—, then X is —CH$_2$—, —C(O)—, —C(NR$^7$)—, or —C(S)—; wherein R$^6$ is hydrogen, C$_1$-C$_6$alkyl, hydroxyl, or C$_1$-C$_6$alkoxy; and wherein R$^7$ and p are as defined herein, stereoisomers thereof, and veterinary acceptable salts thereof.

In another aspect of the invention are compounds of Formula (V.1.1), $W^1$, $W^2$, and $W^3$ are each C. In yet another aspect of the invention, W$^1$ is N and W$^2$ and W$^3$ are each C, or W$^2$ is N and W$^1$ and W$^3$ are each C, or W$^3$ is N and W$^1$ and W$^2$ are each C. In yet another aspect, W$^1$ and W$^2$ are each N and W$^3$ is C. In yet another aspect, W$^1$ and W$^3$ are each N and W$^2$ is C. In yet another aspect, W$^2$ and W$^3$ are each N and W$^1$ is C. In each case, X is O and W is —C(O)— or CH$_2$—; or W is O and X is —C(O)— or —CH$_2$—; or X is —NR$^6$— and W is —CH$_2$— or —C(O)—; or W is —NR$^6$— and X is —CH$_2$— or —C(O)—; or X is S(O)$_p$ and W is —CH$_2$— or —C(O)—; or W is S(O)$_p$ and X is —CH$_2$— or —C(O)—, wherein p and R$^6$ are as defined herein, stereoisomers thereof, and veterinary acceptable salts thereof.

In another aspect of the invention of Formula (V.1.1), are spirocyclic dihydrofuranyl compounds of Formula (1.1), (1.2), (1.3), (1.4), (1.5), (1.6), (1.7), and (1.8)

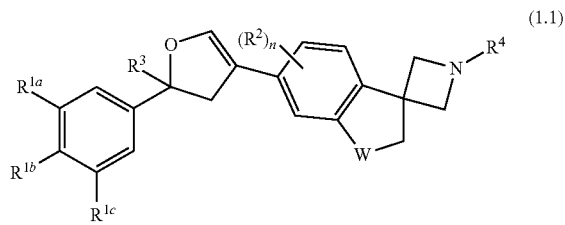

(1.1)

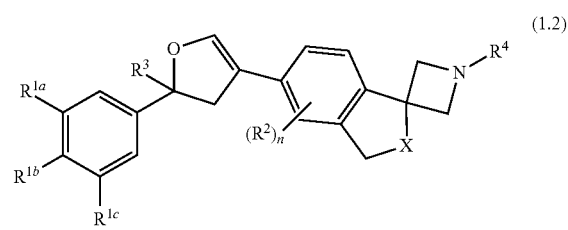

(1.2)

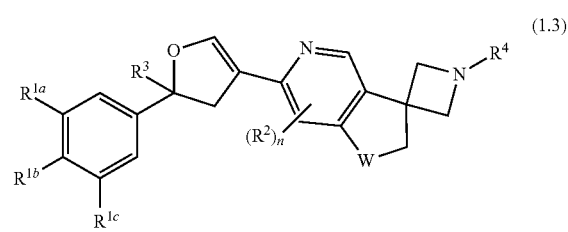

(1.3)

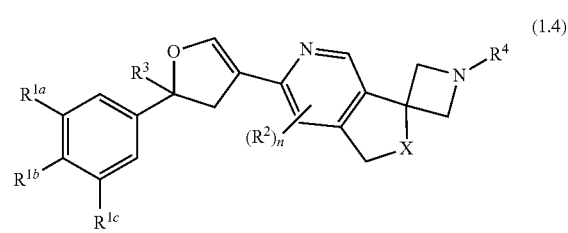

(1.4)

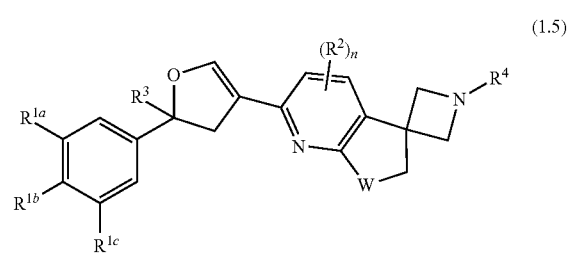

(1.5)

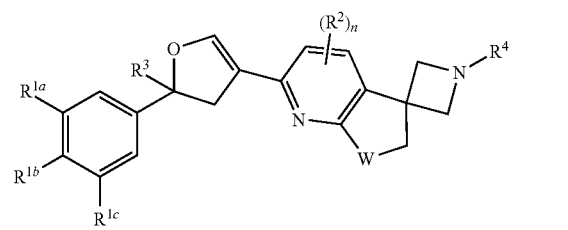

(1.6)

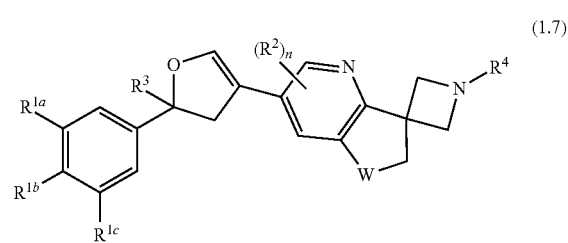

(1.7)

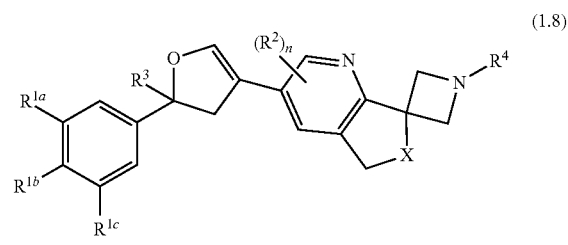

(1.8)

wherein $R^{1a}$, $R^{1b}$, $R^{1c}$, $R^2$, $R^3$, $R^4$, and n are as defined above, and W and X are each O or —$S(O)_p$—, wherein p is as defined above, stereoisomers thereof, and veterinary acceptable salts thereof.

In another aspect of the invention of Formula (1.2), are spirocyclic dihydrofuranyl compounds of Formula (1.2A)

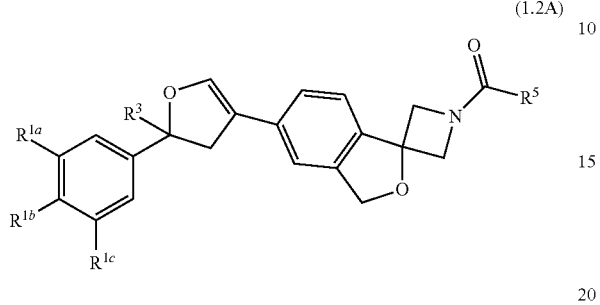
(1.2A)

wherein $R^{1a}$, $R^{1b}$, $R^{1c}$, $R^3$, and $R^5$, are as defined herein, stereoisomers thereof, and veterinary acceptable salts thereof.

In another aspect of the invention are compounds of Formula (V.1) that are spirocyclic dihydropyrrolyl compounds of Formula (V.1.2)

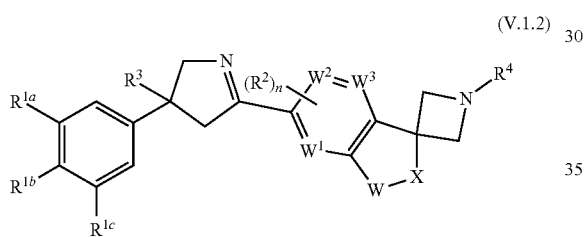
(V.1.2)

wherein $R^{1a}$, $R^{1b}$, $R^{1c}$, $W^1$, $W^2$, $W^3$, $R^2$, $R^3$, $R^4$, m and n are as defined above; X and W are each independently —O—, —$S(O)_p$—, —$NR^6$—, —$CH_2$—, —C(O)—, —$C(NR^7)$—, or —C(S)—; when X is —O—, —$S(O)_p$—, or —$NR^6$—, then W is —$CH_2$—, —C(O)—, —$C(NR^7)$—, or —C(S)—; and when W is —O—, —$S(O)_p$—, or —$NR^6$—, then X is —$CH_2$—, —C(O)—, —$C(NR^7)$—, or —C(S)—; wherein $R^6$ is hydrogen, $C_1$-$C_6$alkyl, hydroxyl, or $C_1$-$C_6$alkoxy; and wherein $R^7$ and p are as defined herein, stereoisomers thereof, and veterinary acceptable salts thereof.

In another aspect of the invention are compounds of Formula (V.1.2), $W^1$, $W^2$, and $W^3$ are each C. In yet another aspect of the invention, $W^1$ is N and $W^2$ and $W^3$ are each C, or $W^2$ is N and $W^1$ and $W^3$ are each C, or $W^3$ is N and $W^1$ and $W^2$ are each C. In yet another aspect, $W^1$ and $W^2$ are each N and $W^3$ is C. In yet another aspect, $W^1$ and $W^3$ are each N and $W^2$ is C. In yet another aspect, $W^2$ and $W^3$ are each N and $W^1$ is C. In each case, X is O and W is —C(O)— or $CH_2$—; or W is O and X is —C(O)— or —$CH_2$—; or X is —$NR^6$— and W is —$CH_2$— or —C(O)—; or W is —$NR^6$— and X is —$CH_2$— or —C(O)—; or X is $S(O)_p$ and W is —$CH_2$— or —C(O)—; or W is $S(O)_p$ and X is —$CH_2$— or —C(O)—, wherein p and $R^6$ are as defined herein, stereoisomers thereof, and veterinary acceptable salts thereof.

In another aspect of the invention of Formula (V.1.2), are spirocyclic dihydropyrrolyl compounds of Formulas (2.1), (2.2), (2.3), (2.4), (2.5), (2.6), (2.7), and (2.8)

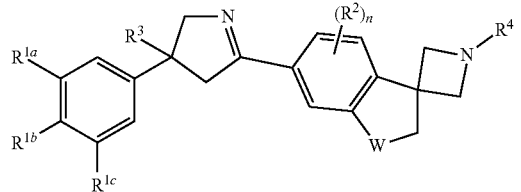
(2.1)

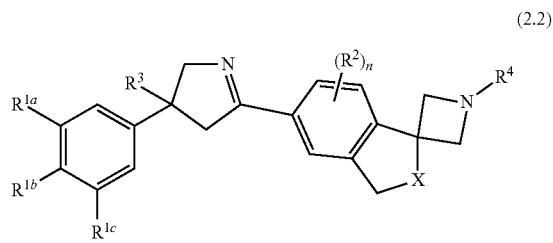
(2.2)

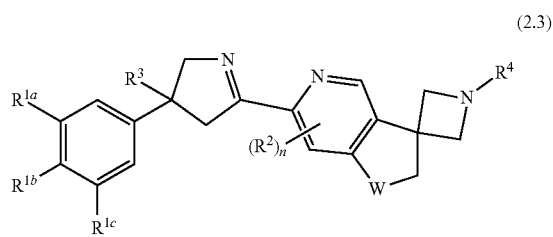
(2.3)

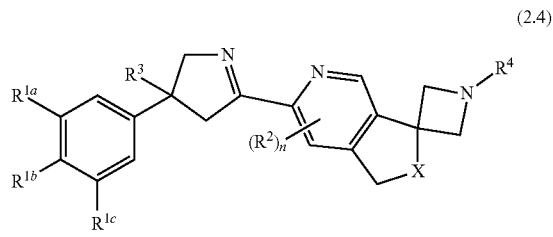
(2.4)

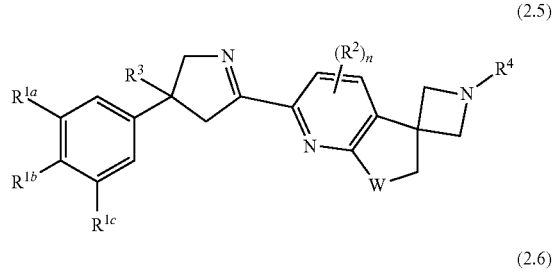
(2.5)

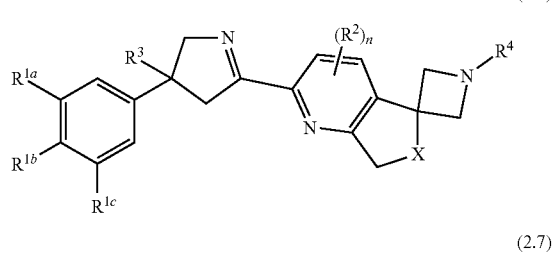
(2.6)

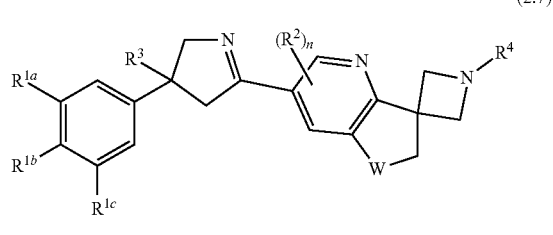
(2.7)

-continued (2.8)

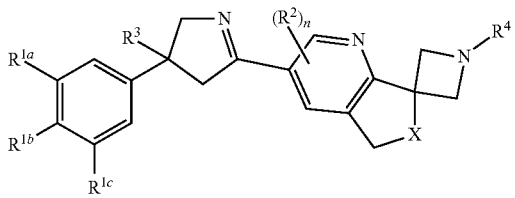

wherein $R^{1a}$, $R^{1b}$, $R^{1c}$, $R^2$, $R^3$, $R^4$, and n are as defined above, and W and X are each O or —S(O)$_p$—, wherein p is as defined above, stereoisomers thereof, and veterinary acceptable salts thereof.

In another aspect of the invention of Formula (2.2), are spirocyclic dihydropyrrolyl compounds of Formula (2.2A)

(2.2A)

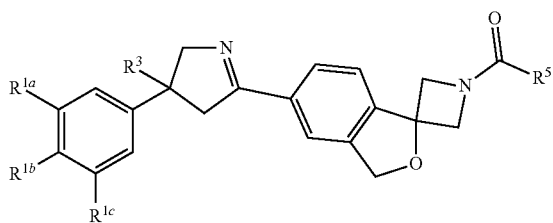

wherein $R^{1a}$, $R^{1b}$, $R^{1c}$, $R^3$, and $R^5$, are as defined herein, stereoisomers thereof, and veterinary acceptable salts thereof.

In another aspect of the invention are compounds of Formula (V.1) that are spirocyclic pyrrolidinyl compounds of Formula (V.1.3)

(V.1.3)

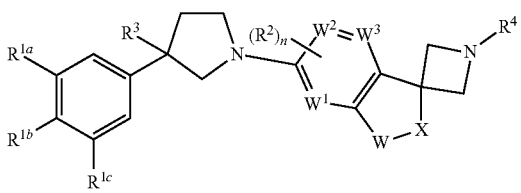

wherein $R^{1a}$, $R^{1b}$, $R^{1c}$, $W^1$, $W^2$, $W^3$, $R^2$, $R^3$, $R^4$, and n are as defined above; X and W are each independently —O—, —S(O)$_p$—, —NR$^6$—, —CH$_2$—, —C(O)—, —C(NR$^7$)—, or —C(S)—; when X is —O—, —S(O)$_p$—, or —NR$^6$—, then W is —CH$_2$—, —C(O)—, —C(NR$^7$)—, or —C(S)—; and when W is —O—, —S(O)$_p$—, or —NR$^6$—, then X is —CH$_2$—, —C(O)—, —C(NR$^7$)—, or —C(S)—; wherein $R^6$ is hydrogen, C$_1$-C$_6$alkyl, hydroxyl, or C$_1$-C$_6$alkoxy; and wherein $R^7$ and p are as defined herein, stereoisomers thereof, and veterinary acceptable salts thereof.

In another aspect of the invention are compounds of Formula (V.1.3), $W^1$, $W^2$, and $W^3$ are each C. In yet another aspect of the invention, $W^1$ is N and $W^2$ and $W^3$ are each C, or $W^2$ is N and $W^1$ and $W^3$ are each C, or $W^3$ is N and $W^1$ and $W^2$ are each C. In yet another aspect, $W^1$ and $W^2$ are each N and $W^3$ is C. In yet another aspect, $W^1$ and $W^3$ are each N and $W^2$ is C. In yet another aspect, $W^2$ and $W^3$ are each N and $W^1$ is C. In each case, X is O and W is —C(O)— or CH$_2$—; or W is O and X is —C(O)— or —CH$_2$—; or X is —NR$^6$— and W is —CH$_2$— or —C(O)—; or W is —NR$^6$— and X is —CH$_2$— or —C(O)—; or X is S(O)$_p$ and W is —CH$_2$— or —C(O)—; or W is S(O)$_p$ and X is —CH$_2$— or —C(O)—, wherein p and $R^6$ are as defined herein, stereoisomers thereof, and veterinary acceptable salts thereof.

In another aspect of the invention of Formula (V.1.3), are spirocyclic pyrrolidinyl compounds of Formulas (3.1), (3.2), (3.3), (3.4), (3.5), (3.6), (3.7), and (3.8)

(3.1)

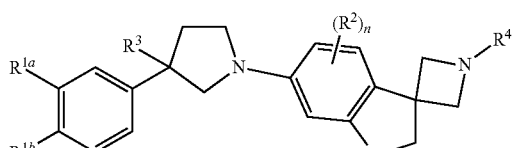

(3.2)

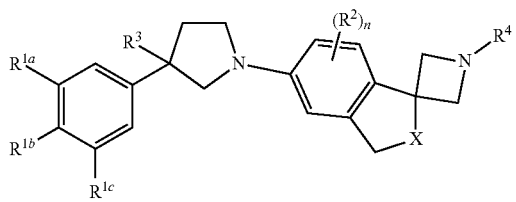

(3.3)

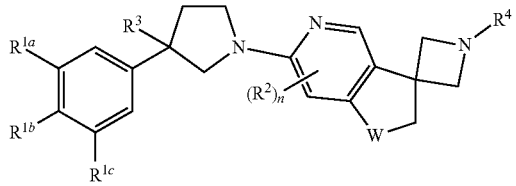

(3.4)

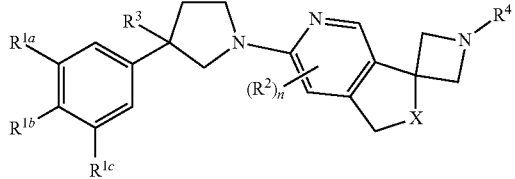

(3.5)

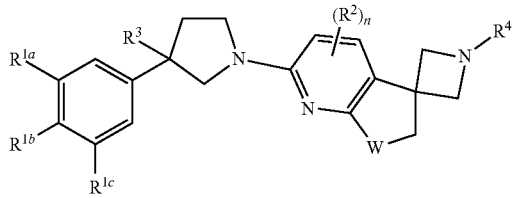

(3.6)

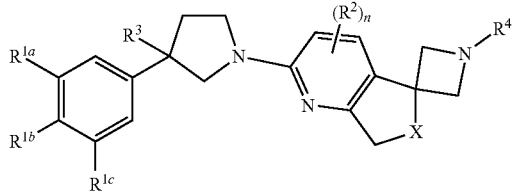

-continued (3.7)
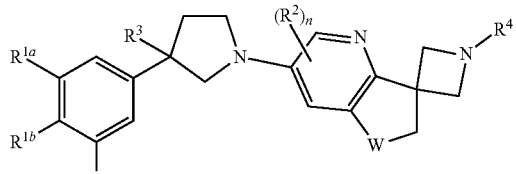

(3.8)
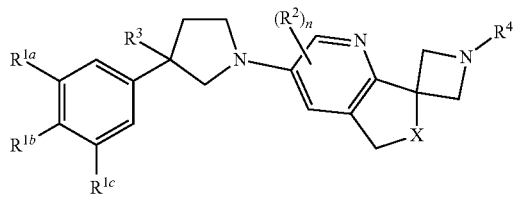

wherein $R^{1a}$, $R^{1b}$, $R^{1c}$, $R^2$, $R^3$, $R^4$, and n are as defined above, and W and X are each O or —S(O)$_p$—, wherein p is as defined above, stereoisomers thereof, and veterinary acceptable salts thereof.

In another aspect of the invention of Formula (3.2), are spirocyclic pyrrolidinyl compounds of Formula (3.2A)

(3.2A)
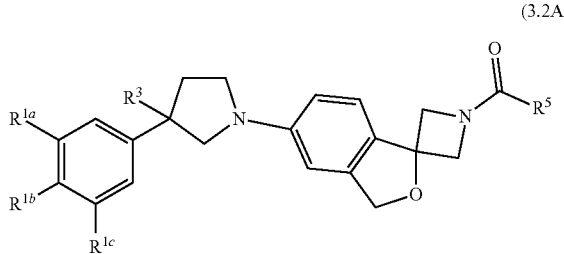

wherein $R^{1a}$, $R^{1b}$, $R^{1c}$, $R^3$, and $R^5$, are as defined herein, stereoisomers thereof, and veterinary acceptable salts thereof.

In another aspect of the invention are compounds of Formula (V.1) that are spirocyclic dihydrooxazolyl compounds of Formula (V.1.4)

(V.1.4)
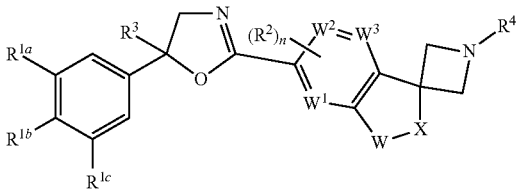

wherein $R^{1a}$, $R^{1b}$, $R^{1c}$, $W^1$, $W^2$, $W^3$, $R^2$, $R^3$, $R^4$, (and n are as defined above; X and W are each independently —O—, —S(O)$_p$—, —NR$^6$—, —CH$_2$—, —C(O)—, —C(NR$^7$)—, or —C(S)—; when X is —O—, —S(O)$_p$—, or —NR$^6$—, then W is —CH$_2$—, —C(O)—, —C(NR$^7$)—, or —C(S)—; and when W is —O—, —S(O)$_p$—, or —NR$^6$—, then X is —CH$_2$—, —C(O)—, —C(NR$^7$)—, or —C(S)—; wherein $R^6$ is hydrogen, $C_1$-$C_6$alkyl, hydroxyl, or $C_1$-$C_6$alkoxy; and wherein $R^7$ and p are as defined herein, stereoisomers thereof, and veterinary acceptable salts thereof.

In another aspect of the invention are compounds of Formula (V.1.4), $W^1$, $W^2$, and $W^3$ are each C. In yet another aspect of the invention, $W^1$ is N and $W^2$ and $W^3$ are each C, or $W^2$ is N and $W^1$ and $W^3$ are each C, or $W^3$ is N and $W^1$ and $W^2$ are each C. In yet another aspect, $W^1$ and $W^2$ are each N and $W^3$ is C. In yet another aspect, $W^1$ and $W^3$ are each N and $W^2$ is C. In yet another aspect, $W^2$ and $W^3$ are each N and $W^1$ is C. In each case, X is O and W is —C(O)— or —CH$_2$—; or W is O and X is —C(O)— or —CH$_2$—; or X is —NR$^6$— and W is —CH$_2$— or —C(O)—; or W is —NR$^6$— and X is —CH$_2$— or —C(O)—; or X is S(O)$_p$ and W is —CH$_2$— or —C(O)—; or W is S(O)$_p$ and X is —CH$_2$— or —C(O)—, wherein p and $R^6$ are as defined herein, stereoisomers thereof, and veterinary acceptable salts thereof.

In another aspect of the invention of Formula (V.1.4), are spirocyclic dihydrooxazolyl compounds of Formulas (4.1), (4.2), (4.3), (4.4), (4.5), (4.6), (4.7), and (4.8)

(4.1)
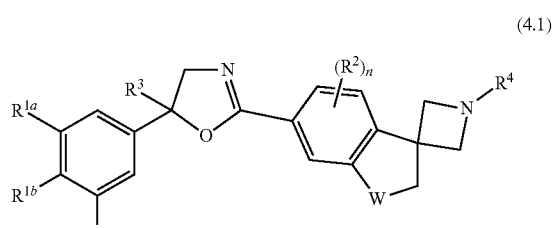

(4.2)
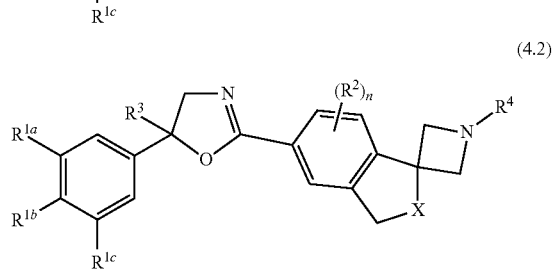

(4.3)
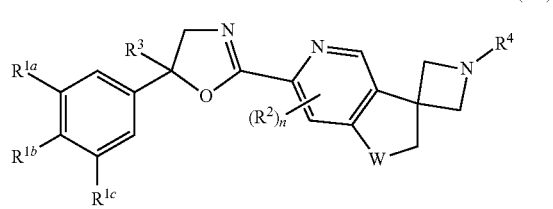

(4.4)
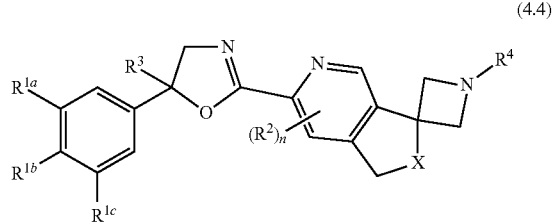

(4.5)
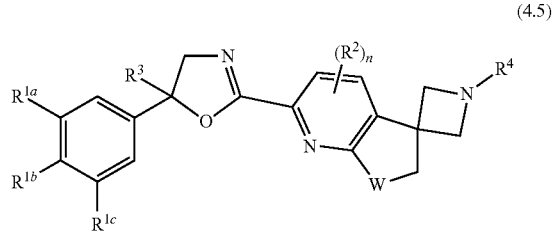

-continued (4.6)
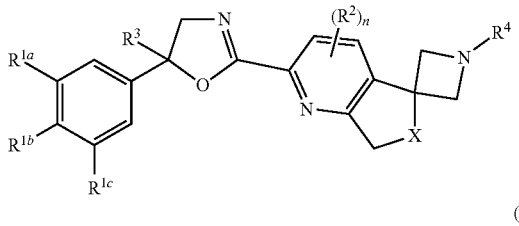

(4.7)
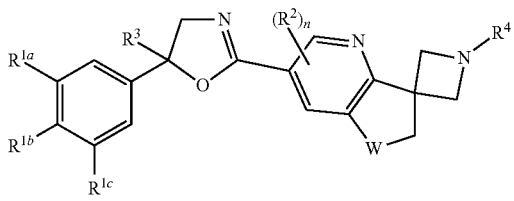

(4.8)
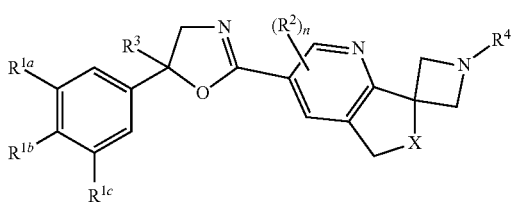

wherein $R^{1a}$, $R^{1b}$, $R^{1c}$, $R^2$, $R^3$, $R^4$, and n are as defined above, and W and X are each O or —S(O)$_p$—, wherein p is as defined above, stereoisomers thereof, and veterinary acceptable salts thereof.

In another aspect of the invention of Formula (4.2), are spirocyclic oxazole compounds of Formula (4.2A)

(4.2A)
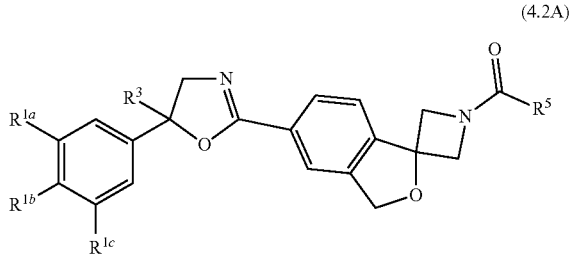

wherein $R^{1a}$, $R^{1b}$, $R^{1c}$, $R^3$, and $R^5$, are as defined herein, stereoisomers thereof, and veterinary acceptable salts thereof.

In another aspect of the invention are compounds of Formula (V.1) that are spirocyclic dioxazolyl compounds of Formula (V.1.5)

(V.1.5)
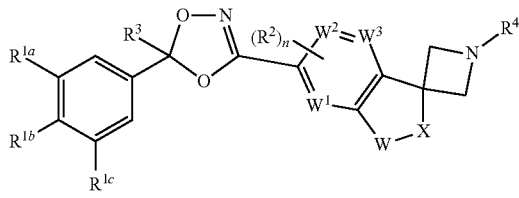

wherein $R^{1a}$, $R^{1b}$, $R^{1c}$, $W^1$, $W^2$, $W^3$, $R^2$, $R^3$, $R^4$, and n are as defined above; X and W are each independently —O—, —S(O)$_p$—, —NR$^6$—, —CH$_2$—, —C(O)—, —C(NR$^7$)—, or —C(S)—; when X is —O—, —S(O)$_p$—, or —NR$^6$—, then W is —CH$_2$—, —C(O)—, —C(NR$^7$)—, or —C(S)—; and when W is —O—, —S(O)$_p$—, or —NR$^6$—, then X is —CH$_2$—, —C(O)—, —C(NR$^7$)—, or —C(S)—; wherein $R^6$ is hydrogen, $C_1$-$C_6$alkyl, hydroxyl, or $C_1$-$C_6$alkoxy; and wherein $R^7$ and p are as defined herein, stereoisomers thereof, and veterinary acceptable salts thereof.

In another aspect of the invention are compounds of Formula (V.1.5), $W^1$, $W^2$, and $W^3$ are each C. In yet another aspect of the invention, $W^1$ is N and $W^2$ and $W^3$ are each C, or $W^2$ is N and $W^1$ and $W^3$ are each C, or $W^3$ is N and $W^1$ and $W^2$ are each C. In yet another aspect, $W^1$ and $W^2$ are each N and $W^3$ is C. In yet another aspect, $W^1$ and $W^3$ are each N and $W^2$ is C. In yet another aspect, $W^2$ and $W^3$ are each N and $W^1$ is C. In each case, X is O and W is —C(O)— or CH$_2$—; or W is O and X is —C(O)— or —CH$_2$—; or X is —NR$^6$— and W is —CH$_2$— or —C(O)—; or W is —NR$^6$— and X is —CH$_2$— or —C(O)—; or X is S(O)$_p$ and W is —CH$_2$— or —C(O)—; or W is S(O)$_p$ and X is —CH$_2$— or —C(O)—, wherein p and $R^6$ are as defined herein, stereoisomers thereof, and veterinary acceptable salts thereof.

In another aspect of the invention of Formula (V.1.5), are spirocyclic dioxazolyl compounds of Formulas (5.1), (5.2), (5.3), (5.4), (5.5), (5.6), (5.7), and (5.8)

(5.1)
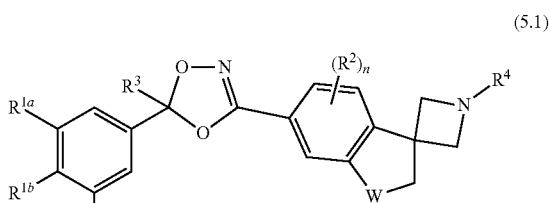

(5.2)
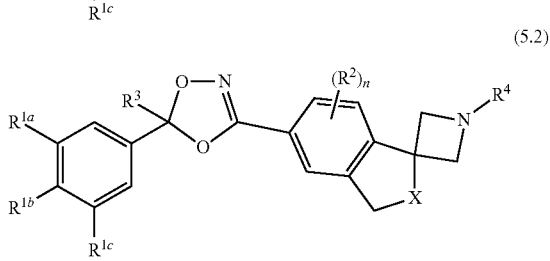

(5.3)
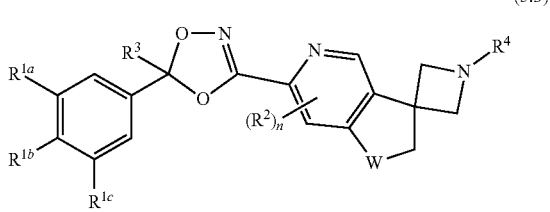

(5.4)
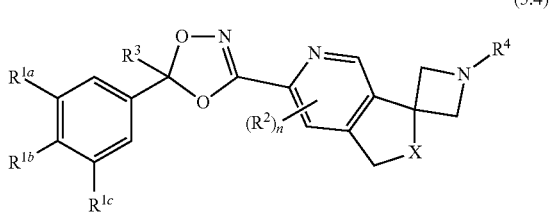

(5.5)
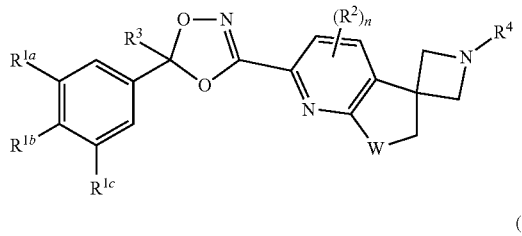

(5.6)
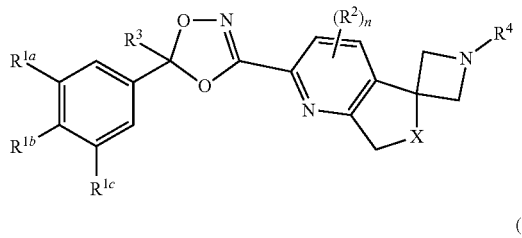

(5.7)
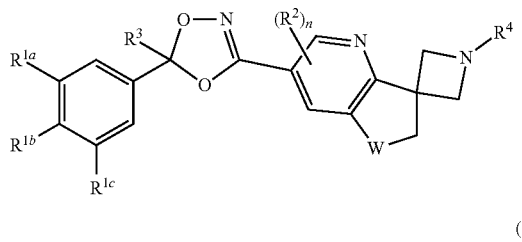

(5.8)
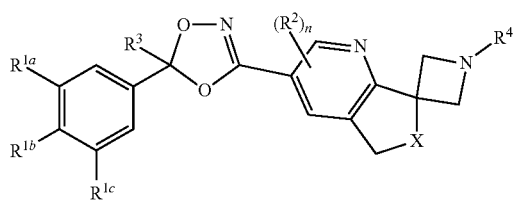

wherein $R^{1a}$, $R^{1b}$, $R^{1c}$, $R^2$, $R^3$, $R^4$, and n are as defined above, and W and X are each O or —S(O)$_p$—, wherein p is as defined above, stereoisomers thereof, and veterinary acceptable salts thereof.

In another aspect of the invention of Formula (5.2), are spirocyclic dioxazole compounds of Formula (5.2A)

(5.2A)
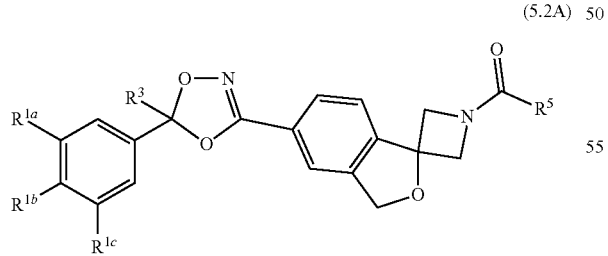

wherein $R^{1a}$, $R^{1b}$, $R^{1c}$, $R^3$, and $R^5$, are as defined herein, stereoisomers thereof, and veterinary acceptable salts thereof.

In another aspect of the invention are compounds of Formula (V.1) that are spirocyclic dihydropyrazolyl compounds of Formula (V.1.6)

(V.1.6)
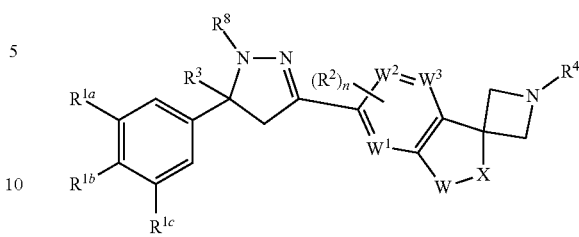

wherein $R^{1a}$, $R^{1b}$, $R^{1c}$, $W^1$, $W^2$, $W^3$, $R^2$, $R^3$, $R^4$, $R^8$, and n are as defined above; X and W are each independently —O—, —S(O)$_p$—, —NR$^6$—, —CH$_2$—, —C(O)—, —C(NR$^7$)—, or —C(S)—; when X is —O—, —S(O)$_p$—, or —NR$^6$—, then W is —CH$_2$—, —C(O)—, —C(NR$^7$)—, or —C(S)—; and when W is —O—, —S(O)$_p$—, or —NR$^6$—, then X is —CH$_2$—, —C(O)—, —C(NR$^7$)—, or —C(S)—; wherein $R^6$ is hydrogen, $C_1$-$C_6$alkyl, hydroxyl, or $C_1$-$C_6$alkoxy; and wherein $R^7$ and p are as defined herein, stereoisomers thereof, and veterinary acceptable salts thereof.

In another aspect of the invention are compounds of Formula (V.1.6), $W^1$, $W^2$, and $W^3$ are each C. In yet another aspect of the invention, $W^1$ is N and $W^2$ and $W^3$ are each C, or $W^2$ is N and $W^1$ and $W^3$ are each C, or $W^3$ is N and W' and $W^2$ are each C. In yet another aspect, $W^1$ and $W^2$ are each N and $W^3$ is C. In yet another aspect, $W^1$ and $W^3$ are each N and $W^2$ is C. In yet another aspect, $W^2$ and $W^3$ are each N and $W^1$ is C. In each case, X is O and W is —C(O)— or CH$_2$—; or W is O and X is —C(O)— or —CH$_2$—; or X is —NR$^6$— and W is —CH$_2$— or —C(O)—; or W is —NR$^6$— and X is —CH$_2$— or —C(O)—; or X is S(O)$_p$ and W is —CH$_2$— or —C(O)—; or W is S(O)$_p$ and X is —CH$_2$— or —C(O)—, wherein p and $R^6$ are as defined herein, stereoisomers thereof, and veterinary acceptable salts thereof.

In another aspect of the invention of Formula (V.1.6), are spirocyclic dihydropyrazolyl compounds of Formulas (6.1), (6.2), (6.3), (6.4), (6.5), (6.6), (6.7), and (6.8)

(6.1)
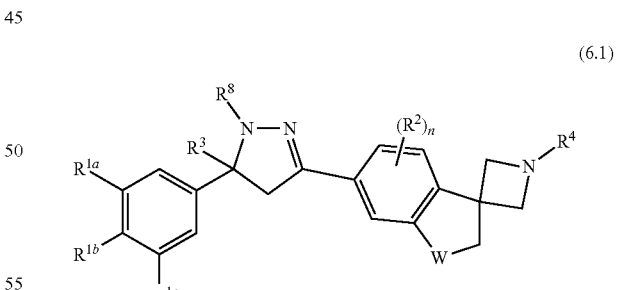

(6.2)
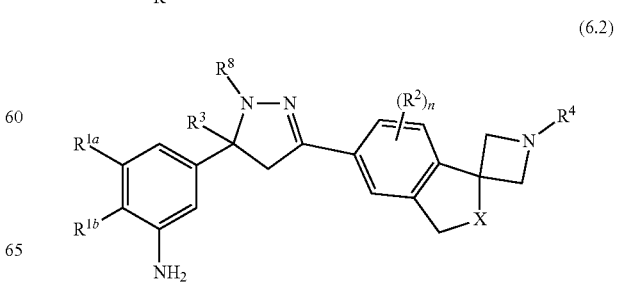

-continued (6.3)
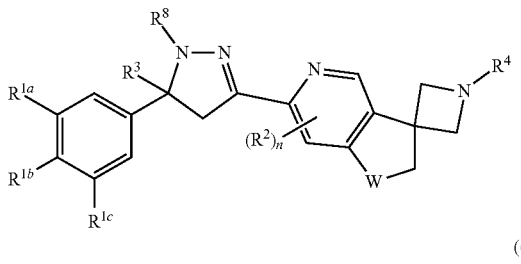

(6.4)
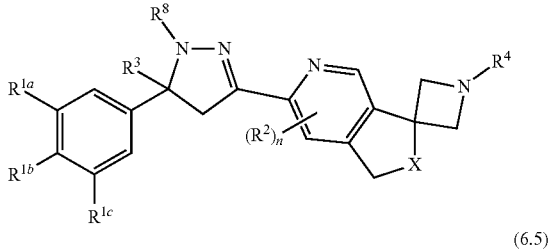

(6.5)
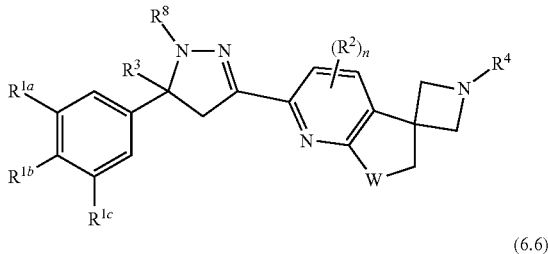

(6.6)
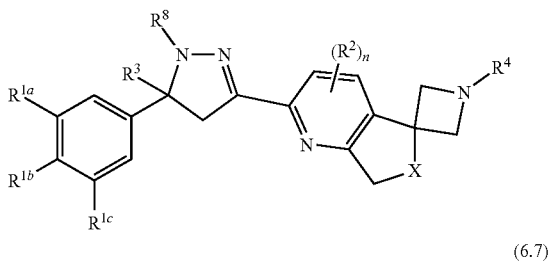

(6.7)
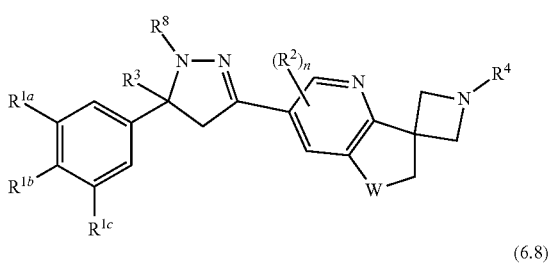

(6.8)
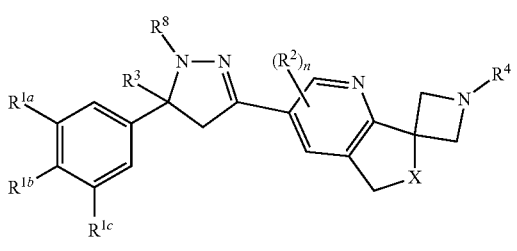

wherein $R^{1a}$, $R^{1b}$, $R^{1c}$, $R^2$, $R^3$, $R^4$, $R^8$ and n are as defined above, and W and X are each O or —S(O)$_p$—, wherein p is as defined above, stereoisomers thereof, and veterinary acceptable salts thereof.

In another aspect of the invention of Formula (6.2), are spirocyclic dihydropyrazolyl compounds of Formula (6.2A)

(6.2A)
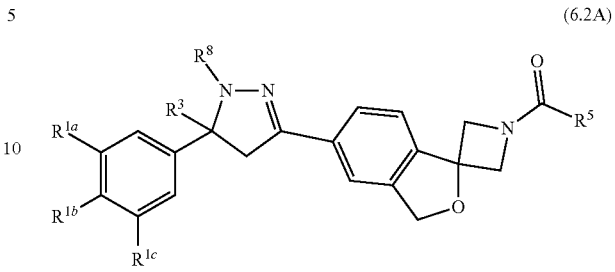

wherein $R^{1a}$, $R^{1b}$, $R^{1c}$, $R^3$, $R^5$, and $R^8$ are as defined herein, stereoisomers thereof, and veterinary acceptable salts thereof. In yet another aspect of the invention, $R^8$ is hydrogen, $C_1$-$C_6$alkyl, or $C_1$-$C_6$alkoxy. In yet another aspect of the invention, $R^8$ is hydrogen, methyl, ethyl, isopropyl, methoxy, or ethoxy. In yet another aspect of the invention, $R^8$ is hydrogen, methyl, ethyl, or methoxy. In yet another aspect of the invention, $R^8$ is hydrogen, methyl or ethyl. In yet another aspect of the invention, $R^8$ is hydrogen. In yet another aspect of the invention, $R^8$ is methyl.

In yet another aspect of the invention, each of $R^{1a}$, $R^{1b}$, and $R^{1c}$ are independently selected from hydrogen, halo, cyano, $C_1$-$C_6$ haloalkyl, and $C_0$-$C_3$alkyl$C_3$-$C_6$cycloalkyl. In yet another aspect of the invention, each of $R^{1a}$, $R^{1b}$, and $R^{1c}$ are independently selected from hydrogen, halo, cyano, and $C_1$-$C_6$ haloalkyl. In yet another aspect of the invention, each of $R^{1a}$, $R^{1b}$, and $R^{1c}$ are independently selected from hydrogen, fluoro, chloro, bromo, cyano, and $C_1$-$C_6$ haloalkyl. In yet another aspect of the invention, each of $R^{1a}$, $R^{1b}$, and $R^{1c}$ are independently selected from hydrogen, fluoro, chloro, bromo, and $C_1$-$C_6$ haloalkyl. In yet another aspect of the invention, each of $R^{1a}$, $R^{1b}$, and $R^{1c}$ are independently selected from hydrogen, fluoro, chloro, bromo, and —$CF_3$. In another aspect of the invention, each of $R^{1a}$, $R^{1b}$, and $R^{1c}$ are independently selected from chloro, fluoro, and hydrogen. In another aspect of the invention, each of $R^{1a}$, $R^{1b}$, and $R^{1c}$ are chloro. In another aspect of the invention, each of $R^{1a}$ and $R^{1c}$ are chloro and $R1^b$ is fluoro. In another aspect of the invention, each of $R^{1a}$ and $R^{1c}$ are chloro and $R1^b$ is hydrogen.

In yet another aspect of the invention, $R^2$ is halo, cyano, $C_1$-$C_6$alkyl, $C_1$-$C_6$haloalkyl, hydroxyl, —C(O)NR$^a$R$^b$, —S(O)$_p$R, or —OR. In yet another aspect of the invention, $R^2$ is halo, cyano, $C_1$-$C_6$alkyl, $C_1$-$C_6$haloalkyl, or hydroxyl. In yet another aspect of the invention, $R^2$ is fluoro, chloro, bromo, cyano, methyl, ethyl, $CF_3$, or hydroxyl. In yet another aspect of the invention, $R^2$ is fluoro, chloro, cyano, methyl, ethyl, or $CF_3$.

In yet another aspect of the invention, $R^3$ is cyano, $C_1$-$C_6$haloalkyl, or —C(O)NH$_2$. In yet another aspect of the invention, $R^3$ is cyano, $C_1$-$C_6$alkyl, or $C_6$haloalkyl. In yet another aspect of the invention, $R^3$ is cyano, methyl, ethyl, or $C_1$-$C_6$haloalkyl. In yet another aspect of the invention, $R^3$ is cyano, methyl, or $C_1$-$C_6$haloalkyl. In yet another aspect of the invention, $R^3$ is cyano or $C_1$-$C_6$haloalkyl. In yet another aspect of the invention, $R^3$ is $C_1$-$C_6$haloalkyl. In yet another aspect of the invention, $R^3$ is —$CF_3$, —$CHF_2$, —$CH_2F$, and —$CF_2Cl$. In yet another aspect of the invention, $R^3$ is —$CF_3$, —$CHF_2$, and —$CH_2F$. In yet another aspect of the invention, $R^3$ is —$CF_3$ (trifluoromethyl).

In yet another aspect of the invention, $R^4$ is hydrogen, $C_1$-$C_6$alkyl, $C_0$-$C_6$alkyl$C_3$-$C_6$cycloalkyl, —C(O)R$^5$, —C(S)

$R^5$, —C(O)NR$^a$R$^5$, —S(O)$_p$R$^c$, —S(O)$_2$NR$^a$R$^5$, —C(NR$^7$)R$^5$, C$_0$-C$_6$alkylphenyl, C$_0$-C$_6$alkylheteroaryl, or C$_0$-C$_6$alkylheterocycle. In yet another aspect of the invention, R$^4$ is hydrogen, C$_1$-C$_6$alkyl, C$_0$-C$_6$alkylC$_3$-C$_6$cycloalkyl, —C(O)R$^5$, —C(S)R$^5$, —C(O)NR$^a$R$^5$, —S(O)$_p$R$^c$, —S(O)$_2$NR$^a$R$^5$, or —C(NR$^7$)R$^5$. In yet another aspect of the invention, R$^4$ is hydrogen, C$_1$-C$_6$alkyl, C$_0$-C$_6$alkylC$_3$-C$_6$cycloalkyl, or —C(O)R$^5$. In yet another aspect of the invention, R$^4$ is hydrogen, C$_1$-C$_6$alkyl, or —C(O)R$^5$. In yet another aspect of the invention, R$^4$ is hydrogen or —C(O)R$^5$. In yet another aspect of the invention, R$^4$ is hydrogen. In yet another aspect of the invention, R$^4$ is —C(O)R$^5$. R$^4$ can be optionally substituted as defined herein.

In yet another aspect of the invention, R$^5$ is C$_1$-C$_6$alkyl, C$_0$-C$_6$alkylphenyl, C$_0$-C$_6$alkylC$_3$-C$_6$cycloalkyl, C$_0$-C$_6$alkylheteroaryl, or C$_0$-C$_6$alkylheterocycle. In yet another aspect of the invention, R$^5$ is C$_1$-C$_6$alkyl. In yet another aspect of the invention, R$^5$ is methyl, ethyl, propyl, isopropyl, t-butyl, isobutyl, and the like. Each of the R$^5$ C$_1$-C$_6$alkyls can be optionally substituted as defined herein, for example, with at least one substituent selected from hydroxyl, halo, trifluoromethyl, —S(O)$_p$R$_c$, and —NHCHO. In yet another aspect of the invention, R$^5$ is C$_0$-C$_6$alkylC$_3$-C$_6$cycloalkyl. In yet another aspect of the invention, R$^5$ is cyclopropyl, cyclobutyl, cyclopentyl, —CH$_2$cyclopropyl, —CH$_2$cyclobutyl, —CH$_2$cyclopentyl, thiatane, oxetane, azetidine, —(CH$_2$)$_2$cyclopropyl, —(CH$_2$)$_2$cyclobutyl, —(CH$_2$)$_2$cyclopentyl, —CH$_2$thiatane, —CH$_2$oxetane, —CH$_2$azetidine, tetrahydrofuran, tetrahydrothiophene, pyrrolidine, and the like. Each of the R$^5$ C$_0$-C$_6$alkylC$_3$-C$_6$cycloalkyls can be optionally substituted as defined herein, for example, with at least one substituent selected from oxo, —S(O)$_p$R$^c$, hydroxyl, —CH$_2$OH, halo, methyl, ethyl, and trifluoromethyl. In yet another aspect of the invention, R$^5$ is C$_0$-C$_6$alkylphenyl. In yet another aspect of the invention, R$^5$ is phenyl, —CH$_2$phenyl, —(CH$_2$)$_2$phenyl, and the like. In yet another aspect of the invention, The C$_0$-C$_6$alkylphenyl moieties can be optionally substituted as defined herein, for example, hydroxyl, —S(O)$_p$R$^c$, methyl, halo, and trifluoromethyl. In yet another aspect of the invention, R$^5$ is C$_0$-C$_6$alkylheteroaryl. In yet another aspect of the invention, R$^5$ is pyrazole, imidazole, pyridine, —CH$_2$pyrazole, —CH$_2$pyridine, —CH$_2$imidazole, —(CH$_2$)$_2$pyrazole, —(CH$_2$)$_2$pyridine, and —(CH$_2$)$_2$imidazole. Each of the R$^5$ C$_0$-C$_6$alkylheteroaryl moieties can be optionally substituted as defined herein, for example, with at least one substituent selected from hydroxyl, —S(O)$_p$R$^b$, methyl, halo, and trifluoromethyl. In yet another aspect of the invention, R$^5$ is C$_0$-C$_6$alkylheterocycle. In yet another aspect of the invention, R$^5$ is oxirane, thiarane, aziridine, oxetane, azetidine, thiatane, tetrahydrofuran, tetrahydrothiophene, pyrrolidine, tetrahydropyrane, piperidine, piperazine, —CH$_2$oxirane, —CH$_2$thiarane, —CH$_2$aziridine, —CH$_2$oxetane, —CH$_2$azetidine, —CH$_2$thiatane, —CH$_2$tetrahydrofuran, —CH$_2$tetrahydrothiophene, —CH$_2$pyrrolidine, —CH$_2$tetrahydropyrane, —CH$_2$piperidine, —CH$_2$piperazine, and the like. Each of the R$^5$ C$_0$-C$_6$alkylheterocyclic moieties can be optionally substituted as defined herein, for example, with at least one substituent selected from hydroxyl, —S(O)$_p$R$^b$, methyl, halo, and trifluoromethyl.

In another aspect of the invention, the integer n of (R$^2$)$_n$ is 0. In another aspect of the invention, the integer n of (R$^2$)$_n$ is 1. When the integer n is 1, then R$^2$ is as defined herein. In yet another aspect of the invention, the integer n of (R$^2$)$_n$ is 2. When the integer n is 2, then each R$^2$ is independent of each other and are as described herein.

In yet another aspect of the invention, p is the integer 0. In yet another aspect of the invention, p is the integer 1. In yet another aspect of the invention, p is the integer 2.

In yet another aspect of the invention, when X is —O— and W is —C(O)—, or when X is —O— and W is —CH$_2$—, then R$^{1a}$, R$^{1b}$, and R$^{1c}$ are each independently hydrogen, halo, or C$_1$-C$_6$haloalkyl, R$^3$ is —CF$_3$, and R$^4$ is —C(O)R$^5$; stereoisomers thereof, and veterinary acceptable salts thereof. In yet another aspect of the invention, when X is —O— and W is —C(O)—, or when X is —O— and W is —CH$_2$—, then R$^{1a}$, R$^{1b}$, and R$^{1b}$ are each independently hydrogen, halo, or C$_1$-C$_6$haloalkyl, R$^3$ is —CF$_3$, R$^4$ is —C(O)R$^5$, and R$^5$ is C$_1$-C$_6$alkyl, C$_0$-C$_6$alkylC$_3$-C$_6$cycloalkyl, C$_0$-C$_6$alkylheteroaryl, or C$_0$-C$_6$alkylheterocycle, wherein each of R$^5$ C$_1$-C$_6$alkyl or C$_0$-C$_6$alkylC$_3$-C$_6$cycloalkyl moiety can be optionally and independently substituted by at least one substituent selected from cyano, halo, hydroxyl, —CH$_2$OH, oxo, C$_1$-C$_6$alkoxy, C$_1$-C$_6$haloalkoxy, C$_1$-C$_6$haloalkyl, —S(O)$_p$R$^c$, —SH, —S(O)$_p$NR$^a$R$^b$, —NR$^a$R$^b$, —NR$^a$C(O)R$^b$, —SC(O)R, —SCN, or —C(O)NR$^a$R$^b$, and wherein each of R$^5$ C$_0$-C$_6$alkylheteroaryl or C$_0$-C$_6$alkylheterocycle moiety can be further optionally substituted with at least one substituent selected from cyano, —CH$_2$OH, halo, oxo, =S, =NR$^7$, hydroxyl, C$_1$-C$_6$alkoxy, C$_1$-C$_6$alkyl, C$_1$-C$_6$haloalkyl, —SH, —S(O)$_p$R, and C$_1$-C$_6$haloalkoxy, stereoisomers thereof, and veterinary acceptable salts thereof. More specifically, the R$^5$ C$_1$-C$_6$alkyl or C$_0$-C$_6$alkylC$_3$-C$_6$cycloalkyl moiety can be optionally and independently substituted by at least one substituent selected from halo, hydroxyl, C$_1$-C$_6$haloalkyl, —S(O)$_p$R$^c$, and —NR$^a$C(O)R$^b$. More specifically, the R$^5$ C$_0$-C$_6$alkylheteroaryl or C$_0$-C$_6$alkylheterocycle moiety can be further optionally substituted with at least one substituent selected from halo, oxo, and C$_1$-C$_6$alkyl.

In another aspect of the invention, are Formula (1.2A) spirocyclic dihydrofuranyl compounds selected from:

5'-[5-(3,5-dichlorophenyl)-5-(trifluoromethyl)-4,5-dihydrofuran-3-yl]-1-[(methylsulfonyl)acetyl]-3'H-spiro[azetidine-3,1'-[2]benzofuran];

5'-[5-(3,5-dichlorophenyl)-5-(trifluoromethyl)-4,5-dihydrofuran-3-yl]-1-isobutyryl-3'H-spiro[azetidine-3,1'-[2]benzofuran];

2-(methylsulfonyl)-1-(5'-(5-(3,4,5-trichlorophenyl)-5-(trifluoromethyl)-4,5-dihydrofuran-3-yl)-3'H-spiro[azetidine-3,1'-isobenzofuran]-1-yl)ethanone;

1-(5'-(5-(3,4,5-trichlorophenyl)-5-(trifluoromethyl)-4,5-dihydrofuran-3-yl)-3'H-spiro[azetidine-3,1'-isobenzofuran]-1-yl)propan-1-one;

5'-[5-(3,5-dichloro-4-fluorophenyl)-5-(trifluoromethyl)-4,5-dihydrofuran-3-yl]-1-[(methylsulfonyl)acetyl]-3'H-spiro[azetidine-3,1'-[2]benzofuran]; and 5'-[5-(3,5-dichloro-4-fluorophenyl)-5-(trifluoromethyl)-4,5-dihydrofuran-3-yl]-1-isobutyryl-3'H-spiro[azetidine-3,1'-[2]benzofuran], stereoisomers thereof, and veterinary acceptable salts thereof.

In another aspect of the invention, are Formula (2.2A) spirocyclic dihydropyrolyl compounds selected from:

2-(methylsulfonyl)-1-(5'-(3-(3,4,5-trichlorophenyl)-3-(trifluoromethyl)-3,4-dihydro-2H-pyrrol-5-yl)-3'H-spiro[azetidine-3,1'-isobenzofuran]-1-yl)ethanone;

2-methyl-1-(5'-(3-(3,4,5-trichlorophenyl)-3-(trifluoromethyl)-3,4-dihydro-2H-pyrrol-5-yl)-3'H-spiro[azetidine-3,1'-isobenzofuran]-1-yl)propan-1-one;

1-(5'-(3-(3,5-dichloro-4-fluorophenyl)-3-(trifluoromethyl)-3,4-dihydro-2H-pyrrol-5-yl)-3'H-spiro[azetidine-3,1'-isobenzofuran]-1-yl)-2-(methylsulfonyl)ethanone;

1-(5'-(3-(3,5-dichloro-4-fluorophenyl)-3-(trifluoromethyl)-3,4-dihydro-2H-pyrrol-5-yl)-3'H-spiro[azetidine-3,1'-isobenzofuran]-1-yl)-2-methylpropan-1-one;

1-(5'-(3-(3,5-dichlorophenyl)-3-(trifluoromethyl)-3,4-dihydro-2H-pyrrol-5-yl)-3'H-spiro[azetidine-3,1'-isobenzofuran]-1-yl)-2-(methylsulfonyl)ethanone; and 5'-[3-(3,5-dichlorophenyl)-3-(trifluoromethyl)-3,4-dihydro-2H-pyrrol-5-yl]-1-isobutyryl-3'H-spiro[azetidine-3,1'-[2]benzofuran], stereoisomers thereof, and veterinary acceptable salts thereof.

In another aspect of the invention, are Formula (3.2A) spirocyclic pyrrolidinyl compounds selected from:

5'-[3-(3,5-dichloro-4-fluorophenyl)-3-(trifluoromethyl)pyrrolidin-1yl]-1-isobutyryl-3'H-spiro[azetidine-3,1'-[2]benzofuran;

1-(5'-(3-(3,5-dichloro-4-fluorophenyl)-3-(trifluoromethyl)pyrrolidin-1-yl)-3'H-spiro[azetidine-3,1'-isobenzofuran]-1-yl)-2-(methylsulfonyl)ethanone;

5'-[3-(3,5-dichlorophenyl)-3-(trifluoromethyl)pyrrolidine-1-yl]-1-[(methylsulfonyl)acetyl]-3'H-spiro[azitidine-3,1'-[2]benzofuran];

5'-[3-(3,5-dichlorophenyl)-3-(trifluoromethyl)pyrrolidin-1yl]-1-isobutyryl-3'H-spiro[azetidine-3,1'-[2]benzofuran;

1-isobutyryl-5'-[3-(3,4,5-trichlorophenyl)-3-(trifluoromethyl)pyrrolidin-1yl]-3'H-spiro[azetidine-3,1'-[2]benzofuran; and 5'-[3-(3,4,5-trichloro)-3-(trifluoromethyl)pyrrolidin-1-yl]-1-[(methylsulfonyl)acetyl]-3'H-spiro[azetidine-3,1'-[2]benzofuran], stereoisomers thereof, and veterinary acceptable salts thereof.

In another aspect of the invention, are Formula (5.2A) spirocyclic dioxazole compounds selected from:

1-(5'-(5-(3,5-dichloro-4-fluorophenyl)-5-(trifluoromethyl)-1,4,2-dioxazol-3-yl)-3'H-spiro[azetidine-3,1'-isobenzofuran]-1-yl)-2-(methylsulfonyl)ethanone;

1-(5'-(5-(3,5-dichloro-4-fluorophenyl)-5-(trifluoromethyl)-1,4,2-dioxazol-3-yl)-3'H-spiro[azetidine-3,1'-isobenzofuran]-1-yl)-2-methylpropan-1-one;

1-(5'-(5-(3,5-dichlorophenyl)-5-(trifluoromethyl)-1,4,2-dioxazol-3-yl)-3'H-spiro[azetidine-3,1'-isobenzofuran]-1-yl)-2-(methylsulfonyl)ethanone;

1-(5'-(5-(3,5-dichlorophenyl)-5-(trifluoromethyl)-1,4,2-dioxazol-3-yl)-3'H-spiro[azetidine-3,1'-isobenzofuran]-1-yl)-2-methylpropan-1-one;

1-(5'-(5-(3,4,5-trichlorophenyl)-5-(trifluoromethyl)-1,4,2-dioxazol-3-yl)-3'H-spiro[azetidine-3,1'-isobenzofuran]-1-yl)propan-1-one; and 2-(methylsulfonyl)-1-(5'-(5-(3,4,5-trichlorophenyl)-5-(trifluoro methyl)-1,4,2-dioxazol-3-yl)-3'H-spiro[azetidine-3,1'-isobenzofuran]-1-yl)ethanone, stereoisomers thereof, and veterinary acceptable salts thereof.

In another aspect of the invention, are Formula (6.2A) spirocyclic dihydropyrazolyl compounds selected from:

1-(5'-(5-(3,5-dichloro-4-fluorophenyl)-5-(trifluoromethyl)-4,5-dihydro-1H-pyrazol-3-yl)-3'H-spiro[azetidine-3,1'-isobenzofuran]-1-yl)-2-(methylsulfonyl) ethanone;

1-(5'-(5-(3,5-dichloro-4-fluorophenyl)-1-methyl-5-(trifluoromethyl)-4,5-dihydro-1H-pyrazol-3-yl)-3'H-spiro[azetidine-3,1'-isobenzofuran]-1-yl)-2-(methylsulfonyl)ethanone;

1-(5'-(5-(3,5-dichloro-4-fluorophenyl)-5-(trifluoromethyl)-4,5-dihydro-1H-pyrazol-3-yl)-3'H-spiro[azetidine-3,1'-isobenzofuran]-1-yl)-2-methylpropan-1-one;

1-(5'-(5-(3,5-dichloro-4-fluorophenyl)-1-methyl-5-(trifluoromethyl)-4,5-dihydro-1H-pyrazol-3-yl)-3'H-spiro[azetidine-3,1'-isobenzofuran]-1-yl)-2-methylpropan-1-one;

1-(5'-(5-(3,4,5-trichlorophenyl)-5-(trifluoromethyl)-4,5-dihydro-1H-pyrazol-3-yl)-3'H-spiro[azetidine-3,1'-isobenzofuran]-1-yl)propan-1-one;

1-(5'-(5-(3,5-dichlorophenyl)-5-(trifluoromethyl)-4,5-dihydro-1H-pyrazol-3-yl)-3'H-spiro[azetidine-3,1'-isobenzofuran]-1-yl)-2-methylpropan-1-one hydrochloride;

2-(methylsulfonyl)-1-(5'-(5-(3,4,5-trichlorophenyl)-5-(trifluoromethyl)-4,5-dihydro-1H-pyrazol-3-yl)-3'H-spiro[azetidine-3,1'-isobenzofuran]-1-yl)ethanone hydrochloride; and 1-(5'-(5-(3,5-dichlorophenyl)-5-(trifluoromethyl)-4,5-dihydro-1H-pyrazol-3-yl)-3'H-spiro[azetidine-3,1'-isobenzofuran]-1-yl)methylsulfonylyethanone stereoisomers thereof, and veterinary acceptable salts thereof.

In another aspect of the invention, is a veterinary composition that comprises a Formula (V.1), (V.2), (V.1.1), (V.1.2), (V.1.3), (V.1.4), (V.1.5) or (V.1.6), compound, stereoisomer, and veterinary acceptable salt thereof.

In yet another aspect of the invention, is a veterinary composition that comprises a therapeutically effective amount of a Formula (V.1), (V.2), (V.1.1), (V.1.2), (V.1.3), (V.1.4), (V.1.5) or (V.1.6) compound, stereoisomer thereof, and veterinary acceptable salt thereof. In yet another aspect of the invention, the composition further comprises a veterinary acceptable excipient, diluent, or carrier, or mixture thereof. Preferably, the composition comprises a therapeutically effective amount of a Formula (V.1.1), (V.1.2), (V.1.3), (V.1.4), (V.1.5) or (V.1.6) compound, stereoisomer thereof, or veterinary acceptable salt thereof, and a veterinary acceptable excipient, diluent, or carrier, or mixture thereof.

In another aspect of the invention, the composition comprises a therapeutically effective amount of a Formula (V.1.1) compound, stereoisomer thereof, and a veterinary acceptable salt thereof. In another aspect of the invention, the composition comprises a therapeutically effective amount of a Formula (1.2) compound, stereoisomer thereof, and a veterinary acceptable salt thereof. In yet another aspect of the invention, the composition comprises a therapeutically effective amount of a Formula (1.2A) compound, stereoisomer thereof, and a veterinary acceptable salt thereof. The compositions further comprise a veterinary acceptable excipient, diluent, or carrier, or mixture thereof.

In another aspect of the invention, the composition comprises a therapeutically effective amount of a Formula (V.1.2) compound, stereoisomer thereof, and a veterinary acceptable salt thereof. In another aspect of the invention, the composition comprises a therapeutically effective amount of a Formula (2.2) compound, stereoisomer thereof, and a veterinary acceptable salt thereof. In yet another aspect of the invention, the composition comprises a therapeutically effective amount of a Formula (2.2A) compound, stereoisomer thereof, and a veterinary acceptable salt thereof. The compositions further comprise a veterinary acceptable excipient, diluent, or carrier, or mixture thereof.

In another aspect of the invention, the composition comprises a therapeutically effective amount of a Formula (V.1.3) compound, stereoisomer thereof, and a veterinary acceptable salt thereof. In another aspect of the invention, the composition comprises a therapeutically effective amount of a Formula (3.2) compound, stereoisomer thereof, and a veterinary acceptable salt thereof. In yet another aspect of the invention, the composition comprises a therapeutically effective amount of a Formula (3.2A) compound, stereoisomer thereof, and a veterinary acceptable salt thereof. The compositions further comprise a veterinary acceptable excipient, diluent, or carrier, or mixture thereof.

In another aspect of the invention, the composition comprises a therapeutically effective amount of a Formula (V.1.4) compound, stereoisomer thereof, and a veterinary acceptable salt thereof. In another aspect of the invention, the composition comprises a therapeutically effective amount of a Formula (4.2) compound, stereoisomer thereof, and a veterinary acceptable salt thereof. In yet another aspect of the invention, the composition comprises a therapeutically effective amount of a Formula (4.2A) compound, stereoisomer thereof, and a veterinary acceptable salt thereof. The compositions further comprise a veterinary acceptable excipient, diluent, or carrier, or mixture thereof.

In another aspect of the invention, the composition comprises a therapeutically effective amount of a Formula (V.1.5) compound, stereoisomer thereof, and a veterinary acceptable salt thereof. In another aspect of the invention, the composition comprises a therapeutically effective amount of a Formula (5.2) compound, stereoisomer thereof, and a veterinary acceptable salt thereof. In yet another aspect of the invention, the composition comprises a therapeutically effective amount of a Formula (5.2A) compound, stereoisomer thereof, and a veterinary acceptable salt thereof. The compositions further comprise a veterinary acceptable excipient, diluent, or carrier, or mixture thereof.

In another aspect of the invention, the composition comprises a therapeutically effective amount of a Formula (V.1.6) compound, stereoisomer thereof, and a veterinary acceptable salt thereof. In another aspect of the invention, the composition comprises a therapeutically effective amount of a Formula (6.2) compound, stereoisomer thereof, and a veterinary acceptable salt thereof. In yet another aspect of the invention, the composition comprises a therapeutically effective amount of a Formula (6.2A) compound, stereoisomer thereof, and a veterinary acceptable salt thereof. The compositions further comprise a veterinary acceptable excipient, diluent, or carrier, or mixture thereof.

In yet another aspect of the invention, the compositions of the invention further comprises at least one additional veterinary agent. Preferred additional veterinary agents include other known parasiticides. Examples of additional veterinary agents include, but are not limited to: amitraz, aminoacetonitriles, anthelmintics (e.g., albendazole, cambendazole, fenbendazole, flubendazole, mebendazole, octadepsipeptides, oxfendazole, oxibendazole, paraherquamide, parbendazole, piperazines, praziquantel, thiabendazole, tetramisole, triclabendazole, levamisole, pyrantel, oxantel, morantel, and the like), macrocyclic lactones and derivatives thereof (e.g., abamectin, doramectin, emamectin, eprinomectin, ivermectin, moxidectin, selamectin, milbemycin, milbemycin oxime, and the like), demiditraz, diethylcarbamazine, fipronil, hydroprene, kinoprene, methoprene, metaflumizone, niclosamide, permethrin, pyrethrins, pyriproxyfen, novaluron, fluazuron, spinosad, and mixtures thereof.

In yet another aspect of the invention is a method for treating a parasitic infection or infestation in an animal that includes the step of administering to said animal, in need of such treatment, a therapeutically effective amount of a Formula (V.1), (V.2), (V.1.1), (V.1.2), (V.1.3), (V.1.4), (V.1.5), (V.1.6), (1.2), (1.2A), (2.2), (2.2A), (3.2), (3.2A), (4.2), (4.2A), (5.2), (5.2A), (6.2), or (6.2A) compound, stereoisomer thereof, or veterinary acceptable salt thereof. In yet another aspect of the invention, the therapeutically effective amount of a compound administered to the animal is selected from a Formula (1.2), (1.2A), (2.2), (2.2A), (3.2), (3.2A), (4.2), (4.2A), (5.2), (5.2A), (6.2), or (6.2A) compound, stereoisomer, and veterinary acceptable salt thereof.

In one aspect of the invention, animal refers to an individual animal that is a mammal, bird, or fish. Specifically, mammal refers to a vertebrate animal that is human and non-human, which are members of the taxonomic class Mammalia. Specifically, bird refers to a vertebrate animal of the taxonomic class Ayes. Specifically, fish refers to the taxonomic class Chondrichthyes (cartilaginous fishes, e.g., sharks and rays) and Osteichthyes (bony fishes) which live in water, have gills or mucus-covered skin for respiration, fins, and may have scales.

In another aspect of the invention, a therapeutically effective amount of a Formula (V.1) or Formula (V.2) compound is administered to an animal in need thereof. The compound of the invention can be administered orally, topically, or by injection. Injection encompasses subcutaneous injection, parenteral injection, and intramuscular injection. Preferably, the compounds of the present invention, and compositions thereof, are administered to the animal orally or topically.

In another aspect of the invention, are compounds of Formula (1.2A) in Table 1, stereoisomers thereof, and veterinary acceptable salts thereof. In another aspect of the invention, are compounds of Formula (2.2A) in Table 2, stereoisomers thereof, and veterinary acceptable salts thereof. In another aspect of the invention, are compounds of Formula (3.2A) in Table 3, stereoisomers thereof, and veterinary acceptable salts thereof. In another aspect of the invention, are compounds of Formula (4.2A) in Table 7, stereoisomers thereof, and veterinary acceptable salts thereof. In another aspect of the invention, are compounds of Formula (5.2A) in Table 6, stereoisomers thereof, and veterinary acceptable salts thereof. In another aspect of the invention, are compounds of Formula (6.2A) in Table 4 and Table 5, stereoisomers thereof, and veterinary acceptable salts thereof.

In another aspect of the invention is a composition comprising a compound selected from Table 1, Table 2, Table 3, Table 4, Table 5, Table 6, or Table 7. In another aspect of the invention, the composition further comprises a veterinary acceptable excipient, diluents, carrier, or mixture thereof. In yet another aspect of the invention, the composition further comprises an additional veterinary agent(s). The additional veterinary agent(s) are described herein.

Compound names in this application were named by either ChemBioDraw Ultra 12.0 or by IUPAC naming conventions.

All of the recited WO patent publications and PCT/IB applications described herein, are hereby incorporated in their entirety.

DEFINITIONS

For purposes of the present invention, as described and claimed herein, the following terms and phrases are defined as follows:

"Additional veterinary agent(s)" as used herein, unless otherwise indicated, refers to other veterinary or pharmaceutical compounds or products that provide a therapeutically effective amount of said agents that are useful for the treatment of a parasitic infection in an animal, as described herein.

"Alkoxy", as used herein, unless otherwise indicated, refers to an oxygen moiety having a further alkyl substituent. The alkyl portion (i.e., alkyl moiety) of an alkoxy group has the same definition as below. Non-limiting examples include: —OCH$_3$, —OCH$_2$CH$_3$, and the like.

"Alkyl", as used herein, unless otherwise indicated, refers to saturated monovalent hydrocarbon alkane radicals of the general formula $C_nH_{2n+1}$. The alkane radical may be straight or branched and may be unsubstituted or substituted. For example, the term "(C$_1$-C$_6$)alkyl" refers to a monovalent, straight or branched aliphatic group containing 1 to 6 carbon atoms. Non-exclusive examples of ($C_1$-$C_6$) alkyl groups include, but are not limited to methyl, ethyl, propyl, isopropyl, sec-butyl, t-butyl, n-propyl, n-butyl, i-butyl, s-butyl, n-pentyl, 1-methylbutyl, 2-methylbutyl, 3-methylbutyl, neopentyl, 3,3-dimethylpropyl, 2-methylpentyl, hexyl, and the like. The alkyl moiety may be attached to the chemical moiety by any one of the carbon atoms of the aliphatic chain. Alkyl groups are optionally substituted as described herein. Further when used in compound words such as $C_0$-$C_3$alkylphenyl, said alkyl moiety has the same meaning as herein defined and may be attached to the chemical moiety by any one of the carbon atoms of the aliphatic chain, when said carbon atom(s) is present, otherwise the remaining molecular term, herein phenyl, is directly linked to the chemical moiety. Non-limiting examples of the compound word, $C_0$-$C_3$alkylphenyl include: $C_0$phenyl is phenyl, $C_1$alkylphenyl is —$CH_2$phenyl, $C_2$alkylphenyl is —$CH_2CH_2$phenyl, and the like.

"Alkenyl" as used herein, unless otherwise indicated, refers to a straight or branched aliphatic hydrocarbon chain having 2- to 6-carbon atoms and containing at least one carbon-carbon double bond (for example —C═C—, or —C═$CH_2$). Non-exclusive examples of alkenyl include: ethenyl, 1-propenyl, 2-propenyl, isopropenyl, 1-butenyl, 2-butenyl, 3-butenyl, 2-pentenyl, and the like. "Alkynyl" as used herein, unless otherwise indicated, refers to straight or branched aliphatic hydrocarbon chain having 2- to 6-carbon atoms and containing at least one carbon-carbon triple bond (for example, —C≡C— or —C≡CH). Non-exclusive examples of alkynyl include: ethynyl, 2-propynyl, 1-methyl-2-propynyl, 2-butynyl, 3-butynyl, 2-methyl-3-butynyl, and the like. "Animal(s)", as used herein, unless otherwise indicated, refers to an individual animal that is a mammal, bird, or fish. Specifically, mammal refers to a vertebrate animal that is human and non-human, which are members of the taxonomic class Mammalia. Non-exclusive examples of non-human mammals include companion animals and livestock. Non-exclusive examples of a companion animal include: dog, cat, llama, and horse. Preferred companion animals are dog, cat, and horse. More preferred is dog. Non-exclusive examples of livestock include: swine, camel, rabbits, goat, sheep, deer, elk, bovine (cattle), and bison. Preferred livestock is cattle and swine. Specifically, bird refers to a vertebrate animal of the taxonomic class Ayes. Birds are feathered, winged, bipedal, endothermic, and egg-laying. Non-exclusive examples of bird include, poultry (e.g., chicken, turkey, duck, and geese), all of which are also referred to herein as fowl. Specifically, fish refers to the taxonomic class Chondrichthyes (cartilaginous fishes, e.g., sharks and rays) and Osteichthyes (bony fishes) which live in water, have gills or mucus-covered skin for respiration, fins, and may have scales. Non-exclusive examples of fish include shark, salmon, trout, whitefish, catfish, tilapia, sea bass, tuna, halibut, turbot, flounder, sole, striped bass, eel, yellowtail, grouper, and the like. "Carbocyclic", as used herein, unless otherwise indicated, refers to a partially saturated or saturated 5- to 7-membered ring containing only carbon atoms and can be monocyclic or part of a fused ring or spiro ring moiety. Examples of carbocyclic rings include cyclopentane, cyclohexane, and cycloheptane. The carbocyclic ring is optionally substituted as described herein.

"Chiral", as used herein, unless otherwise indicated, refers to the structural characteristic of a molecule that makes it impossible to superimpose it on its mirror image, (e.g., "R" and "S" enantiomers). The term is sometimes depicted as an asterisk (i.e., *) in the Examples and preparations which refers to the chiral center which includes both the S and R enantiomers.

"Compounds of the present invention", as used herein, unless otherwise indicated, refers to Formula (V.1), (V.2), (V.1.1), (V.1.2), (V.1.3), (V.1.4), (V.1.5) or (V.1.6) compounds, stereoisomers thereof, and veterinary acceptable salts thereof. The phrase also refers to Formula (1.1) to (1.8), (1.2A), (2.1) to (2.8), (2.2A), (3.1) to (3.8), (3.2A), (4.1) to (4.8), (4.2A), (5.1) to (5.8), (5.2A), (6.1) to (6.8), and (6.2A) compounds, stereoisomers thereof, and veterinary acceptable salts thereof. The term instant is equivalent to the term present.

"Cycloalkyl", as used herein, unless otherwise indicated, includes fully saturated or partially saturated carbocyclic alkyl moieties. Non-limiting examples of partially saturated cycloalkyls include: cyclopropene, cyclobutene, cycloheptene, cyclooctene, cyclohepta-1,3-diene, and the like. Preferred cycloalkyls are 3- to 6-membered saturated monocyclic rings including cyclopropyl, cyclobutyl, cyclopentyl, and cyclohexyl. The cycloalkyl group may be attached to the chemical moiety by any one of the carbon atoms within the carbocyclic ring. Cycloalkyl groups are optionally substituted with at least one substituent. Further when used in compound words such as $C_0$-$C_3$alkyl$C_3$-$C_6$cycloalkyl, said alkyl moiety has the same meaning as herein defined and may be attached to the chemical moiety by any one of the carbon atoms of the aliphatic chain, when said carbon atom(s) is present, otherwise the remaining molecular term, herein $C_3$-$C_6$cycloalkyl, is directly linked to the chemical moiety. Non-limiting examples of the compound word, $C_0$-$C_6$alkyl$C_3$-$C_6$cycloalkyl include: cylcopropane ($C_0$alkyl$C_3$cycloalkyl or $C_3$cycloalkyl), methylcyclopropane ($C_1$alkyl$C_3$cycloalkyl or —$CH_2$cyclopropane), ethylcyclopropane ($C_2$alkyl$C_3$cycloalkyl or —$CH_2CH_2$cyclopropane), methylcyclobutane ($C_1$alkyl$C_4$cycloalkyl or —$CH_2$cyclobutane), ethylcyclobutane ($C_2$alkyl$C_4$cycloalkyl or —$CH_2CH_2$cyclobutane), methylcyclohexane ($C_1$alkyl$C_6$cycloalkyl or —$CH_2$cyclohexane), and the like. Cycloalkyl moieties are optionally substituted as described herein.

"E/Z Notation" or "E and Z geometric isomer(s)", as used herein, unless otherwise indicated, refers to the International Union of Pure and Applied Chemistry (IUPAC) preferred method of describing the stereochemistry of double bonds in organic chemistry. It is an extension of cis/trans notation that can be used to describe double bonds having three or four substituents. Following a set of defined rules (Cahn-lngold-Prelog priority rules), each substituent on a double-bond is assigned a priority. If the two groups of higher priority are on opposite sides of the double bond, the bond is assigned the configuration E (from entgegen, the German word for "opposite"). If the two groups of higher priority are on the same side of the double bond, the bond is assigned the configuration Z (from zusammen, the German word for "together").

"Halogen" or "halo", as used herein, unless otherwise indicated, refers to fluorine, chlorine, bromine and iodine. Further, when used in compound words such as "haloalkyl", "haloalkoxy", "haloalkenyl", or "haloalkynyl", said alkyl, alkoxy, alkenyl, and alkynyl may be partially or fully substituted with halogen atoms which may be the same or different and said alkyl, alkoxy, alkenyl, and alkynyl moiety has the same meaning as above and may be attached to the chemical moiety by any one of the carbon atoms of the aliphatic chain. Examples of "haloalkyl" include $F_3C$—, $ClCH_2$—, $CF_3CH_2$— and $CF_3CCl_2$—, and the like. The term "haloalkoxy" is defined analogously to the term "haloalkyl". Examples of "haloalkoxy" include $CF_3O$—, $CCl_3CH_2O$—, $HCF_2CH_2CH_2O$— and $CF_3CH_2O$—, and the like. The term "haloalkenyl is defined analogously to the term "haloalkyl"

except that the aliphatic chain contains at least one carbon-carbon double bond. Examples of "haloalkenyl" include $CF_3C=C—$, $CCl_3C=C—$, $HCF_2C=C—$ and $CF_3C=C—$, and the like. The term "haloalkynyl" is defined analogously to the term "haloalkyl" except that the aliphatic chain contains at least one carbon-carbon triple bond. Examples of "haloalkynyl" include $CF_3C≡C—$, $CCl_3C≡C—$, $HCF_2C≡C—$ and $CF_3C≡C—$, and the like.

"Heteroaryl" or "Het", as used herein, unless otherwise indicated, refers to a 5- to 6-membered aromatic monocyclic ring or an 8- to 10-membered fused aromatic ring where said monocyclic- and fused-ring moiety contains one or more heteroatoms each independently selected from N, O, or S, preferably from one to four heteroatoms. Non-exclusive examples of monocyclic heteroaryls include pyrrolyl, furanyl, thiophenyl, pyrazolyl, imidazolyl, triazolyl, tetrazolyl, thiazolyl, isoxazolyl, oxazolyl, oxadiazolyl, thiadiazolyl, pyridinyl, pyridazinyl, pyrimidinyl, pyrazinyl, and the like. Non-exclusive examples of fused heteroaryls include: benzofuranyl, benzothiophenyl, indolyl, benzimidazolyl, indazolyl, benzotriazolyl, thieno[2,3-c]pyridine, thieno[3,2-b]pyridine, benzo[1,2,5]thiadiazole, and the like. The heteroaryl group may be attached to the chemical moiety by any one of the carbon atoms or nitrogen heteroatoms within the monocyclic or fused ring. Further when used in compound words such as alkylheteroaryl, said alkyl and heteroaryl moiety have the same meaning as herein defined and may be attached to the chemical moiety by any one of the carbon atoms of the aliphatic chain, when applicable. For example, $C_0$alkylheteroaryl is heteroaryl, $C_1$alkylheteroaryl is —$CH_2$heteroaryl, $C_2$alkylheteroaryl is —$CH_2CH_2$heteroaryl, and the like. Heteroaryls are optionally substituted as described herein.

"Heterocycle", as used herein, unless otherwise indicated, refers to a partially saturated or saturated 3- to 7-membered monocyclic ring containing one or more heteroatoms each independently selected from N, O, or S, preferably from one to four heteroatoms. The heterocyclic ring can be part of a fused ring or spiro-ring moiety. Non-exclusive examples of heterocycle include oxirane, thiarane, aziridine, oxetane, azetidine, thiatane, tetrahydrofuran, tetrahydrothiophene, pyrrolidine, tetrahydropyrane, piperidine, piperazine, tetrahydropyridine, 2H-azirine, 2,3-dihydro-azete, 3,4-dihydro-2H-pyrrole, and the like. The heterocycle group may be attached to the chemical moiety by any one of the carbon atoms or nitrogen heteroatoms within the ring. Further when used in compound words such as alkylheterocycle, said alkyl and heterocycle moiety have the same meaning as herein defined and may be attached to the chemical moiety by any one of the carbon atoms of the aliphatic chain, when applicable. For example, $C_0$alkylheterocycle is heterocycle, $C_1$alkylheterocycle is —$CH_2$heterocycle, $C_2$alkylheterocycle is —$CH_2CH_2$heterocycle, and the like. Heterocycles are optionally substituted as described herein.

"Optionally substituted", is used herein interchangeably with the phrase substituted or unsubstituted. Unless otherwise indicated, an optionally substituted group may have a substituent at each substitutable position of the group, and each substitution is independent of the other. An optionally substituted group also may have no substituents. Therefore, the phrase "optionally substituted with at least one substituent" means that the number of substituents may vary from zero up to a number of available positions for substitution.

"Parasite(s)", as used herein, unless otherwise indicated, refers to endoparasites and ectoparasites. Endoparasites are parasites that live within the body of its host and include helminths (e.g., trematodes, cestodes, and nematodes) and protozoa. Ectoparasites are organisms of the Arthropoda phylum (e.g., arachnids, insects, and crustaceans (e.g., copepods-sea lice) which feed through or upon the skin of its host. Preferred arachnids are of the order Acarina, e.g., ticks and mites. Preferred insects are midges, fleas, mosquitos, biting flies (stable fly, horn fly, blow fly, horse fly, and the like), bed bugs, and lice. Preferred compounds of the present invention can be used for the treatment of parasites, i.e., as a parasiticide.

"Protecting group" or "Pg", as used herein, unless otherwise indicated, refers to a substituent that is commonly employed to block or protect an amine on the compound thereby protecting its functionality while allowing for the reaction of other functional groups on the compound. Non-exclusive examples of an amine-protecting group include: acyl groups (e.g., formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl, and the like), acyloxy groups (e.g., 1-tert-butyloxycarbonyl (Boc), methoxycarbonyl, 9-fluorenyl-methoxycarbonyl, 2,2,2-trifluoroethoxycarbonyl, 2-trimethylsilylethxoycarbonyl, vinyloxycarbonyl, allyloxycarbonyl, 1,1-dimethyl-propynyloxycarbonyl, benzyloxy-carbonyl, p-nitrobenzyloxycarbony, 2,4-dichlorobenzyloxycarbonyl, and the like), diphenylmethane, and benzylcarbamates.

"Sulfonate leaving group", as used herein, unless otherwise indicated, refers to anions with the general formula $RSO_2O^-$. Non limiting examples of a sulfonate leaving group include: mesylate (R=$CH_3$), triflate (R=$CF_3$), tosylate (R=$CH_3C_6H_4$), besylate (R=$C_6H_5$), tresylate (R=$CH_2CF_3$), and the like. "Therapeutically effective amount", as used herein, unless otherwise indicated, refers to an amount of the compounds of the present invention that (i) treat the particular parasitic infection or infestation, (ii) attenuates, ameliorates, or eliminates one or more symptoms of the particular parasitic infection or infestation, or (iii) prevents or delays the onset of one or more symptoms of the particular parasitic infection or infestation described herein.

"Treatment", "treating", and the like, as used herein, unless otherwise indicated, refers to reversing, alleviating, or inhibiting the parasitic infection, infestation, or condition. As used herein, these terms also encompass, depending on the condition of the animal, preventing the onset of a disorder or condition, or of symptoms associated with a disorder or condition, including reducing the severity of a disorder or condition or symptoms associated therewith prior to affliction with said infection or infestation. Thus, treatment can refer to administration of the compounds of the present invention to an animal that is not at the time of administration afflicted with the infection or infestation. Treating also encompasses preventing the recurrence of an infection or infestation or of symptoms associated therewith as well as references to "control" (e.g., kill, repel, expel, incapacitate, deter, eliminate, alleviate, minimize, and eradicate).

"Veterinary acceptable" as used herein, unless otherwise indicated, indicates that the substance or composition must be compatible chemically and/or toxicologically, with the other ingredients comprising a formulation, composition, and/or the animal being treated therewith. The term also contemplates "pharmaceutical or pharmaceutically" acceptable.

DETAILED DESCRIPTION

The present invention provides Formula (V.1), (V.2), (V.1.1), (V.1.2), (V.1.3), (V.1.4), (V.1.5) and (V.1.6) compounds, stereoisomers thereof, veterinary acceptable salts thereof, as well as veterinary compositions that are useful as antiparasitic agents for animals, in particular, compounds that act as ectoparasiticides and endoparasiticides. The present invention also provides Formula (1.1) to (1.8), Formula (2.1) to (2.8), Formula (3.1) to (3.8), Formula (4.1) to (4.8), Formula (5.1) to (5.8), and Formula (6.1) to (6.8) compounds, stereoisomers thereof, and veterinary acceptable salts thereof. The present invention also provides Formula (1.2A), (2.2A), (3.2A), (4.2A), (5.2A), and (6.2A) compounds, stereoisomers thereof, and veterinary acceptable salts thereof, compositions thereof, and methods of using said compounds for the treatment of a parasitic infection or infestation in an animal.

Compounds of the present invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, "Reagents for Organic Synthesis", 1; 19, Wiley, N.Y. (1967, 1999 ed.), or Beilsteins Handbuch der organischen Chemie, 4, Aufl. ed. Springer-Verlag, Berlin, including supplements (also available via the Beilstein online database)). For illustrative purposes, the reaction schemes depicted below demonstrate potential routes for synthesizing compounds of the present invention, and key intermediates. For a more detailed description of the individual reaction steps, see the Examples section below. A skilled artisan will appreciate that other suitable starting materials, reagents, and synthetic routes may be used to synthesize the compounds of the present invention and a variety of derivatives thereof. Further, many of the compounds prepared by the methods described below can be further modified in light of this disclosure using conventional chemistry well known to the skilled artisan.

Compounds of the present invention described herein contain at least one asymmetric or chiral center; and, therefore, exist in different stereoisomeric forms. The R and S configurations are based upon knowledge of known chiral inversion/retention chemistry. Unless specified otherwise, it is intended that all stereoisomeric forms of the compounds of the present invention as well as mixtures thereof, including racemic mixtures and diastereomeric mixtures, form part of the present invention.

Enantiomeric mixtures can be separated into their individual enantiomers on the basis of their physical chemical differences by methods well known to those skilled in the art, such as chromatography and/or fractional crystallization. A more detailed description of techniques that can be used to resolve stereoisomers of compounds from their racemic mixture can be found in Jean Jacques Andre Collet, Samuel H. Wilen, Enantiomers, Racemates and Resolutions, John Wiley and Sons, Inc. (1981).

Compounds of this invention can exist as one or more stereoisomers. The various stereoisomers include enantiomers, diastereomers and atropisomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereo isomers or as an optically active form. For example, two possible enantiomeric compounds of Formula 1 are depicted as Formula 1a and Formula 1b involving the chiral center identified with an asterisk (*). Molecular depictions drawn herein follow standard conventions for depicting stereochemistry.

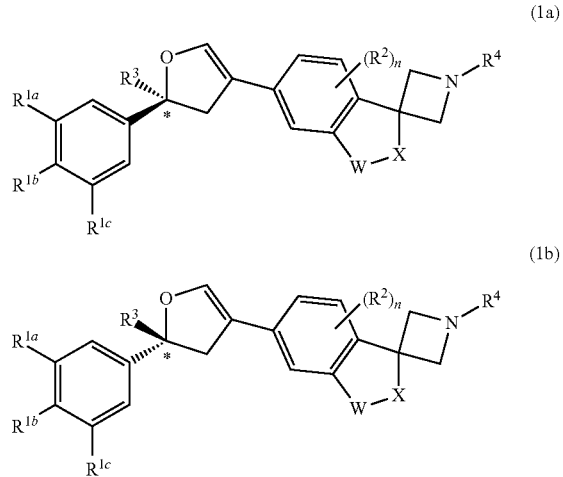

For illustrative purposes, the reaction schemes depicted below demonstrate potential routes for synthesizing key intermediates and compounds of the present invention. For a more detailed description of the individual reaction steps, see the Examples section below. Those skilled in the art will appreciate that other suitable starting materials, reagents, and synthetic routes may be used to synthesize the intermediates and compounds of the present invention and a variety of derivatives thereof. Further, many of the compounds prepared by the methods described below can be further modified in light of this disclosure using conventional chemistry. Schemes 1-7 outline the general procedures useful for the preparation and isolation of compounds of the present invention. It is to be understood, however, that the invention, as fully described herein and as recited in the claims, is not intended to be limited by the details of the following schemes or modes of preparation.

In the preparation of compounds of the present invention, protection of remote functionality of intermediates from undesired reactions can be accomplished with a protecting group. The term "protecting group" or "Pg" refers to a substituent that is commonly employed to block or protect a particular functionality while reacting other functional groups on the compound. For example, an amine-protecting group is a substituent attached to an amine that blocks or protects the amine-functionality of the compound or intermediate. Suitable amine protecting groups include: 1-tert-butyloxycarbonyl (Boc), acyl groups including: formyl, acetyl, chloroacetyl, trichloro-acetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl, and the like; and acyloxy groups including: methoxycarbonyl, 9-fluorenyl-methoxycarbonyl, 2,2,2-trifluoroethoxycarbonyl, 2-trimethylsilylethxoycarbonyl, vinyloxycarbonyl, allyloxycarbonyl, 1,1-dimethyl-propynyloxycarbonyl, benzyloxy-carbonyl, p-nitrobenzyloxycarbony, 2,4-dichlorobenzyloxycarbonyl, and the like. Similarly, diphenylmethane and benzylcarbamates can be used as amine protecting groups. Suitable protecting groups and their respective uses are readily determined by one skilled in the art. For a general description of protecting groups and their use, see T. W. Greene, *Protective Groups in Organic Synthesis*, John Wiley & Sons, New York, 1991.

In the Schemes and Examples below, the following catalysts/reactants and miscellaneous abbreviations include: equivalent(s) (eq); mobile phase (MP); round bottom flask (RBF); N,N-dimethyl formamide (DMF); trimethylsilyl (TMS); 4,5-bis(diphenylphosphino)-9,9-dimethylxanthene (Xantphos); dimethyl acetamide (DMA); acetonitrile (ACN or Acn); dichloromethane (DCM); N-chloro-succinimide (NCS); ethanol (EtOH); methyl tert-butyl ether (MTBE); triethylamine (TEA or Et₃N); methanol (MeOH), tetrahydrofuran (THF); ethyl acetate (EtOAc); trifluoroacetic acid (TFA); 4-dimethylaminopyridine (DMAP); 1,3-bis(diphenylphosphino)-propane (DPPP); amidecarbonyldiimidazole (CDI); 1-hydroxybenzotriazole hydrate (HOBt); N,N,N',N'-Tetramethyl-O-(7-azabenzotriazol-1-yl)uronium hexafluorophosphate (HATU), isopropylmagnesium chloride (iPrMgCl); t-butyloxycarbonyl (BOC, Boc, boc); palladium(II) acetate (Pd(OAc)₂); thin layer chromatography (TLC), lithium chloride (LiCl); dimethyl sulfoxide (DMSO); dichloroethane (DCE); propylphosponic anhydride (T₃P); dimethyl ether (DME); tetrabutylammonium fluoride (TBAF); 1,8-diazabicycloundec-7-ene (DBU); N,N-diisopropylethylamine (DIPEA); 1-ethyl-3-(3-dimethylaminopropyl)carbodiimide (EDC); and tris(dibenzylideneacetone)-dipalladium (Pd₂(dba)₃).

Schemes

Scheme 1: Synthesis of dihydropyrroles

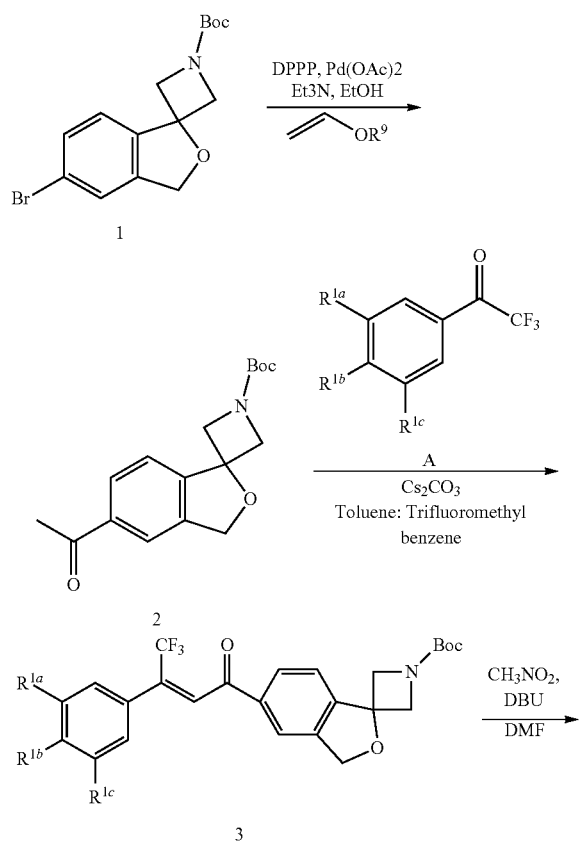

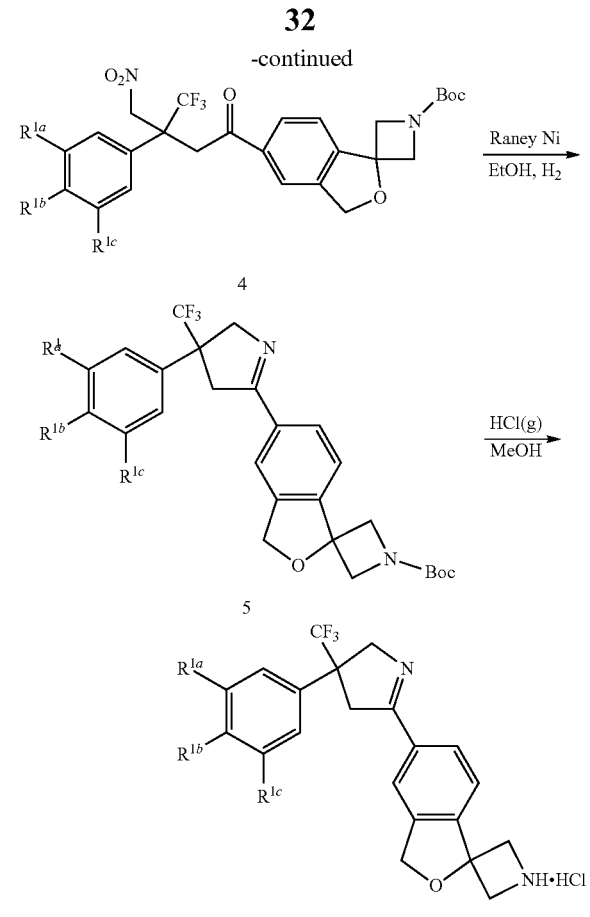

$R^9$ is $C_1$-$C_6$alkyl. $R^{1a}$, $R^{1b}$, $R^{1c}$ are as defined herein.

Chalcone 3 can be prepared by coupling of the bromoisobenzofuran 1 with a vinyl ether and condensation of the resulting acetophenone with a substituted trifluoroacetophenone of compound A with an appropriate base such as CsCO₃. Addition of nitromethane to 3 followed by nitro reduction and cyclization provides the protected dihydropyrroles 5. Deprotection provides the desired spiroazetidine dihydropyrrole intermediates 6.

Scheme 2: Synthesis of dihydrofurans

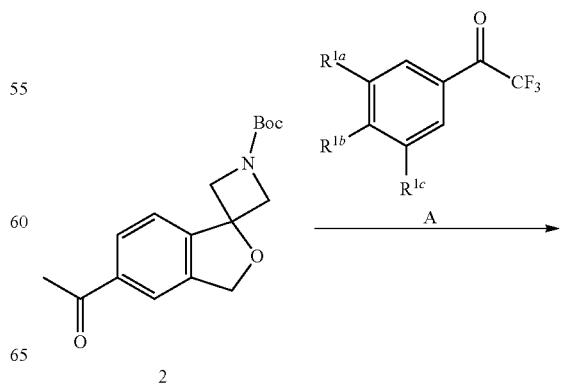

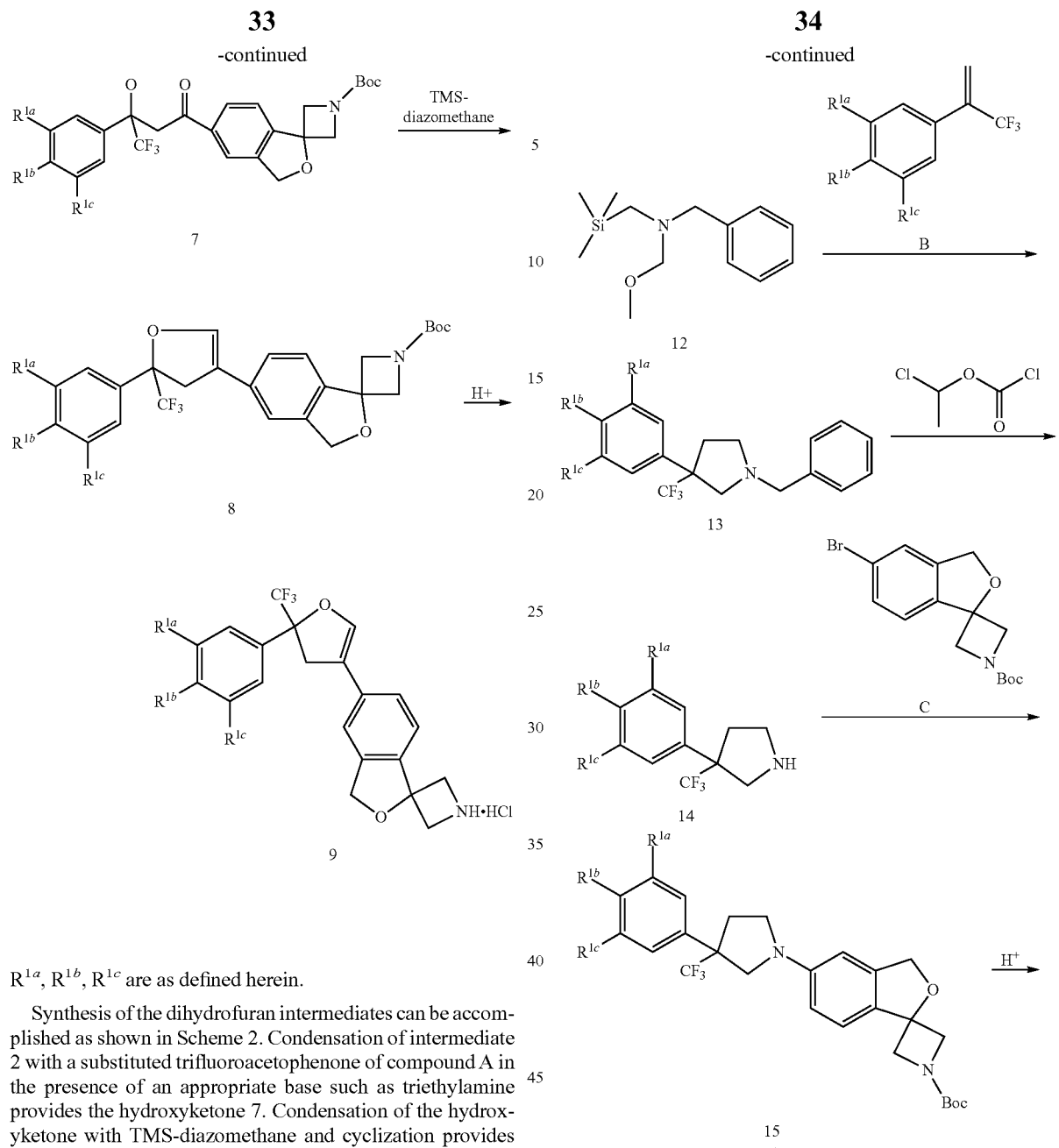

$R^{1a}$, $R^{1b}$, $R^{1c}$ are as defined herein.

Synthesis of the dihydrofuran intermediates can be accomplished as shown in Scheme 2. Condensation of intermediate 2 with a substituted trifluoroacetophenone of compound A in the presence of an appropriate base such as triethylamine provides the hydroxyketone 7. Condensation of the hydroxyketone with TMS-diazomethane and cyclization provides the dihydrofuran 8. Deprotection of the Boc group under acidic conditions such as HCl/MeOH or trifluoroacetic acid provides the desired spiroazetidine dihydrofuran intermediates 9.

Scheme 3: synthesis of pyrrolidines

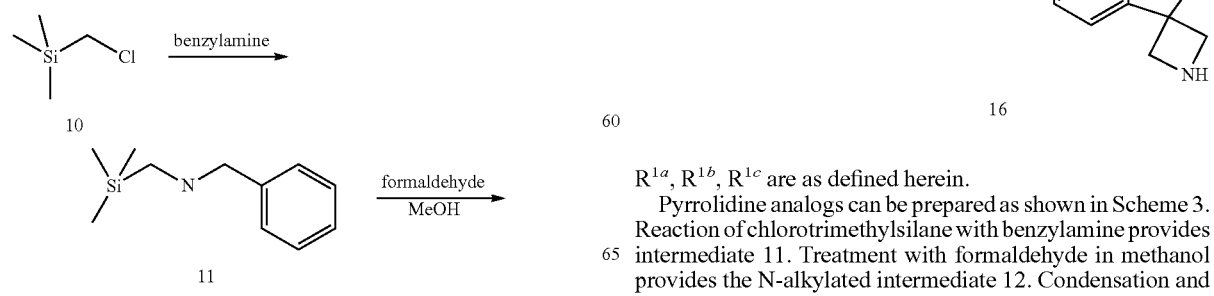

$R^{1a}$, $R^{1b}$, $R^{1c}$ are as defined herein.

Pyrrolidine analogs can be prepared as shown in Scheme 3. Reaction of chlorotrimethylsilane with benzylamine provides intermediate 11. Treatment with formaldehyde in methanol provides the N-alkylated intermediate 12. Condensation and cyclization of 12 with trifluoroalkenes B provides the N-protected pyrroles 13. Removal of the benzyl group is accomplished by treatment with chloroethyl chloroformate to provide the pyrrole intermediates 14. Palladium catalyzed coupling of the pyrrole with the bromospiroazetidine C provides the N-Boc sprioazetidines 15. Removal of the Boc group can be accomplished under acidic conditions such as HCl/MeOH or trifluoroacetic acid to provide the desired spiroazetidine pyrrolidine intermediate 16.

be accomplished under acidic conditions such as HCl/MeOH or trifluoroacetic acid to provide the spiroazetidine 17. Coupling of the azetidine with an acid or acid chloride under standard amide formation conditions provides the chalcone amides 18. Condensation of these chalcones with hydrazine or substituted hydrazines and cyclization provides the spiroazetidine dihydropyrazole analogs 19.

Scheme 4: Synthesis of dihydropyrazoles

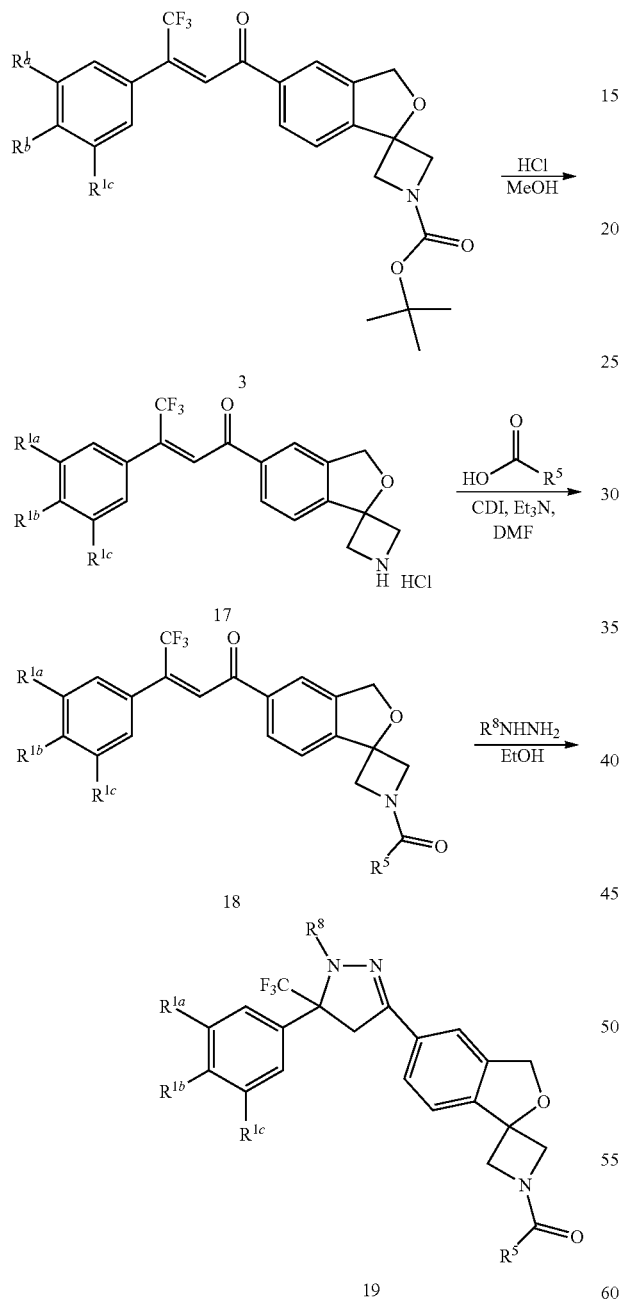

Scheme 5: Amide formation

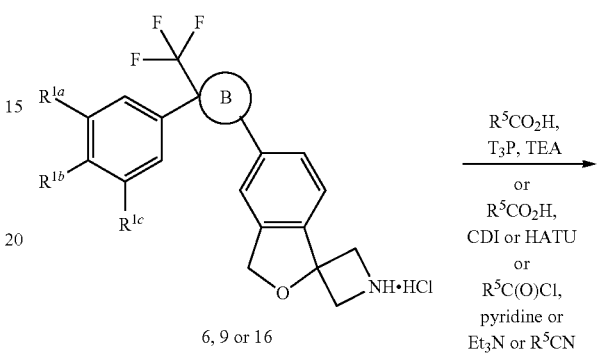

$R^{1a}$, $R^{1b}$, $R^{1c}$, $R^5$, and n are as defined herein.

Amide analogs of the azetidine ring can be prepared as shown in Scheme 5. Acylation of the azetidine ring can be accomplished by reaction of the azetidine 6, 9 or 16 with an acid chloride in pyridine/DMA or by a condensation with a carboxylic acid utilizing a condensing agent such as $T_3P$, HATU, or HOBt.

Scheme 6: Sulfonamide Formation

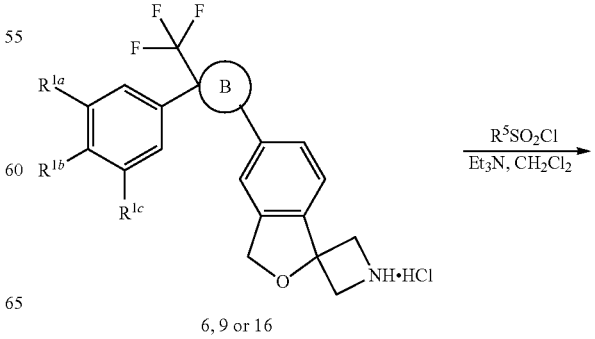

$R^{1a}$, $R^{1b}$, $R^{1c}$, $R^5$ and $R^8$ are as defined herein.

Dihydropyrazole analogs can be prepared as shown in Scheme 4. Removal of the Boc group from intermediate 3 can

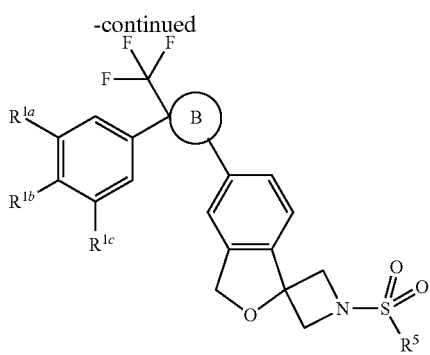

21

B, $R^{1a}$, $R^{1b}$, $R^{1c}$, and $R^5$ are as defined herein.

Sulfonamide analogs of the azetidine ring can be prepared as shown in Scheme 6. Reaction of azetidine 6, 9 or 16 with sulfonyl chlorides in the presence of triethylamine can give the desired sulfonamides.

Scheme 7: Alkylation

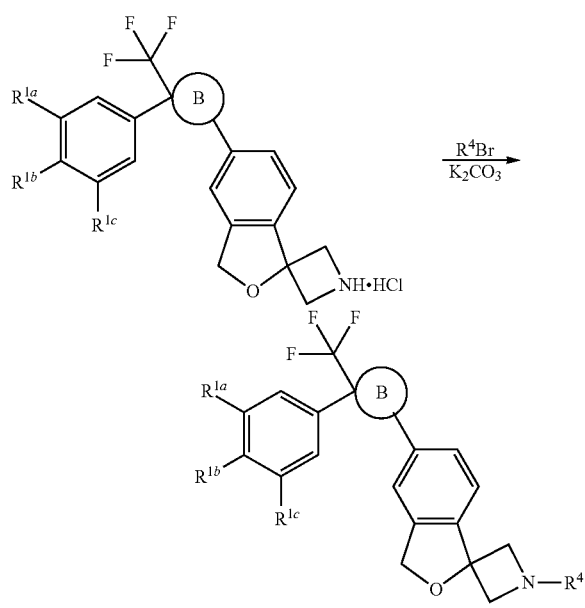

B, $R^{1a}$, $R^{1b}$, $R^{1c}$, and $R^4$ are as defined herein.

Compounds in which $R^4$ is alkyl or substituted alkyl can be prepared from the azetidines 6, 9 or 16 by standard alkylation chemistry as shown in Scheme 7 or by reductive amination with the corresponding aldehydes.

One skilled in the art will recognize that, in some cases, after the introduction of a given reagent as it is depicted in the schemes, it may be necessary to perform additional routine synthetic steps not described in detail to complete the synthesis of Formula (V.1 or V.2) compounds.

The present invention includes all veterinary acceptable isotopically-labelled Formula (V.1), (V.2), (V.1.1), (V.1.2), (V.1.3), (V.1.4), (V.1.5), and (V.1.6) compounds wherein one or more atoms are replaced by atoms having the same atomic number, but an atomic mass or mass number different from the atomic mass or mass number usually found in nature.

Examples of isotopes suitable for inclusion in the compounds of the present invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, and sulphur, such as $^{35}S$.

The skilled person will appreciate that the compounds of the present invention could be made by methods other than those herein described as incorporated herein by reference, by adaptation of the methods herein described and/or adaptation of methods known in the art, for example the art described herein, or using standard textbooks such as "Comprehensive Organic Transformations—A Guide to Functional Group Transformations", R C Larock, Wiley-VCH (1999 or later editions).

The Formula (V.1), (V.2), (V.1.1), (V.1.2), (V.1.3), (V.1.4), (V.1.5), (V.1.6), (1.2), (1.2A), (2.2), (2.2A), (3.2), (3.2A), (4.2), (4.2A), (5.2), (5.2A), (6.2), and (6.2A) compounds, stereoisomer thereof, and veterinary acceptable salts thereof, are useful as antiparasitic agents, therefore, another embodiment of the present invention is a veterinary composition comprising a therapeutically effective amount of a Formula (V.1), (V.2), (V.1.1), (V.1.2), (V.1.3), (V.1.4), (V.1.5), (V.1.6), (1.2), (1.2A), (2.2), (2.2A), (3.2), (3.2A), (4.2), (4.2A), (5.2), (5.2A), (6.2), or (6.2A) compound, stereoisomer thereof, veterinary acceptable salt thereof, and a veterinary acceptable excipient, diluent or carrier, or mixture thereof. The compounds of the present invention (including the compositions and processes used therein) may also be used in the manufacture of a medicament for the therapeutic applications described herein.

The compound of the present invention can be administered alone or in a formulation appropriate to the specific use envisaged, the particular species of host animal being treated and the parasite involved. Generally, it will be administered as a formulation in association with one or more veterinary acceptable excipients, diluents, carriers, or mixtures thereof. The term "excipient", "diluent" or "carrier" is used herein to describe any ingredient other than the compound of the present invention or any additional veterinary (e.g., antiparasitic) agent. The choice of excipient, diluent, or carrier will to a large extent depend on factors such as the particular mode of administration, the effect of the excipient, carrier, diluent, or mixture thereof, on solubility and stability, and the nature of the dosage form. In addition to the excipients, the amount of the compound of the present invention that is administered and the dosage regimen for treating a condition or disorder with the compound depends on a variety of factors, including the age, weight, sex and medical condition of the animal, the severity of the disease, the route and frequency of administration, and thus may vary widely.

In one embodiment, the veterinary and/or pharmaceutical composition comprises a Formula (V.1), (V.2), (V.1.1), (V.1.2), (V.1.3), (V.1.4), (V.1.5), (V.1.6), (1.2), (1.2A), (2.2), (2.2A), (3.2), (3.2A), (4.2), (4.2A), (5.2), (5.2A), (6.2), or (6.2A) compound, stereoisomer thereof, and veterinary acceptable salt thereof, with a carrier, diluent or excipient. The concentration range will vary depending on the composition (e.g., oral, topical, or injectable). For an oral dose, the range of active (i.e., compound of the present invention) is about 0.1 to 50 mg/kg, preferably from about 0.5 to 25 mg/kg, and even more preferably from about 0.5 to 10 mg/kg, and most preferably from about 1 to 5 mg/kg. For a topical solution, the range of active is about 0.1 to 1000 mg/mL, and preferably from about 0.5 to 500 mg/mL, and more preferably from about 1 to 250 mg/mL, and even more preferably from about 2 to 200 mg/mL. Depending upon the final volumes of the topical solution(s), the concentration of the active can change from that described above. Generally, injectable doses tend to be, but not always, lower in concentration.

The formulations can be prepared using conventional dissolution and mixing procedures. Such compositions and methods for their preparation may be found, for example, in 'Remington's Veterinary Sciences', 19th Edition (Mack Publishing Company, 1995; and "Veterinary Dosage Forms: Tablets, Vol. 1", by H. Lieberman and L. Lachman, Marcel Dekker, N.Y., 1980 (ISBN 0-8247-6918-X).

A typical formulation is prepared by mixing a Formula (V.1), (V.2), (V.1.1), (V.1.2), (V.1.3), (V.1.4), (V.1.5), (V.1.6), (1.2), (1.2A), (2.2), (2.2A), (3.2), (3.2A), (4.2), (4.2A), (5.2), (5.2A), (6.2), or (6.2A) compound, stereoisomer thereof, and veterinary acceptable salt thereof, with a carrier, diluent or excipient. Suitable excipients, carriers, and diluents are well known to those skilled in the art and include materials such as carbohydrates, waxes, water soluble and/or swellable polymers, hydrophilic or hydrophobic materials, gelatin, oils, solvents, water, and the like. The particular excipient, carrier, diluent, mixture thereof, will depend upon the means and purpose for which the compound of the present invention is being applied. Solvents are generally selected based on solvents recognized by persons skilled in the art as safe to be administered to an animal. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or veterinary composition thereof) or aid in the manufacturing of the veterinary product (i.e., medicament). The compound of the present invention will typically be formulated into veterinary dosage forms to provide an easily controllable dosage form for administration.

The methods by which the compound of the present invention can be administered include oral, topical, and injectable (e.g., parenteral and subcutaneous) administration.

The compound of the present invention can be administered orally by capsule, bolus, tablet, powders, lozenges, chews, multi and nanoparticulates, gels, solid solution, films, sprays, or liquid form. This is a preferred method of administration and as such it is desirable to develop the compound for oral administration. Such formulations may be employed as fillers in soft or hard capsules, soft or hard palatable chews, which typically comprise a carrier, for example, water, ethanol, polyethylene glycol, N-methylpyrrolidone, propylene glycol, methylcellulose, or a suitable oil, and one or more emulsifying agents, flavorants, and/or suspending agents. Liquid forms include suspensions, solutions, syrups, drenches and elixirs. Liquid formulations may also be prepared by the reconstitution of a solid, for example, from a sachet. Oral drenches are commonly prepared by dissolving or suspending the compound of the present invention in a suitable medium (e.g. triethylene glycol, benzyl alcohol, and the like). The compound of the present invention can also be formulated with a food substance, e.g., a dietary admixture (food pellets or powder for birds).

The compound of the present invention can be administered topically to the skin or mucosa, that is dermally or transdermally. This is another preferred method of administration and as such it is desirable to develop the compound of the present invention to be suited to such formulations, for example liquid forms. Typical formulations for this purpose include pour-on, spot-on, multi-spot-on, stripe-on, comb-on, roll-on, dip, spray, mousse, shampoo, powder formulation, gels, hydrogels, lotions, solutions, creams, ointments, dusting powders, dressings, foams, films, skin patches, wafers, implants, sponges, fibers, bandages and micro emulsions. Liposomes may also be used. Typical carriers include alcohol, water, mineral oil, liquid petrolatum, white petrolatum, glycerin, N-methyl formamide, glycol monomethyl ethers, polyethylene glycol, propylene glycol, and the like. Penetration enhancers may be incorporated—see, for example, *J. Pharm. Sci.*, 88(10), 955-958 by Finnin and Morgan (October 1999). Pour-on or spot-on formulations may be prepared by dissolving the active ingredients in an acceptable liquid carrier vehicle such as butyl digol, liquid paraffin or a non-volatile ester, optionally with the addition of a volatile component such as propan-2-ol or a glycol ether. Alternatively, pour-on, spot-on or spray formulations can be prepared by encapsulation, to leave a residue of active agent on the surface of the animal, this effect may ensure that the compound of the present invention has increased persistence of action and is more durable, for example it may be more water-fast. Topical formulations contemplated herein can comprise from about 0.1 mg/kg to 50 mg/kg of a compound of the present invention, and more preferably from about 1 mg/kg to 10 mg/kg of a compound of the present invention, and even more preferably, from 1 mg/kg to 5 mg/kg.

The compounds of the present invention can also be administered topically via a support matrix for example, a synthetic or natural resin, plastic, cloth, leather, or other such polymeric system in the shape of a collar or ear tag. Said collar or ear tag may be coated, impregnated, layered, by any means so as to provide a veterinary acceptable amount of a compound of the present invention alone, or with a veterinary acceptable excipient, diluent, or carrier, and optionally an additional veterinary agent, or veterinary acceptable salt thereof. Such formulations are prepared in a conventional manner in accordance with standard medicinal or veterinary practice. Further, these formulations will vary with regard to the weight of active compound contained therein, depending on the species of host animal to be treated, the severity and type of infection or infestation, and the body weight of the animal. The volume of the applied composition can be from about 0.2 mL/kg to 5 mL/kg and preferably from about 1 mL/kg to 3 mL/kg.

Agents can be added to the formulations of the present invention to improve the persistence of such formulations on the surface of the animal to which they are applied, for example to improve their persistence on the coat of the animal. It is particularly preferred to include such agents in a formulation which is to be applied as a pour-on or spot-on formulation. Examples of such agents include acrylic copolymers and in particular fluorinated acrylic copolymers. A particular suitable reagent is the trademark reagent "Foraperle" (Redline Products Inc, Texas, USA). Certain topical formulations may include unpalatable additives to minimize oral exposure.

Injectable (e.g., subcutaneous and parenteral) formulations may be prepared in the form of a sterile solution, which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending compounds of the present invention alone or with an additional veterinary agent in the liquid carrier such that the final formulation contains from about 0.01 to 30% by weight of the active ingredients.

Suitable devices for injectable administration include needle (including micro needle) injectors, needle-free injectors and infusion techniques. Injectable formulations are typically aqueous solutions which may contain excipients such as salts, carbohydrates and buffering agents (preferably to a pH of from 3 to 9), but, for some applications, they may be more suitably formulated as a sterile non-aqueous solution or as a dry powder form to be used in conjunction with a suitable vehicle such as sterile, pyrogen-free water. The preparation of injectable formulations under sterile conditions, for example, by lyophilisation, may readily be accomplished using standard veterinary techniques well known to those skilled in the art. The solubility of a compound of the present invention used in the preparation of an injectable solution may be increased by the use of appropriate formulation techniques, such as the incorporation of solubility-enhancing agents.

Administration of the compound of the instant invention is contemplated to be once a month. However, an extended duration formulation may allow for dosing once every 2, 3, 4, 5, 6, or 12 months. Dosing of the compounds of the instant invention can also be daily, weekly, or at least once every 2 weeks.

Such formulations are prepared in a conventional manner in accordance with standard medicinal or veterinary practice. Further, these formulations will vary with regard to the weight of active compound contained therein, depending on the species of host animal to be treated, the severity and type of infection or infestation, and the body weight of the animal.

The composition of the present invention may be administered alone, as described above, or in combination with at least one other additional antiparasitic agent to form a multi-component parasiticide giving an even broader spectrum of pharmaceutical and/or veterinary utility. Thus, the present invention also envisions a combination veterinary composition comprising an effective amount of the compound of the present invention in combination with at least one other additional antiparasitic agent and can further comprise at least one veterinary acceptable excipient, diluent, carrier, or mixture thereof.

The following list of additional veterinary agents together with which the compound of the present invention can be used is intended to illustrate the possible combinations, but not to impose any limitation. Non-limiting examples of additional veterinary agents include: amitraz, arylpyrazoles, amino acetonitriles, anthelmintics (e.g., albendazole, cambendazole, dichlorvos, fenbendazole, flubendazole, levamisole, mebendazole, monepantel, morantel, octadepsipeptides, oxantel, oxfendazole, oxibendazole, paraherquamide, parbendazole, piperazines, praziquantel, pyrantel, thiabendazole, tetramisole, triclabendazole, and the like), avermectins and derivatives thereof (e.g., abamectin, doramectin, emamectin, eprinomectin, ivermectin, moxidectin, selamectin, milbemycin, milbemycin oxime, and the like), DEET, demiditraz, diethylcarbamazine, fipronil, insect growth regulators (e.g., lufenuron, novaluron, hydroprene, kinoprene, methoprene, and the like), metaflumizone, niclosamide, nitenpyram, permethrin, pyrethrins, pyriproxyfen, spinosad, and the like. In certain instances, combinations of a compound of the present invention with at least one additional veterinary agent can result in a greater-than-additive effect. Non-limiting examples of combinations include, but are not limited to: compound of the present invention with pyrantel, compound of the present invention with macrocyclic lactone, combination of the present invention with macrocyclic lactone and levamisole, compound of the present invention with macrocyclic lactone and pyrantel.

The veterinary composition for application to an animal may be packaged in a variety of ways depending upon the method used for administering the compound of the present invention or combination, thereof. Generally, an article for distribution includes a container having deposited therein the veterinary composition in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The compounds of the present invention (including the compositions and processes used therein) may also be used in the manufacture of a medicament for the therapeutic applications described herein.

The compounds of the present invention, stereoisomers thereof, and compositions comprising a therapeutically effective amount of a Formula (V.1), (V.2), (V.1.1), (V.1.2), (V.1.3), (V.1.4), (V.1.5), (V.1.6), (1.2), (1.2A), (2.2), (2.2A), (3.2), (3.2A), (4.2), (4.2A), (5.2), (5.2A), (6.2), or (6.2A) compound, stereoisomer thereof, and veterinary acceptable salt thereof, and a veterinary acceptable excipient, diluent, or carrier are useful as ectoparasiticides for the control and treatment of infections or infestations manifested by said ectoparasite in an animal. The compounds of the present invention have utility as an ectoparasiticide, in particular, as an acaricide and insecticide. They may, in particular, be used in the fields of veterinary medicine, livestock husbandry and the maintenance of public health: against acarids, insects, and copepods which are parasitic upon vertebrates, particularly warm-blooded vertebrates, including companion animals, livestock, and fowl and cold-blooded vertebrates like fish. Some non-limiting examples of ectoparasites include: ticks (e.g., *Ixodes* spp., (e.g., *I. ricinus, I. hexagonus*), *Rhipicephalus* spp. (e.g., *R. sanguineus*), *Boophilus* spp., *Amblyomma* spp. (e.g., *A. maculatum, A. triste, A. parvum, A. cajennense, A. ovale, A. oblongoguttatum, A. aureolatum, A. cajennense*), *Hyalomma* spp., *Haemaphysalis* spp., *Dermacentor* spp. (e.g., *D. variabilis, D. andersoni, D. marginatus*), *Ornithodorus* spp., and the like); mites (e.g., *Dermanyssus* spp., *Sarcoptes* spp. (e.g., *S. scabiei*), *Psoroptes* spp. (e.g., *P. bovis*), *Otodectes* spp., *Chorioptes* spp., *Demodex* spp., (e.g., *D. folliculorum, D. canis*, and *D. brevis*) and the like); chewing and sucking lice (e.g., *Damalinia* spp., *Linognathus* spp., *Cheyletiella* spp., *Haematopinus* spp., *Solenoptes* spp., *Trichodectes* spp., *Felicola* spp., and the like); fleas (e.g., *Siphonaptera* spp., *Ctenocephalides* spp., and the like); biting flies, midges, and mosquitos (e.g., *Tabanidae* spp., *Haematobia* spp., *Musca* spp., *Stomoxys* spp., *Dematobia* spp., *Cochliomyia* spp., *Simuliidae* spp., *Ceratopogonidae* spp., *Psychodidae* spp., *Aedes* spp., *Culex* spp., *Anopheles* spp., and the like); bed bugs (e.g., insects within the genus *Cimex* and family Cimicidae); and grubs (e.g., *Hypoderma bovis, H. lineatum*); and copepods (e.g., sea lice within the Order Siphonostomatoida, including genera *Lepeophtheirus* and *Caligus*).

The compound of the present invention can also be used for the treatment of endoparasites, for example, helminths (e.g., trematodes, cestodes, and nematodes) including heartworm, roundworm, hookworm, whipworm, fluke, and tapeworm. The gastrointestinal roundworms include, for example, *Ostertagia ostertagi* (including inhibited larvae), *O. lyrata, Haemonchus placei, H. similis, H. contortus, Toxocara canis, T. leonina, T. cati, Trichostrongylus axei, T. colubriformis, T. longispicularis, Cooperia oncophora, C. pectinata, C. punctata, C. surnabada* (syn. *mcmasteri*), *C. spatula, Ascaris suum, Hyostrongylus rubidus, Bunostomum phlebotomum,*

*Capillaria bovis, B. trigonocephalum, Strongyloides papillosus, S. ransomi, Oesophagostomum radiatum, O. dentatum, O. columbianum, O. quadrispinulatum, Trichuris* spp., and the like. Other parasites include: hookworms (e.g., *Ancylostoma caninum, A. tubaeforme, A. braziliense, Uncinaria stenocephala*); lungworms (e.g., *Dictyocaulus viviparus* and *Metastrongylus* spp); eyeworms (e.g., *Thelazia* spp.); parasitic stage grubs (e.g., *Hypoderma bovis, H. lineatum, Dermatobia hominis*); kidneyworms (e.g., *Stephanurus dentatus*); screw worm (e.g., *Cochliomyia hominivorax* (larvae); filarial nematodes of the super-family Filarioidea and the Onchocercidae Family. Non-limiting examples of filarial nematodes within the Onchocercidae Family include the genus *Brugia* spp. (i.e., *B. malayi, B. pahangi, B. timori,* and the like), *Wuchereria* spp. (i.e., *W. bancrofti*, and the like), *Dirofilaria* spp. (*D. immitis, D. repens, D. ursi, D. tenuis, D. spectans, D. lutrae,* and the like), *Dipetalonema* spp. (i.e., *D. reconditum, D. repens*, and the like), *Onchocerca* spp. (i.e., *O. gibsoni, O. gutturosa, O. volvulus*, and the like), *Elaeophora* spp. (*E. bohmi, E. elaphi, E. poeli, E. sagitta, E. schneideri,* and the like), *Mansonella* spp. (i.e., *M. ozzardi, M. perstans*, and the like), and *Loa* spp. (i.e., *L. loa*). In another aspect of the invention, the compound of the present invention is useful for treating endoparasiticidal infection from filarial nematodes within the genus *Dirofilaria* (i.e., *D. immitis, D. repens, D. ursi, D. tenuis*, and the like).

The compounds of the present invention, and in particular, the compounds of Formula (V.1), (V.2), (V.1.1), (V.1.2), (V.1.3), (V.1.4), (V.1.5), (V.1.6), (1.2), (1.2A), (2.2), (2.2A), (3.2), (3.2A), (4.2), (4.2A), (5.2), (5.2A), (6.2), or (6.2A), stereoisomer thereof, and veterinary acceptable salt thereof, and compositions comprising compounds of the present invention in conjunction with at least one other veterinary agent are of particular value in the control of ectoparasites, endoparasites, and insects which are injurious to, or spread or act as vectors of diseases in companion animals, livestock, birds, and fish.

Any of the compounds of the present invention, or a suitable combination of a compound of the present invention and optionally, with at least one additional veterinary agent may be administered directly to the animal and/or indirectly by applying it to the local environment in which the animal dwells (such as bedding, enclosures, and the like). Direct administration includes contacting the skin, fur, or feathers of a subject animal with the compound(s), or by feeding or injecting the compounds into the animal.

The Formula (V.1), (V.2), (V.1.1), (V.1.2), (V.1.3), (V.1.4), (V.1.5), (V.1.6), (1.2), (1.2A), (2.2), (2.2A), (3.2), (3.2A), (4.2), (4.2A), (5.2), (5.2A), (6.2), or (6.2A) compound, stereoisomer thereof, and veterinary acceptable salt thereof, and combinations with at least one additional veterinary agent, as described herein, are of value for the treatment and control of the various lifecycle stages of insects and parasites including egg, nymph, larvae, juvenile and adult stages.

The present invention also relates to a method of administering a compound of the present invention alone or in combination with at least one additional veterinary agent, and optionally a veterinary acceptable excipient, diluent, or carrier, to animals in good health comprising the application to said animal to reduce or eliminate the potential for human parasitic infection or infestation from parasites carried by the animal and to improve the environment in which the animals inhabit.

The compounds of the present invention also encompass those compounds presented in Table 1, Table 2, Table 3, Table 4, Table 5, Table 6, and Table 7. A composition comprising a therapeutically acceptable amount of any of these compounds is also contemplated. The composition can further comprise a veterinary acceptable excipient, diluents, carrier, or mixture thereof. This composition can be administered to an animal in need thereof to treat a parasitic infection or infestation. The composition can further comprise an additional veterinary agent, as described herein.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed using glass-backed silica gel 60 F 254 precoated plates and eluted with appropriate solvent ratios (v/v). Reactions were assayed by TLC or VETERINARY and terminated as judged by the consumption of starting material. Visualization of the TLC plates was done with UV light (254 nM wavelength) or with an appropriate TLC visualizing solvent and activated with heat. Flash column chromatography (Still et al., *J. Org. Chem.*, 43, 2923 (1978), was performed using silica gel (RediSep Rf) or various MPLC systems, such as Biotage or ISCO purification system.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography (TLC), recrystallization, and differential (i.e., liquid-liquid) extraction techniques.

The compound structures in the examples below were confirmed by one or more of the following methods: proton magnetic resonance spectroscopy, and mass spectroscopy. Proton magnetic resonance ($^1$H NMR) spectra were determined using a Bruker spectrometer operating at a field strength of 400 megahertz (MHz). Chemical shifts are reported in parts per million (PPM, δ) downfield from an internal tetramethylsilane standard. Mass spectra (MS) data were obtained using Agilent mass spectrometer with atmospheric pressure chemical ionization. Method: Acquity UPLC with chromatography performed on a Waters BEH C18 column (2.1×50 mm, 1.7 μm) at 50° C. The mobile phase was a binary gradient of acetonitrile (containing 0.1% trifluoroacetic acid) and water (5-100%).

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

The following examples provide a more detailed description of the process conditions for preparing compounds of the present invention. It is to be understood, however, that the invention, as fully described herein and as recited in the claims, is not intended to be limited by the details of the following schemes or modes of preparation. The (E/Z) nomenclature for each of the applicable Preparation intermediates is also contemplated.

Intermediate 1: tert-butyl 5'-bromo-3'H-spiro[azetidine-3,1'-isobenzofuran]-1-carboxylate

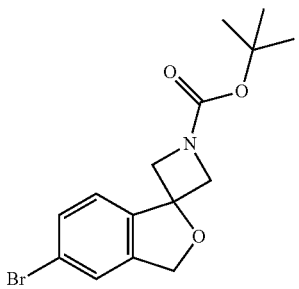 [SMILES: CC(C)(C)OC(=O)N1CC2(C1)OCc1cc(Br)ccc12]

The compound, 4-bromo-2-(chloromethyl)-1-iodobenzene (500 g, 1.509 moles) was dissolved in tetrahydrofuran (3750 mL) and cooled to −20° C. i-PrMgCl—LiCl (1.3M solution in THF) (1275 mL, 1.66 moles) was added at less than −15° C. The reaction mixture was cooled to −20° C. 3-oxo-azetidine-1-carboxylic acid, tert-butyl ester (310 g, 1.81 moles), as a solution in tetrahydrofuran (750 mL), was added. The reaction was warmed to room temperature over 90 minutes, and then stirred overnight. Aqueous citric acid solution (2 L, 1 M) was added, followed by tert-butylmethylether (2 L). The mixture was shaken. The organic phase was separated, dried over anhydrous magnesium sulphate, filtered and evaporated to dryness to give an orange oil. The oil was dissolved in ethanol (2.5 L) and the solution diluted with water (1 L). The mixture stood at room temperature, overnight. The resulting crystals of tert-butyl 5'-bromo-3'H-spiro[azetidine-3,1'-isobenzofuran]-1-carboxylate were filtered under reduced pressure and dried under vacuum at 50° C., giving 290 g.
$^1$H NMR (CDCl$_3$) δ ppm: 1.49 (9H, s), 4.15 (2H, d), 4.34 (2H, d), 5.11 (2H, s), 7.38 (2H, m), 7.56 (1H, d).

Preparation 1: tert-butyl 5'-acetyl-3'H-spiro[azetidine-3,1'-isobenzofuran]-1-carboxylate

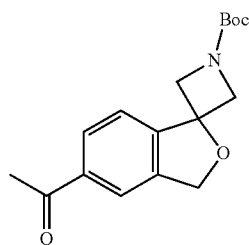 [SMILES: CC(=O)c1ccc2c(c1)COC21CN(C(=O)OC(C)(C)C)C1]

In 100 mL autoclave vessel a solution of tert-butyl 5'-bromo-3'H-spiro[azetidine-3,1'-isobenzofuran]-1-carboxylate (Intermediate 1, 10 g, 29.4 mmol) in ethanol (35 mL) was degassed with nitrogen gas for 30 minutes. To the resulting reaction mixture was added TEA (7.37 mL, 52.9 mmol), butyl vinyl ether (7.60 mL, 58.8 mmol), dppp (0.727 g, 1.8 mmol) followed by addition of Pd(OAc)$_2$ (0.198 g, 0.9 mmol) at room temperature. Reaction mixture was heated at 96° C. for 16 hours in autoclave. After complete consumption of starting material, reaction mixture was quenched with addition of 1N HCl (10 mL) to adjust pH 2-3 then reaction mixture was stirred for 2 hours. The pH of reaction mixture was adjusted to 7 by addition of saturated NaHCO$_3$ solution and extracted with ethyl acetate (3×100 mL). Combined organic layers were washed with brine (250 mL), dried over sodium sulfate and concentrated under reduced pressure to get crude compound as dark brown sticky oil 12 g as crude material. The crude was purified by column chromatography on silica gel using 230-400 silica mesh. Desired compound was eluted in 30% ethyl acetate in n-hexane to give (8.4 g) compound as off white sticky semi-solid. $^1$H NMR (400 MHz, CDCl$_3$) δ: 1.47 (s, 9H), 2.61 (s, 3H), 4.13 (d, J=9.64 Hz, 2H), 4.32 (d, J=9.52 Hz, 2H), 5.14 (s, 2H), 7.54 (d, J=7.96 Hz, 1H), 7.80 (s, 1H), 7.97 (d, J=7.92 Hz, 1H); VETERINARY (m/z): 304.0 (M+H).

Preparation 2: tert-butyl 5'-(4,4,4-trifluoro-3-(3,4,5-trichlorophenyl)but-2-enoyl)-3'H-spiro[azetidine-3,1'-isobenzofuran]-1-carboxylate

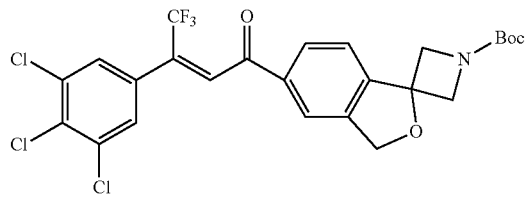 [SMILES: CC(C)(C)OC(=O)N1CC2(C1)OCc1cc(C(=O)/C=C(/c3cc(Cl)c(Cl)c(Cl)c3)C(F)(F)F)ccc12]

In 100 mL two neck RBF fitted with dean-stark apparatus, a stirred solution of tert-butyl 5'-acetyl-3'H-spiro[azetidine-3,1'-isobenzofuran]-1-carboxylate (Preparation 1, 7 g, 23.1mmol) in toluene (21 mL) and trifluoro methyl benzene (21 mL) was added followed by addition of 2,2,2-trifluoro-1-(3,4,5-trichlorophenyl)ethanone (7.37 g, 26.6 mmol) and Cs$_2$CO$_3$ (0.751 g, 2.31 mmol) at room temperature. Resulting reaction mixture was stirred at 110° C. for 16 hours. Reaction was monitored by TLC, after complete consumption of starting material; reaction mixture was dissolved in tert-butyl methyl ether (50 mL), and filtered through celite bed. The filtrate was concentrated under reduced pressure to get crude compound as brown sticky oil 14.1 g. Purification was done by column chromatography using silica gel 230-400 mesh. Desired compound was eluted in 20% ethyl acetate in n-hexane to give compound as light yellow solid (8.6 g, 66.15%). $^1$H NMR (400 MHz, CDCl$_3$) δ: 1.47 (s, 9H), 4.11 (d, J=9.6 Hz, 2H), 4.32 (d, J=9.52 Hz, 2H), 5.12 (s, 2H), 7.28 (s, 1H), 7.40 (m, 1H), 7.54-7.56 (m, 1H), 7.66 (s, 1H), 7.83 (d, J=7.92 Hz, 1H). VETERINARY (m/z): 560.0 (M−H).

Preparation 3: tert-butyl 5'-(4,4,4-trifluoro-3-(nitromethyl)-3-(3,4,5-trichlorophenyl)butanoyl)-3'H-spiro[azetidine-3,1'-isobenzofuran]-1-carboxylate

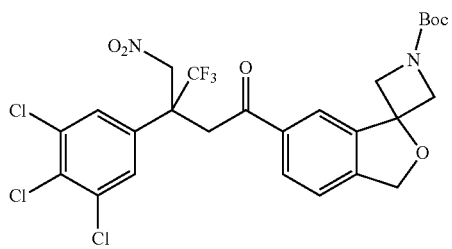 [SMILES: CC(C)(C)OC(=O)N1CC2(C1)OCc1ccc(C(=O)CC(C[N+](=O)[O-])(c3cc(Cl)c(Cl)c(Cl)c3)C(F)(F)F)cc12]

To the stirred solution of tert-butyl 5'-(4,4,4-trifluoro-3-(3,4,5-trichlorophenyl)but-2-enoyl)-3'H-spiro[azetidine-3,1'-isobenzofuran]-1-carboxylate (Preparation 2, 8.6 g, 15.33mmol) in DMF (215 mL) was added nitro methane (8.20 mL, 153.29mmol) and DBU (2.22 mL, 14.87 mmol) at room temperature. Reaction mixture was stirred at room temperature for 16 hours. After complete consumption of starting material, the reaction mixture was quenched with addition of water (250 mL) and extracted with ethyl acetate (2×300 mL). Combined organic layer was washed with LiCl Solution (2×400 mL) and brine (500 mL). Organic layer was dried over sodium sulfate and concentrated to get crude compound sticky solid (11.23 g). Purification was done by column chromatography using silica gel (230-400 mesh). Desired compound was eluted in 10% ethyl acetate in n-hexane to afford light yellow sticky liquid (5.10 g, impure-used as such in next step). $^1$H NMR (400 MHz, CDCl$_3$) δ: 1.48 (s, 9H), 3.95 (d, J=18.72 Hz, 1H), 4.13-4.18 (m, 3H), 4.33-4.36 (m, 2H), 5.17-5.18 (m, 2H), 5.42 (d, J=12.2 Hz, 1H), 5.58 (d, J=12.16 Hz, 1H), 7.20 (s, 1H), 7.31 (s, 1H), 7.60-7.65 (m 1H), 7.78 (d, J=16.92 Hz, 1H), 7.98-8.00 (m, 1H). LC-MS (m/z): 622.9 (M−H).

Preparation 4: tert-butyl 5'-(3-(3,4,5-trichlorophenyl)-3-(trifluoromethyl)-3,4-dihydro-2H-pyrrol-5-yl)-3'H-spiro[azetidine-3,1'-isobenzofuran]-1-carboxylate

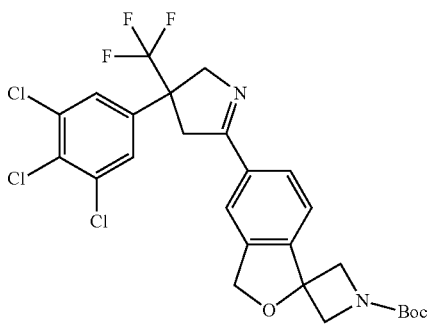 [SMILES: CC(C)(C)OC(=O)N1CC2(C1)OCc1cc(C3=NCC(c4cc(Cl)c(Cl)c(Cl)c4)(C(F)(F)F)C3)ccc12]

A solution of tert-butyl 5'-(4,4,4-trifluoro-3-(nitromethyl)-3-(3,4,5-trichlorophenyl)butanoyl)-3'H-spiro[azetidine-3,1'-isobenzofuran]-1-carboxylate (Preparation 3, 5.1 g, 8.97 mmol) in ethanol (51 mL) was purged with nitrogen gas for 30 minutes. To this reaction mixture was added pre-washed Raney Nickel (1.22 g, 50% suspension in water). Reaction mixture was stirred under hydrogen atmosphere using balloon for 16 hours at room temperature. Progress of the reaction was monitored by TLC. After consumption of intermediate-4, reaction mixture was filtered through celite bed, the bed was washed with 10% MeOH in DCM (30 mL). The filtrate was concentrated to get 4 g off white solid as crude mass, crude was purified by column chromatography on silica gel using 230-400 silica mesh. Desired product was eluted in 8% ethyl acetate in n-Hexane to get 1.6 g off white semi-solid as desired product and 1.5 g of starting material was recovered. $^1$H NMR (400 MHz, CDCl$_3$) δ: 1.47 (s, 9H), 3.43 (d, J=17.52 Hz, 1H), 3.76-3.81 (m, 1H), 4.13 (d, J=9.64 Hz, 2H), 4.32 (d, J=9.56 Hz, 2H), 4.42 (d, J=17.12 Hz 1H), 4.87 (d, J=17.12 Hz, 1H), 5.13 (s, 2H), 7.39 (s, 2H), 7.54 (d, J=7.92 Hz, 1H), 7.73 (s, 1H), 7.83 (d, J=7.92 Hz, 1H).

Preparation 5: 5-(3-(3,4,5-trichlorophenyl)-3-(trifluoromethyl)-3,4-dihydro-2H-pyrrol-5-yl)-3'H-spiro[azetidine-3,1'-isobenzofuran]hydrochloride

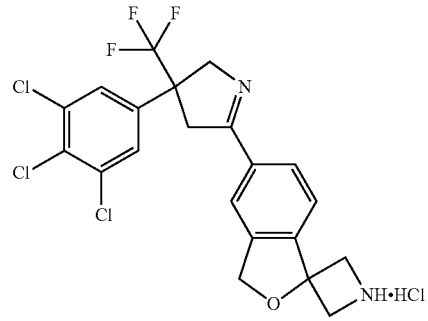

A solution of tert-butyl 5'-(3-(3,4,5-trichlorophenyl)-3-(trifluoromethyl)-3,4-dihydro-2H-pyrrol-5-yl)-3'H-spiro[azetidine-3,1'-isobenzofuran]-1-carboxylate (Preparation 4, 1.6 g, 2.79mmol) in methanol (16 mL) was purged with dry HCl gas at 0° C. for 30 minutes. Reaction was monitored by TLC, after complete consumption of starting material, reaction mixture was concentrated to remove methanol. The residue obtained was dissolved in chloroform (20 mL). Chloroform was stripped out under reduced pressure. This procedure was repeated twice to get off white solid 1.8 g crude compound in salt (HCl) form, used as such for next step. $^1$H NMR (400 MHz, DMSO-d$_6$) δ: 3.78 (d, J=16.4 Hz, 1H), 3.90 (d, J=18.56 Hz, 1H), 4.31-4.34 (m, 4H), 4.45 (d, J=17.52 Hz, 1H), 4.83 (d, J=17.04 Hz, 1H), 5.12 (s, 2H), 7.76 (d, J=6.16 Hz, 2H), 7.87 (s, 1H), 7.99-8.06 (m, 2H), 9.29 (brs, 1H), 9.52 (brs, 1H)

Example 1

2-(methylsulfonyl)-1-(5'-(3-(3,4,5-trichlorophenyl)-3-(trifluoromethyl)-3,4-dihydro-2H-pyrrol-5-yl)-3'H-spiro[azetidine-3,1'-isobenzofuran]-1-yl)ethanone

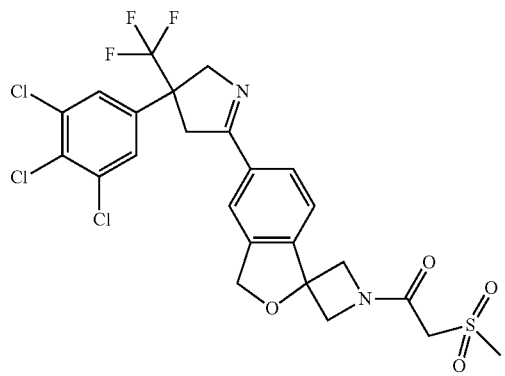

To a stirred solution of 5'-(3-(3,4,5-trichlorophenyl)-3-(trifluoromethyl)-3,4-dihydro-2H-pyrrol-5-yl)-3'H-spiro[azetidine-3,1'-isobenzofuran]hydrochloride (Preparation 5, 900 mg, 1.77 mmol) in THF (20 mL) was added DIPEA (3.01 mL, 17.65 mmol), methanesulfonyl acetic acid (488 mg, 3.53 mmol) followed by addition of T$_3$P (5.12 mL, 8.82 mmol, 50% solution in ethyl acetate) at room temperature. The resulting reaction mixture was stirred at room temperature for 16 hours. Reaction was monitored by TLC, after complete consumption of staring material reaction mixture was quenched with water (30 mL) and extracted with ethyl acetate (3×25 mL). Combined organic layer was washed with NaHCO$_3$ solution (30 mL) & brine (30 mL), dried over sodium sulphate and concentrated to get crude sticky solid 1 g. The crude was purified by column chromatography using 100-200 mesh silica gel. Desired compound was eluted in 0.5% MeOH in DCM to get desired compound as pale green solid 490 mg, 46.6%. $^1$H NMR (400 MHz, DMSO-d$_6$) δ: 3.14 (s, 3H), 3.75 (d, J=18.04 Hz, 1H), 3.88 (d, J=18.52 Hz, 1H), 4.23 (d, J=10.36 Hz, 4H), 4.44 (d, J=17.6 Hz, 1H), 4.57 (s, 2H), 4.82 (d, J=17.4 Hz, 1H), 5.10 (s, 2H), 7.66 (d, J=7.96 Hz, 1H), 7.80 (s, 2H), 7.86 (s, 1H), 7.95 (d, J=7.96 Hz, 1H). LC-MS (m/z): 594.8 (M+H).

Example 2

2-methyl-1-(5'-(3-(3,4,5-trichlorophenyl)-3-(trifluoromethyl)-3,4-dihydro-2H-pyrrol-5-yl)-3'H-spiro[azetidine-3,1'-isobenzofuran]-1-yl)propan-1-one

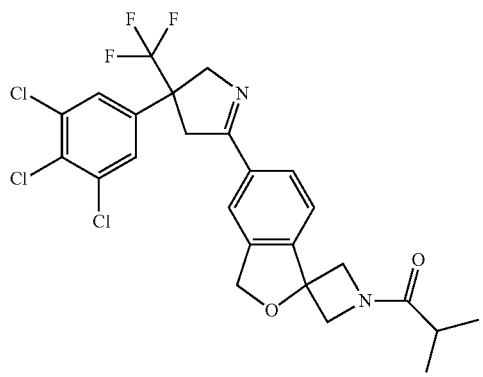 [SMILES: CC(C)C(=O)N1CC2(C1)OCc1cc(C3=NCC(c4cc(Cl)c(Cl)c(Cl)c4)(C(F)(F)F)C3)ccc12]

To a stirred solution of 5'-(3-(3,4,5-trichlorophenyl)-3-(trifluoromethyl)-3,4-dihydro-2H-pyrrol-5-yl)-3'H-spiro[azetidine-3,1'-isobenzofuran]hydrochloride (Preparation 5, 900 mg, 1.76 mmol) in THF (20 mL) was added DIPEA (3.07 mL, 17.65 mmol), isobutyric acid (0.321 mL, 3.53 mmol) and T$_3$P (5.12 mL, 8.82 mmol, 50% solution in ethyl acetate) at room temperature. The resulting reaction mixture was stirred at room temperature for 16 hours. Reaction was monitored by TLC, after complete consumption of staring material reaction mixture was quenched with water (30 mL) and extracted with ethyl acetate (3×25 mL). Combined organic layer was washed with NaHCO$_3$ solution (30 mL), brine (30 mL), dried over sodium sulphate and concentrated to get sticky solid (1 g, crude). The crude was purified by column chromatography using 100-200 mesh silica gel. Desired compound was eluted in 0.5% MeOH in DCM to get desired compound as pale green solid (0.4 g, 41.5%). $^1$H NMR (400 MHz, DMSO-d$_6$) δ: 1.01-1.05 (m, 6H), 2.54-2.75 (m, 1H), 3.74 (d, J=17.8 Hz, 1H), 3.87 (d, J=17.92 Hz, 1H), 4.12 (s, 2H), 4.41-4.46 (m, 3H), 4.82 (d, J=17.36 Hz, 1H), 5.12 (s, 2H), 7.66 (d, J=7.96 Hz, 1H), 7.80 (s, 2H), 7.85 (s, 1H), 7.94 (d, J=7.92 Hz, 1H), LC-MS (m/z): 545.0 (M+H).

Preparation 6: tert-butyl 5'-(3-(3,5-dichloro-4-fluorophenyl)-4,4,4-trifluorobut-2-enoyl)-3'H-spiro[azetidine-3,1'-isobenzofuran]-1-carboxylate

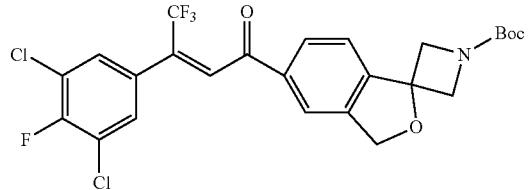 [SMILES: CC(C)(C)OC(=O)N1CC2(C1)OCc1cc(C(=O)/C=C(/c3cc(Cl)c(F)c(Cl)c3)C(F)(F)F)ccc12]

In 100 mL two neck RBF equipped with dean-stark apparatus a stirred solution of tert-butyl 5'-acetyl-3'H-spiro[azetidine-3,1'-isobenzofuran]-1-carboxylate (Preparation 1, 4.5 g, 14.851 mmol) in toluene (13.5 mL) and trifluorotoluene (13.5 mL) was added 2,2,2-trifluoro-1-(3,4,5-trichlorophenyl)-ethanone (4.44 g, 17.079 mmol) and Cs$_2$CO$_3$ (0.483 g, 1.485 mmol) at room temperature. Resulting reaction mixture was heated at 110° C. for 16 hours. After complete consumption of starting material, reaction mixture was diluted with ter-butylmethyl ether (30 mL) and filtered through celite bed. Filtrate was concentrated under vacuum to afford brown sticky oil (9.01 g, crude). Crude compound was purified by column chromatography using silica gel (230-400 mesh). Desired compound was eluted in 20% ethyl acetate in n-hexane to give light yellow solid (6.54 g, 80.64%). $^1$H NMR (400 MHz, CDCl$_3$) δ: 1.47 (s, 9H), 4.10 (d, J=9.52 Hz, 2H), 4.32 (d, J=9.36 Hz, 2H), 5.12 (s, 2H), 7.20 (d, J=9.76 Hz, 2H), 7.39 (s, 1H), 7.56 (d, J=7.96 Hz, 1H), 7.67 (s, 1H), 7.84 (d, J=7.96 Hz, 1H). LC-MS (m/z): 374.1 (M+H).

Preparation 7: tert-butyl 5'-(3-(3,5-dichloro-4-fluorophenyl)-4,4,4-trifluoro-3-(nitromethyl)butanoyl)-3'H-spiro[azetidine-3,1'-isobenzofuran]-1-carboxylate

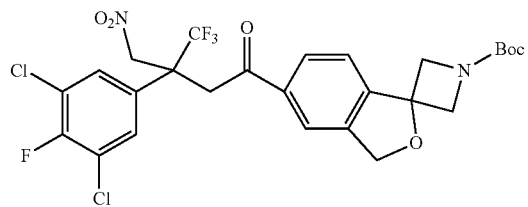 [SMILES: CC(C)(C)OC(=O)N1CC2(C1)OCc1cc(C(=O)CC(C[N+](=O)[O-])(c3cc(Cl)c(F)c(Cl)c3)C(F)(F)F)ccc12]

To a stirred solution of tert-butyl 5'-(3-(3,5-dichloro-4-fluorophenyl)-4,4,4-trifluorobut-2-enoyl)-3'H-spiro[azetidine-3,1'-isobenzofuran]-1-carboxylate (Preparation 6, 6.54 g, 11.658 mmol) in DMF (215 mL) was added nitromethane (6.24 mL, 116.57 mmol) and DBU (1.69 mL, 11.3mmol) at room temperature. Resulting reaction mixture was stirred at room temperature for 16 hours. After complete consumption of starting material, reaction mixture was quenched with water (250 mL) and extracted with ethyl acetate (2×300 mL). Combined organic layer was washed with aqueous LiCl solution (2×400 mL) then brine (500 mL), dried over sodium sulfate and concentrated to get as semi solid (11.23 g, crude). Crude compound was purified by column chromatography using silica gel (230-400 mesh). Desired compound was eluted in 10% ethyl acetate in n-hexane to afford light yellow sticky liquid (4.51 g, 63.7%). $^1$H NMR (400 MHz, CDCl$_3$) δ:

1.48 (s, 9H), 1.85-1.88 (m, 1H), 2.16-2.17 (m, 1H), 3.40-3.44 (m, 1H), 3.95 (d, J=18.84 Hz, 1H), 4.13-4.18 (m, 2H), 4.33-4.36 (m, 2H), 5.17 (d, J=4.12 Hz, 2H), 7.13 (d, J=6 Hz, 1H), 7.26 (s, 1H), 7.63-7.65 (m, 1H), 7.76-7.78 (m, 1H), 8.00-8.02 (m, 1H). LC-MS (m/z): 605.0 (M−H).

Preparation 8: tert-butyl 5'-(3-(3,5-dichloro-4-fluorophenyl)-3-(trifluoromethyl)-3,4-di hydro-2H-pyrrol-5-yl)-3'H-spiro[azetidine-3,1'-isobenzofuran]-1-carboxylate

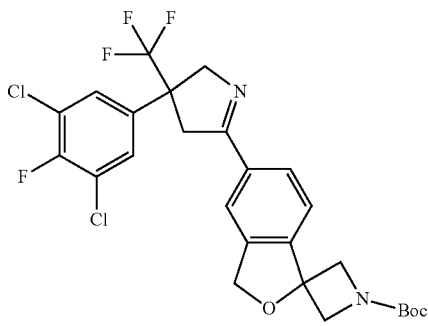 [SMILES: CC(C)(C)OC(=O)N1CC2(C1)OCc1cc(C3=NCC(c4cc(Cl)c(F)c(Cl)c4)(C(F)(F)F)C3)ccc12]

To the solution of tert-butyl 5'-(3-(3,5-dichloro-4-fluorophenyl)-4,4,4-trifluoro-3-(nitromethyl)butanoyl)-3'H-spiro[azetidine-3,1'-isobenzofuran]-1-carboxylate (Preparation 7, 1.2 g, 1.98mmol) in ethanol (10 mL) nitrogen was purged for 30 minutes and was added pre-washed Raney-Nickel (0.24 g, 50% suspension in water). Resulting reaction mixture was stirred under hydrogen atmosphere using balloon for 16 hours at room temperature. After complete conversion of starting material, the reaction mixture was filtered through celite bed. The bed was washed with 10% MeOH in DCM (30 mL). Combined filtrate was concentrated under vacuum to get 1.1 g of crude, off white solid. Crude compound was purified by column chromatography on silica gel (230-400 mesh). Desired compound was eluted in 7% EtOAc in n-Hexane to afford off white semi solid (451 mg, 40.63%). $^1$H NMR (400 MHz, CDCl$_3$) δ: 1.47 (s, 9H), 3.44 (d, J=17.2 Hz 1H), 3.76-3.81 (m, 1H), 4.13 (d, J=9.68 Hz, 2H), 4.32 (d, J=9.68 Hz, 2H), 4.42 (d, J=17.12 Hz 1H), 4.84-4.89 (m, 1H), 5.13 (s, 2H), 7.32 (d, J=5.96 Hz, 2H), 7.54 (d, J=7.92 Hz 1H), 7.73 (s, 1H), 7.83 (d, J=7.88 Hz 1H). LC-MS (m/z): 558.8 (M+H).

Preparation 9: 5-(3-(3,5-dichloro-4-fluorophenyl)-3-(trifluoromethyl)-3,4-dihydro-2H-pyrrol-5-yl)-3'H-spiro[azetidine-3,1'-isobenzofuran]hydrochloride

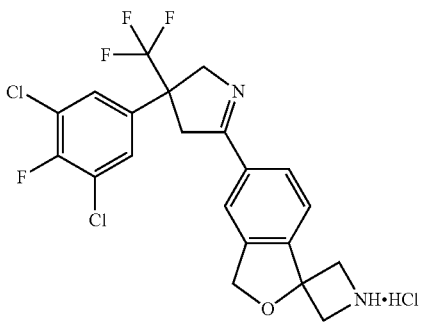

To a solution of tert-butyl 5'-(3-(3,5-dichloro-4-fluorophenyl)-3-(trifluoromethyl)-3,4-dihydro-2H-pyrrol-5-yl)-3'H-spiro[azetidine-3,1'-isobenzofuran]-1-carboxylate (Preparation 8, 0.451 g, 0.81 mmol) in methanol (13.5 mL) was purged dry HCl gas at 0° C. for 30 minutes. After complete conversion of starting material, the reaction mixture was concentrated under reduced pressure and stripped out with chloroform (15 mL). This procedure was repeated twice to get off white solid (430 mg, crude, HCl salt), used as such in next step. $^1$H NMR (400 MHz, DMSO-d$_6$) δ: 3.76-3.81 (m, 1H), 3.91 (d, J=18.24 Hz 1H), 4.28-4.34 (m, 4H), 4.46 (d, J=17.16 Hz, 1H), 4.83 (d, J=17.56 Hz 1H), 5.12 (s, 2H), 7.76 (d, J=6.16 Hz, 2H), 7.87 (s, 1H), 8.01 (d, J=8.24 Hz 1H), 8.06-8.08 (m, 1H), 9.33 (br s 1H), 9.5 (br s 1H). LC-MS (m/z): 458.8 (M+H).

Example 3

1-(5'-(3-(3,5-dichloro-4-fluorophenyl)-3-(trifluoromethyl)-3,4-dihydro-2H-pyrrol-5-yl)-3'H-spiro[azetidine-3,1'-isobenzofuran]-1-yl)-2-(methylsulfonyl)ethanone

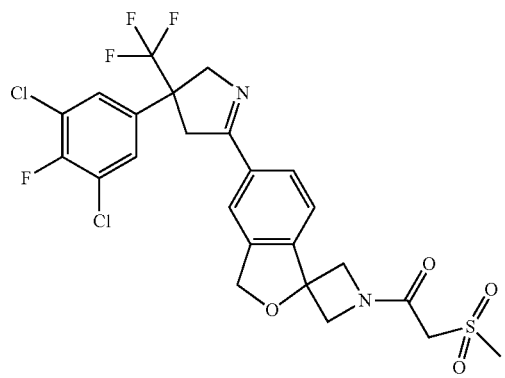 [SMILES: CS(=O)(=O)CC(=O)N1CC2(C1)OCc1cc(C3=NCC(c4cc(Cl)c(F)c(Cl)c4)(C(F)(F)F)C3)ccc12]

To a stirred solution of 5'-(3-(3,5-dichloro-4-fluorophenyl)-3-(trifluoromethyl)-3,4-dihydro-2H-pyrrol-5-yl)-3'H-spiro[azetidine-3,1'-isobenzofuran]hydrochloride (Preparation 9, 0.43 g, 0.87mmol) in THF (10 mL) was added TEA (1.20 mL, 8.67 mmol). Methane sulfonyl acetic acid (0.239 g, 1.74mmol) and T$_3$P (2.74 mL, 4.34mmol) were added at room temperature. Resulting reaction mixture was stirred at room temperature for 16 hours. After complete conversion of starting material, reaction mixture was quenched with water (10 mL) and extracted with ethyl acetate (3×10 mL). Combined organic layer was washed with brine (30 mL), dried over sodium sulfate and concentrated to get brown semi solid (0.46 g, crude). Crude compound was purified by column chromatography using Combiflash (redisep column, 12 g). Desired compound was eluted in 60% ethyl acetate in n-hexane to get off white solid (0.23 g. Impure). About 0.23 g was re-purified by preparative TLC to afford white solid (0.18 g). Compound was triturated with chloroform and n-Hexane and washed with distilled n-Hexane to get white solid (0.13 g, 25.9%). $^1$H NMR (400 MHz, CDCl$_3$) δ: 3.19 (s, 3H), 3.43 (d, J=17.44 Hz, 1H), 3.78 (d, J=17.44 Hz, 1H), 3.86 (s, 2H), 4.34-4.46 (m, 3H), 4.64-4.69 (m, 2H), 4.87 (d, J=16.96 Hz, 1H), 5.16 (s, 2H), 7.32 (d, J=5.88 Hz, 2H), 7.58 (d, J=7.92 Hz, 1H), 7.77 (s, 1H), 7.83 (d, J=7.96 Hz, 1H), LC-MS (m/z): 576.9 (M−H).

Example 4

1-(5'-(3-(3,5-dichloro-4-fluorophenyl)-3-(trifluoromethyl)-3,4-dihydro-2H-pyrrol-5-yl)-3'H-spiro[azetidine-3,1'-isobenzofuran]-1-yl)-2-methyl propan-1-one

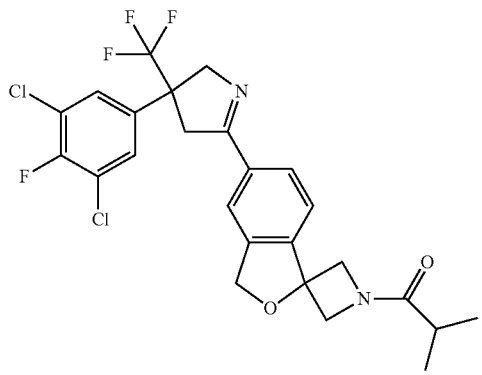 [SMILES: CC(C)C(=O)N1CC2(C1)OCc1cc(C3=NCC(c4cc(Cl)c(F)c(Cl)c4)(C(F)(F)F)C3)ccc12]

To a stirred solution of 5'-(3-(3,5-dichloro-4-fluorophenyl)-3-(trifluoromethyl)-3,4-dihydro-2H-pyrrol-5-yl)-3'H-spiro[azetidine-3,1'-isobenzofuran]hydrochloride (Preparation 9, 1 g, 2.02 mmol) in THF (20 mL) was added DIPEA (3.53 mL, 20.24 mmol), isobutyric acid (0.368 g, 4.05 mmol) and T$_3$P (2.94 mL, 10.12 mmol, 5 eq) at room temperature. Resulting reaction mixture was stirred at room temperature for 16 hours. After complete conversion of starting material, reaction mixture was quenched with water (30 mL) and extracted with ethyl acetate (3×30 mL). Combined organic layer was washed with sodium bicarbonate solution (35 mL), brine (35 mL), dried over sodium sulfate and concentrated to get brown semi solid (1.1 g, crude). Crude compound was purified by column chromatography using 100-200 mesh silica gel. Desired compound was eluted in 0.5% methanol in dichloromethane to get pale green solid (0.45 g). $^1$H NMR (400 MHz, DMSO-d$_6$) δ: 1.01-1.05 (m, 6H), 2.54-2.57 (m, 1H), 3.74 (d, J=18.12 Hz, 1H), 3.86 (d, J=18.08 Hz, 1H), 4.12 (s, 2H), 4.41-4.45 (m, 3H), 4.81 (d, J=17.36 Hz, 1H), 5.12 (s, 2H), 7.66 (d, J=7.96 Hz, 1H), 7.76 (d, J=6.24 Hz, 2H), 7.85 (s, 1H), 7.93 (d, J=7.88 Hz, 1H), LC-MS (m/z): 529.1 (M+H), Preparation 10: tert-butyl 5'-(3-(3,5-dichlorophenyl)-4,4,4-trifluorobut-2-enoyl)-3'H-spiro[azetidine-3,1'-isobenzofuran]-1-carboxylate

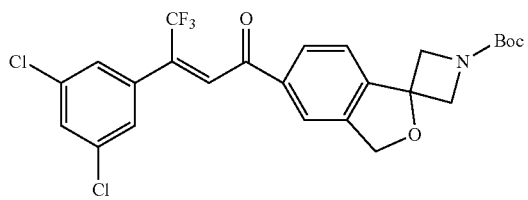 [SMILES: CC(C)(C)OC(=O)N1CC2(C1)OCc1cc(C(=O)/C=C(/c3cc(Cl)cc(Cl)c3)C(F)(F)F)ccc12]

In 100 mL two neck RBF equipped with dean-stark apparatus, the stirred solution of tert-butyl 5'-acetyl-3'H-spiro[azetidine-3,1'-isobenzofuran]-1-carboxylate (Preparation 1, 6.65 g, 21.95 mmol) in toluene (20 mL) and trifluorotoluene (20 mL) was added 1-(3,5-dichloro-phenyl)-2,2,2-trifluoroethanone (6.133 g, 25.24 mmol) and Cs$_2$CO$_3$ (0.71 g, 2.20 mmol) at room temperature. Resulting reaction mixture was stirred at 110° C. for 16 hours. After complete consumption of starting material, the reaction mixture was diluted with tert-butylmethyl ether (60 mL) and filtered through celite bed. Filtrate was concentrated to get as brown sticky oil (7.2 g, crude). Crude compound was purified by column chromatography using silica gel (230-400 mesh). Desired compound was eluted in 20% ethyl acetate in n-hexane to give light yellow solid (5.1 g, 43.97%). LC-MS (m/z): 525.9 (M−H).

Preparation 11: tert-butyl 5'-(3-(3,5-dichlorophenyl)-4,4,4-trifluoro-3-(nitromethyl)butanoyl)-3'H-spiro[azetidine-3,1'-isobenzofuran]-1-carboxylate

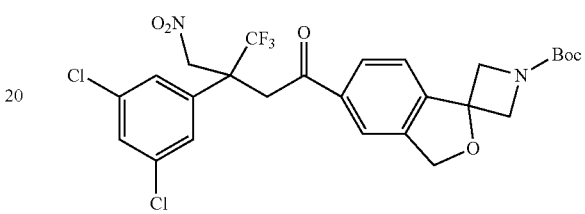

To a stirred solution of tert-butyl 5'-(3-(3,5-dichlorophenyl)-4,4,4-trifluorobut-2-enoyl)-3'H-spiro[azetidine-3,1'-isobenzofuran]-1-carboxylate (Preparation 10, 1 g, 1.89 mmol) in acetonitrile (10 mL) was added nitromethane (1.013 mL, 18.93 mmol) and DBU (0.275 mL, 1.84 mmol) at room temperature. Resulting reaction mixture was stirred at room temperature for 16 hours. After consumption of starting material; reaction mixture was quenched with water (25 mL) and extracted with ethyl acetate (2×25 mL). Combined organic layers were washed with brine (60 mL), dried over sodium sulfate and concentrated under reduced pressure to get brown semi solid (1.41 g, crude). Crude compound was purified by column chromatography using silica gel (230-400 mesh). Desired compound was eluted in 10% ethyl acetate in n-hexane to get light yellow sticky liquid (1.02 g, 91.07%). $^1$H NMR (400 MHz, CDCl$_3$) δ: 1.47 (s, 9H), 3.97 (d, J=18.64 Hz, 1H), 4.10-4.17 (m, 3H), 4.34 (d, J=9.8 Hz, 2H), 5.16 (s, 2H), 5.45 (d, J=12.32 Hz, 1H), 5.58 (d, J=12.36 Hz, 1H), 7.18 (s, 2H), 7.40-7.41 (m, 1H), 7.61 (d, J=7.92 Hz, 1H), 7.81 (s, 1H), 7.98-8.00 (m, 1H), LC-MS (m/z): 587.1 (M−H).

Preparation 12: tert-butyl 5'-(3-(3,5-dichlorophenyl)-3-(trifluoromethyl)-3,4-dihydro-2H-pyrrol-5-yl)-3'H-spiro[azetidine-3,1'-isobenzofuran]-1-carboxylate

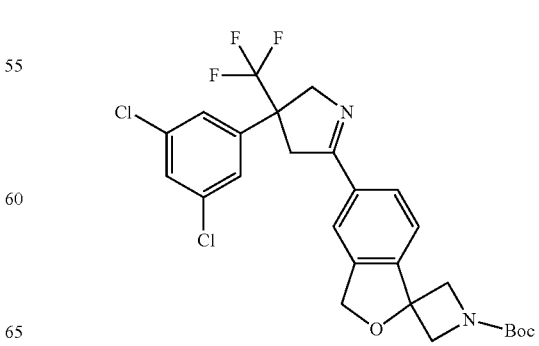

The solution of tert-butyl 5'-(3-(3,5-dichlorophenyl)-4,4,4-trifluoro-3-(nitromethyl)butanoyl)-3'H-spiro[azetidine-3,1'-isobenzofuran]-1-carboxylate) (Preparation 11, 1.02 g, 1.74 mmol) in ethanol (12 mL) was purged with nitrogen gas for 30 minutes. To this reaction mixture was added pre washed Raney-Nickel (0.24 g 50% suspension in water). Resulting reaction mixture was stirred under hydrogen atmosphere using balloon for 16 hours at room temperature. After completion of starting material, the reaction mixture was filtered through celite bed and bed was washed with 10% MeOH in DCM (30 mL). Filtrate was concentrated under reduced pressure to get off white solid 1.2 g (crude). Crude compound was purified by column chromatography on silica gel (230-400 mesh). Desired compound was eluted in 10% EtOAc in n-Hexane to get off white semi solid (0.54 g, 57.45%). $^1$H NMR (400 MHz, CDCl$_3$) δ: 1.53 (s, 9H), 3.45 (d, J=17.2 Hz, 1H), 3.76-3.81 (m, 1H), 4.10-4.14 (m, 2H), 4.32 (d, J=9.88 Hz, 2H), 4.43 (d, J=16.88 Hz, 1H), 4.85-4.90 (m, 1H), 5.13 (s, 2H), 7.25 (m, 2H), 7.36-7.37 (m, 1H), 7.54 (d, J=7.96 Hz, 1H), 7.73 (s, 1H), 7.83 (d, J=7.68 Hz, 1H), LC-MS (m/z): 540.6 (M+H)

Preparation 13: 5'-(3-(3,5-dichlorophenyl)-3-(trifluoromethyl)-3,4-dihydro-2H-pyrrol-5-yl)-3'H-spiro[azetidine-3,1'-isobenzofuran]hydrochloride

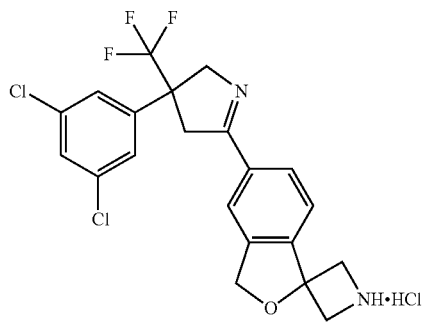

To a stirred solution of tert-butyl 5'-(3-(3,5-dichlorophenyl)-3-(trifluoromethyl)-3,4-dihydro-2H-pyrrol-5-yl)-3'H-spiro[azetidine-3,1'-isobenzofuran]-1-carboxylate (Preparation 12, 0.528 g, 0.98 mmol) in methanol (13.5 mL) was purged with dry HCl gas at 0° C. for 30 minutes. After consumption of starting material, the reaction mixture was concentrated was stripped out with chloroform (10 mL) under reduced pressure, this procedure was repeated twice to get off white solid (460 mg, crude, HCl salt). $^1$H NMR (400 MHz, DMSO-d$_6$) δ: 3.93 (d, J=18.88 Hz, 1H), 4.31-4.34 (m, 4H), 4.45 (d, J=16.76 Hz, 1H), 4.84 (d, J=17.35 Hz, 1H), 5.12 (s, 3H), 7.58 (s, 2H), 7.70-7.71 (m, 1H), 7.89 (s, 1H), 8.03 (d, J=7.84 Hz, 1H), 8.08 (d, J=8 Hz, 1H), 9.34 (bs, 1H), 9.63 (bs, 1H), LC-MS (m/z): 441.1 (M+H).

Example 5

1-(5'-(3-(3,5-dichlorophenyl)-3-(trifluoromethyl)-3,4-dihydro-2H-pyrrol-5-yl)-3'H-spiro[azetidine-3,1'-isobenzofuran]-1-yl)-2-(methylsulfonyl)ethanone

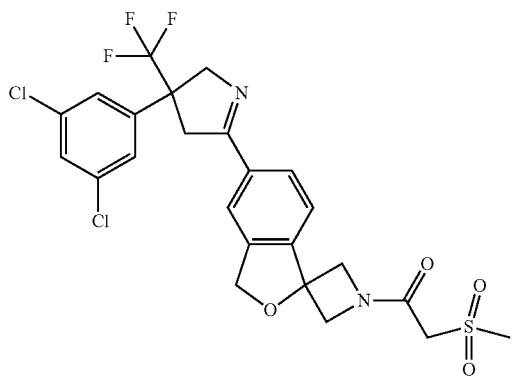 [SMILES: CS(=O)(=O)CC(=O)N1CC2(C1)OCc1cc(C3=NCC(c4cc(Cl)cc(Cl)c4)(C(F)(F)F)C3)ccc12]

To the stirred solution of 5'-(3-(3,5-dichlorophenyl)-3-(trifluoromethyl)-3,4-dihydro-2H-pyrrol-5-yl)-3'H-spiro[azetidine-3,1'-isobenzofuran]hydrochloride (Preparation 13, 0.46 g, 0.963 mmol) in DMF (10 mL) was added TEA (0.67 mL, 4.81 mmol), methane sulfonyl acetic acid (0.266 g, 1.93 mmol) followed by addition of HOBt (0.13 g, 0.96 mmol) and EDC.HCl (0.276 g, 1.44 mmol) at room temperature. Resulting reaction mixture was stirred at room temperature for 16 hours. After complete conversion of starting material, reaction mixture was quenched with water (20 mL) and extracted with ethyl acetate (3×20 mL). Combined organic layer was washed with LiCl solution (2×40 mL) and brine (2×50 mL), dried over sodium sulfate and concentrated to get brown semi solid (0.597 g, crude). Crude compound was purified by column chromatography using silica gel (230-400 mesh). Desired compound was eluted in 0.8% methanol in DCM to get off white solid (403 mg). Compound was triturated thrice with chloroform n-hexane to get pure compound as off white solid (0.24 g, 44.4%), $^1$H NMR (400 MHz, DMSO-d$_6$) δ: 3.14 (s, 3H), 3.73 (d, J=18.2 Hz, 1H), 3.87 (d, J=18.12 Hz, 1H), 4.23 (d, J=10.48 Hz, 4H), 4.42 (d, J=16.88 Hz, 1H), 4.57 (s, 2H), 4.82 (d, J=17.2 Hz, 1H), 5.13 (s, 2H), 7.57 (s, 2H), 7.65 (d, J=7.92 Hz, 1H), 7.70 (s, 1H), 7.86 (s, 1H), 7.95 (d, J=7.8 Hz, 1H), LC-MS (m/z): 561.0 (M+H), Example 6

5'-(3-(3,5-dichlorophenyl)-3-(trifluoromethyl)-3,4-dihydro-2H-pyrrol-5-yl)-1-isobutyryl-3'H-spiro[azetidine-3,1'-[2]benzofuran]

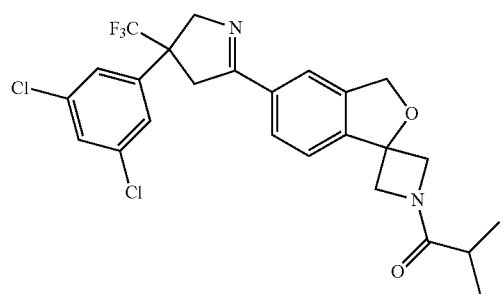 [SMILES: CC(C)C(=O)N1CC2(C1)OCc1cc(C3=NCC(c4cc(Cl)cc(Cl)c4)(C(F)(F)F)C3)ccc12]

This compound was prepared in an analogous manner to that of Example 5 except that isobutyric acid was used in place of methane sulfonyl acetic acid. $^1$H NMR (400 MHz, CDCl$_3$) δ: 1.15 (t, J=7.04 Hz, 6H), 2.48-2.53 (m, 1H), 3.45 (d, J=17.12 Hz, 1H), 3.78 (d, J=17.56 Hz, 1H), 4.26 (d, J=10.52 Hz, 1H), 4.36 (t, J=10.66 Hz, 2H), 4.43 (d, J=17.04 Hz, 1H), 4.52 (d, J=8.92 Hz, 1H), 4.88 (d, J=18.08 Hz, 1H), 5.16 (s, 2H), 7.25-7.26 (m, 2H), 7.37-7.38 (m, 1H), 7.48 (d, J=7.96 Hz, 1H), 7.76 (d, J=6.76. Hz, 1H), 7.84 (t, J=7.14 Hz, 1H). LC-MS (m/z): 510.9 (M+H).

Preparation 14: tert-butyl-5-[3-(3,5-dichlorophenyl)-4,4,4-trifluoro-3-hydroxybutyryl]-3'H-spiro[azetidine-3,1'-[2]benzofuran]1-carboxylate

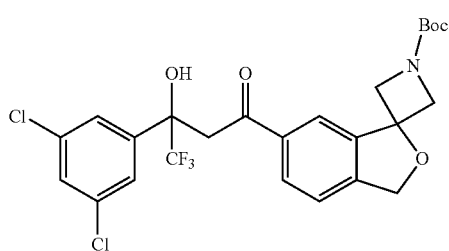 [SMILES: CC(C)(C)OC(=O)N1CC2(C1)OCc1ccc(C(=O)CC(O)(c3cc(Cl)cc(Cl)c3)C(F)(F)F)cc12]

In a clean and dry sealed tube, to a stirred solution of tert-butyl 5'-acetyl-3'H-spiro[azetidine-3,1'-isobenzofuran]-1-carboxylate (Preparation 1, 7.3 gm, 24.09 mmol) in heptane (73 mL) was added 1-(3,5-dichlorophenyl)-2,2,2-trifluroethanone (11.7 gm, 48.19 mmol) followed by addition of triethyl amine (TEA, 3.36 mL, 24.09 mmol) at room temperature. Resulting reaction mixture was heated at 60° C. for 16 hours. After maximum consumption of starting material, reaction mixture was cooled to room temperature, solid precipitated out. Solid was isolated by filtration and washed with heptane (2×70 mL) and n-pentane (70 mL) and dried under reduced pressure to get white solid (12.1 g, 91.95%). $^1$H NMR (400 MHz, CDCl$_3$) δ: 1.47 (s, 9H), 3.67 (d, J=17.36 Hz, 1H), 3.84 (d, J=17.44 Hz, 1H), 4.13 (d, J=9.6 Hz, 2H), 4.33 (d, J=9.52 Hz, 2H), 5.15 (s, 2H), 5.71 (s, 1H), 7.34 (s, 1H), 7.47 (s, 2H), 7.60 (d, J=7.96 Hz, 1H), 7.77 (s, 1H), 7.96 (d, J=7.8 Hz, 1H). LC-MS (m/z): 543.7 (M–H).

Preparation 15: tert-butyl 5'-[5-(3,5-dichlorophenyl)-5-(trifluoromethyl)-4,5-dihydrofuran-3-yl]-3'H-spiro[azetidine-3,1'-[2]benzofuran]-1-carboxylate

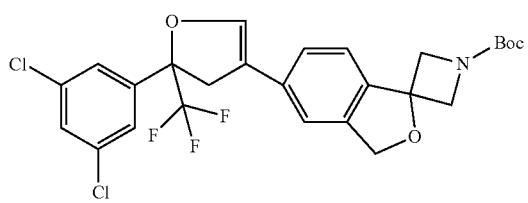 [SMILES: CC(C)(C)OC(=O)N1CC2(C1)OCc1cc(C3=COC(c4cc(Cl)cc(Cl)c4)(C(F)(F)F)C3)ccc12]

To a stirred solution of trimethylsilyldiazomethane (2M in diethyl ether, 25.62 mL, 51.24 mmol) in 1,2-dimethoxyethane (DME, 140 mL) was added methyl lithium (1.6M in diethyl ether, 32.02 mL, 51.24mmol) at −78° C. over period of 10 minutes and stirred reaction mixture for 30 minutes at −78° C. Pre-dissolved tert-butyl-5-[3-(3,5-dichlorophenyl)-4,4,4-trifluoro-3-hydroxybutyryl]-3'H-spiro[azetidine-3,1'-[2]benzofuran]1-carboxylate (Preparation 14, 7 g, 12.81 mmol) in DME (70 mL) was added at −78° C. in dropwise manner over period of 10 minutes. Resulting reaction mixture was stirred for 1 h at same temperature and then at room temperature for 2 hours. Acetic acid (2.2 mL, 38.43 mmol) was added at room temperature over period of 5 minutes followed by addition of TBAF (38.53 mL, 38.43 mmol) at room temperature over period of 10 minutes. After consumption of starting material, reaction mixture was quenched with water (200 mL) and extracted with ethyl acetate (5×200 mL). Combined organic layer was dried over sodium sulphate and concentrated in vacuo to get orange semisolid (7.5 g, crude). Crude was purified by column chromatography using 100-200 mesh silica gel. Desired compound was eluted in 10% ethyl acetate in hexane to afford off white semisolid (2.2 g, impure). Compound was again purified by column chromatography using 100-200 mesh silica gel. Desired product eluted in 10% ethyl acetate in hexane to afford off white solid (1.3 g, 18.71%). $^1$H NMR (400 MHz, CDCl$_3$) δ: 1.46 (s, 9H), 3.19 (d, J=17.2 Hz, 1H), 3.30 (d, J=17.2 Hz, 1H), 4.08 (d, J=9.68 Hz, 2H), 4.28 (d, J=9.92 Hz, 2H), 5.04 (s, 2H), 7.13 (s, 1H), 7.29 (d, J=7.68 Hz, 1H), 7.35 (d, J=7.8 Hz, 1H), 7.39-7.40 (m, 1H), 7.53 (d, J=1.4 Hz, 2H). LC-MS (m/z): 540.0 (M−H).

Preparation 16: 5'-(5-(3,5-dichlorophenyl)-5-(trifluoromethyl)-4,5-dihydrofuran-3-yl)-3'H-spiro[azetidine-3,1'-isobenzofuran]hydrochloride

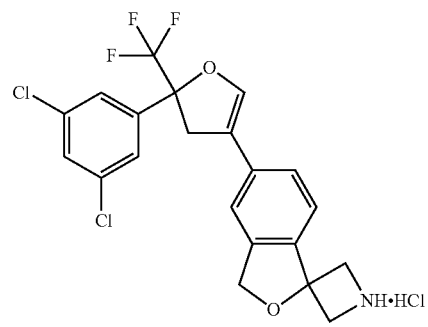

To a stirred solution of tert-butyl 5'-[5-(3,5-dichlorophenyl)-5-(trifluoromethyl)-4,5-dihydrofuran-3-yl]-3'H-spiro[azetidine-3,1'-[2]benzofuran]carboxylate (Preparation 15, 1.3 g, 2.42 mmol) in MeOH (10 mL) was purged with HCl gas for 1 hour at room temperature. After consumption of starting material, reaction mixture concentrated in vacuo to get orange semisolid (1.1 g, crude), which was triturated with n-pentane (2×5 mL) to get pale yellow solid (1.05 g, impure), used as such for next reaction. $^1$H NMR (400 MHz, DMSO-d$_6$) δ: 3.20 (d, J=17.16 Hz, 1H), 3.63 (d, J=17.16 Hz, 1H), 4.23-4.31 (m, 4H), 5.00 (s, 2H), 7.14 (s, 1H), 7.25 (d, J=7.84 Hz, 1H), 7.48 (s, 1H), 7.70-7.72 (m, 3H), 7.87 (d, J=7.88 Hz, 1H), 9.28 (bs, 1H), 9.57 (bs, 1H). LC-MS (m/z): 442.2 (M+H).

Example 7

5'-[5-(3,5-dichlorophenyl)-5-(trifluoromethyl)-4,5-dihydrofuran-3-yl]-1-[(methylsulfonyl)acetyl]-3'H-spiro[azetidine-3,1'-[2]benzofuran]

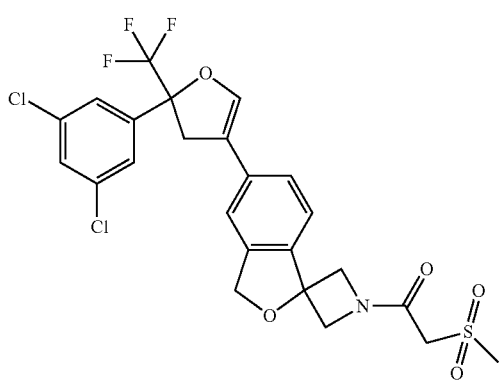 [SMILES: CS(=O)(=O)CC(=O)N1CC2(C1)OCc1cc(C3=COC(c4cc(Cl)cc(Cl)c4)(C(F)(F)F)C3)ccc12]

To a stirred solution of hydrochloride salt of 5'-[5-(3,5-dichlorophenyl)-5-(trifluoromethyl)-4,5-dihydrofuran-3-yl]-3'H-spiro[azetidine-3,1'-[2]benzofuran](Preparation 16, 0.5 g, 1.04 mmol) in THF (6 mL) was added DIPEA (1.82 mL, 10.45 mmol) at room temperature and stirred for 10 minutes at room temperature. Methane sulfonyl acetic acid (0.289 g, 2.09 mmol) and T$_3$P (50% solution in ethyl acetate, 3.1 mL, 5.22 mmol) were added at room temperature. Resulting reaction mixture was stirred for 16 hours at room temperature under nitrogen atmosphere. After complete consumption of starting material, reaction mixture was quenched with water (25 mL) and extracted with ethyl acetate (5×25 mL). Combined organic layer was washed with saturated solution of NaHCO$_3$ (2×100 mL), dried over sodium sulphate and concentrated in vacuo to get pale yellow oil (0.62 g, crude). Crude was purified by column chromatography using 100-200 mesh silica gel. Desired product gets eluted in 0.7% MeOH in DCM to afford white semisolid (0.36 g), which was triturated with DCM: n-pentane (1:10; 2×5 mL) to afford off white solid (0.295 g, 50.18%). $^1$H NMR (400 MHz, CDCl$_3$) δ: 3.17 (s, 3H), 3.21 (d, J=8.4 Hz, 1H), 3.31 (d, J=17.32 Hz, 1H), 3.84 (s, 2H), 4.31 (d, J=10.96 Hz, 1H), 4.41 (d, J=11.24 Hz, 1H), 4.58-4.64 (m, 2H), 5.08 (s, 2H), 7.15 (s, 1H), 7.33 (d, J=7.76 Hz, 1H), 7.40-7.43 (m, 2H), 7.51 (d, J=1.12 Hz, 2H). LC-MS (m/z): 559.7 (M–H).

Example 8

5'-[5-(3,5-dichlorophenyl)-5-(trifluoromethyl)-4,5-dihydrofuran-3-yl]-1-isobutyryl-3'H-spiro[azetidine-3,1'-[2]benzofuran]

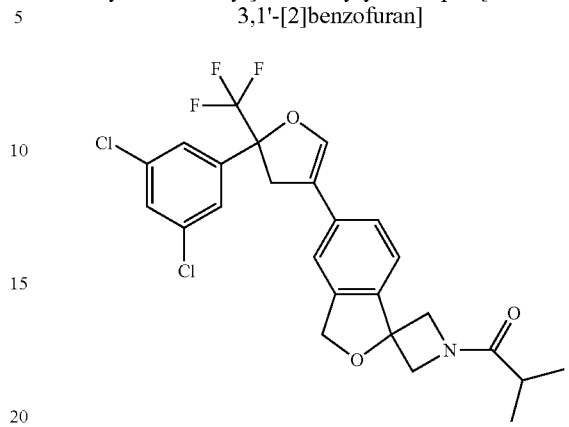

This compound was prepared in an analogous manner to that of Example 7 except that isobutyric acid was used in place of methane sulfonyl acetic acid. $^1$H NMR (400 MHz, CDCl$_3$) δ: 1.12-1.15 (m, 6H), 2.45-2.52 (m, 1H), 3.20 (d, J=17.24 Hz, 1H), 3.31 (d, J=17.24 Hz, 1H), 3.40 (d, J=2.64 Hz, 1H), 4.21 (d, J=10.64 Hz, 1H), 4.30 (q, J=11.01 Hz, 2H), 4.48 (d, J=8.96 Hz, 1H), 5.07 (s, 2H), 7.15-7.17 (m, 1H), 7.30 (s, 2H), 7.38-7.40 (m, 1H), 7.51 (d, J=0.96 Hz, 2H). LC-MS (m/z): 509.8 (M–H).

Preparation 17: tert-butyl 5'-(4,4,4-trifluoro-3-hydroxy-3-(3,4,5-trichlorophenyl)butanoyl)-3'H-spiro[azetidine-3,1'-isobenzofuran]-1-carboxylate

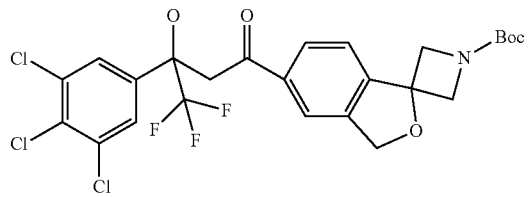

This compound was prepared in an analogous manner to that of Preparation 14 except that 2,2,2-trifluoro-1-(3,4,5-trichloro-phenyl)-ethanone was used in place of 1-(3,5-dichlorophenyl)-2,2,2-trifluroethanone. $^1$H NMR (400 MHz, CDCl$_3$) δ: 1.47 (s, 9H), 3.67 (d, J=17.36 Hz, 1H), 3.83 (d, J=17.44 Hz, 1H), 4.13 (d, J=9.6 Hz, 2H), 4.33 (d, J=9.52 Hz, 2H), 5.15 (s, 2H), 5.71 (s, 1H), 7.60-7.62 (m, 3H), 7.77 (s, 1H), 7.96 (d, J=7.88 Hz, 1H). LC-MS (m/z): 577.9 (M–H).

Preparation 18: tert-butyl 5'-[5-(3,4,5-trichlorophenyl)-5-(trifluoromethyl)-4,5-dihydrofuran-3-yl]-3'H-spiro[azetidine-3,1'-[2]benzofuran]-1-carboxylate

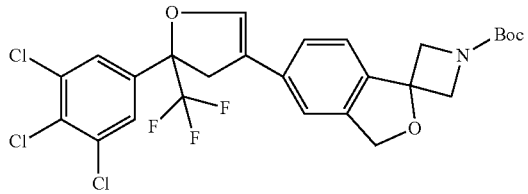 [SMILES: CC(C)(C)OC(=O)N1CC2(C1)OCc1cc(C3=COC(c4cc(Cl)c(Cl)c(Cl)c4)(C(F)(F)F)C3)ccc12]

This compound was prepared in an analogous manner to that of Preparation 15 except that tert-butyl-5-[3-(3,4,5-trichlorophenyl)-4,4,4-trifluoro-3-hydroxybutyryl]-3'H-spiro[azetidine-3,1'-[2]benzofuran]-1-carboxylate was used in place of tert-butyl-5-[3-(3,5-dichlorophenyl)-4,4,4-trifluoro-3-hydroxybutyryl]-3'H-spiro[azetidine-3,1'-[2]benzofuran]1-carboxylate. $^1$H NMR (400 MHz, CDCl$_3$) δ: 1.46 (s, 9H), 3.19 (d, J=17.2 Hz, 1H), 3.30 (d, J=17.2 Hz, 1H), 4.08 (d, J=9.68 Hz, 2H), 4.28 (d, J=9.92 Hz, 2H), 5.06 (s, 2H), 7.11 (s, 1H), 7.26-7.28 (m, 2H), 7.33 (d, J=7.84 Hz, 1H), 7.65 (s, 2H). LC-MS (m/z): 573.8 (M–H).

Preparation 19: 5'-(5-(3,4,5-trichlorophenyl)-5-(trifluoromethyl)-4,5-dihydrofuran-3-yl)-3'H-spiro[azetidine-3,1'-isobenzofuran]hydrochloride

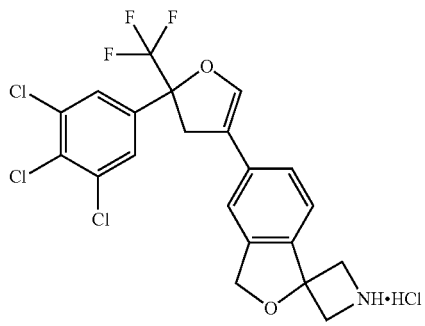

This compound was prepared in an analogous manner to that of Preparation 16 except that tert-butyl 5'-[5-(3,4,5-trichlorophenyl)-5-(trifluoromethyl)-4,5-dihydrofuran-3-yl]-3'H-spiro[azetidine-3,1'-[2]benzofuran]carboxylate was used in place of tert-butyl 5'-[5-(3,5-dichlorophenyl)-5-(trifluoromethyl)-4,5-dihydrofuran-3-yl]-3'H-spiro[azetidine-3,1'-[2]benzofuran]carboxylate. $^1$H NMR (400 MHz, DMSO-d$_6$) δ: 3.22 (d, J=17.16 Hz, 1H), 3.67 (d, J=17.16 Hz, 1H), 4.23-4.44 (m, 4H), 5.00 (s, 2H), 7.15 (s, 1H), 7.25 (d, J=7.84 Hz, 1H), 7.60 (bs, 1H), 7.87-7.95 (m, 3H), 9.40 (bs, 1H), 9.78 (bs, 1H). LC-MS (m/z): 475.9 (M+H).

Example 9

2-(methylsulfonyl)-1-(5'-(5-(3,4,5-trichlorophenyl)-5-(trifluoromethyl)-4,5-dihydrofuran-3-yl)-3'H-spiro[azetidine-3,1'-isobenzofuran]-1-yl)ethanone

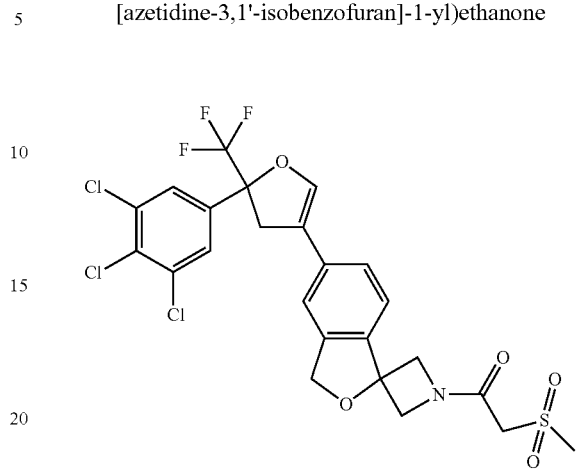

This compound was prepared in an analogous manner to that of Example 7 except that the hydrochloride salt of 5'-[5-(3,4,5-trichlorophenyl)-5-(trifluoromethyl)-4,5-dihydrofuran-3-yl]-3'H-spiro[azetidine-3,1'-[2]benzofuran] was used in place of the hydrochloride salt of 5'-[5-(3,5-dichlorophenyl)-5-(trifluoromethyl)-4,5-dihydrofuran-3-yl]-3'H-spiro[azetidine-3,1'-[2]benzofuran]. $^1$H NMR (400 MHz, CDCl$_3$) δ: 3.17 (s, 3H), 3.21-3.24 (m, 1H), 3.31 (d, J=17.32 Hz, 1H), 3.84 (s, 2H), 4.30 (d, J=11.08 Hz, 1H), 4.41 (d, J=11.12 Hz, 1H), 4.58-4.64 (m, 2H), 5.08 (s, 2H), 7.16 (s, 1H), 7.26 (s, 1H), 7.34 (d, J=7.84 Hz, 1H), 7.42 (d, J=7.8 Hz, 1H), 7.64 (s, 2H). LC-MS (m/z): 593.9 (M–H).

Example 10

1-(5'-(5-(3,4,5-trichlorophenyl)-5-(trifluoromethyl)-4,5-dihydrofuran-3-yl)-3'H-spiro[azetidine-3,1'-isobenzofuran]-1-yl)propan-1-one

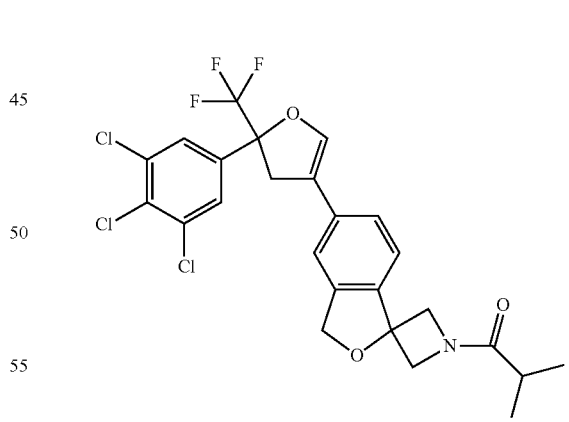

This compound was prepared in an analogous manner to that of Example 9 except that isobutyric acid was used in place of methane sulfonyl acetic acid. $^1$H NMR (400 MHz, CDCl$_3$) δ: 1.13-1.15 (m, 6H), 2.46-2.52 (m, 1H), 3.19 (d, J=17.24 Hz, 1H), 3.31 (d, J=17.24 Hz, 1H), 3.63 (d, J=5.8 Hz, 1H), 4.21 (d, J=10.64 Hz, 1H), 4.28 (d, J=9.24 Hz, 1H), 4.33 (d, J=10.76 Hz, 1H), 4.47 (d, J=9.12 Hz, 1H), 5.06 (s, 2H), 7.14 (d, J=7.72 Hz, 1H), 7.28 (d, J=3.84 Hz, 2H), 7.65 (s, 2H). LC-MS (m/z): 545.8 (M+H).

Preparation 20: tert-butyl-4-[3-(4-fluoro,3,5-dichlorophenyl)-4,4,4-trifluoro-3-hydroxybutyryl]-3'H-spiro[azetidine-3,1'-[2]benzofuran]-1-carboxylate

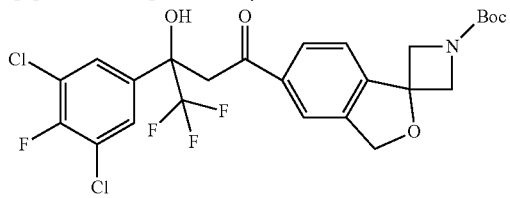

This compound was prepared in an analogous manner to that of Preparation 14 except that 1-(3,5-dichloro-4-fluorophenyl)-2,2,2-trifluoro-ethanone was used in place of 1-(3,5-dichlorophenyl)-2,2,2-trifluroethanone. $^1$H NMR (400 MHz, CDCl$_3$) δ: 1.47 (s, 9H), 3.67 (d, J=17.36 Hz, 1H), 3.82 (d, J=17.44 Hz, 1H), 4.13 (d, J=9.6 Hz, 2H), 4.33 (d, J=9.52 Hz, 2H), 5.15 (s, 2H), 5.74 (s, 1H), 7.54 (d, J=6.04 Hz, 2H), 7.61 (d, J=8.01 Hz, 1H), 7.77 (s, 1H), 7.96 (d, J=8.01 Hz, 1H). LC-MS (m/z): 561.8 (M−H).

Preparation 21: tert-butyl 5'-[5-(4-fluoro, 3,5-dichlorophenyl)-5-(trifluoromethyl)-4,5-dihydrofuran-3-yl]-3'H-spiro[azetidine-3,1'-[2]benzofuran]-1-carboxylate

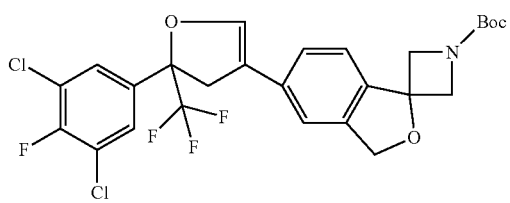 [SMILES: CC(C)(C)OC(=O)N1CC2(C1)OCc1cc(C3=COC(c4cc(Cl)c(F)c(Cl)c4)(C(F)(F)F)C3)ccc12]

This compound was prepared in an analogous manner to that of Preparation 15 except that tert-butyl-5'-[3-(4-fluoro,3,5-dichlorophenyl)-4,4,4-trifluoro-3-hydroxybutyryl]-3'H-spiro[azetidine-3,1'-[2]benzofuran]-1-carboxylate was used in place of tert-butyl 5-[3-(3,5-dichlorophenyl)-4,4,4-trifluoro-3-hydroxybutyryl]-3'H-spiro[azetidine-3,1'-[2]benzofuran]1-carboxylate. $^1$H NMR (400 MHz, CDCl$_3$) δ: 1.46 (s, 9H), 3.19 (d, J=17.2 Hz, 1H), 3.30 (d, J=17.2 Hz, 1H), 4.08 (d, J=9.68 Hz, 2H), 4.28 (d, J=9.92 Hz, 2H), 5.04 (s, 2H), 7.13 (s, 1H), 7.26 (s, 1H), 7.29 (d, J=20.96 Hz, 1H), 7.36 (d, J=7.8 Hz, 1H), 7.61 (d, J=6.12 Hz, 2H). LC-MS (m/z): 557.8 (M−H).

Preparation 22: hydrochloride salt of 5'-[5-(4-fluoro, 3,5-dichlorophenyl)-5-(trifluoromethyl)-4,5-dihydrofuran-3-yl]-3'H-spiro[azetidine-3,1'-[2]benzofuran]

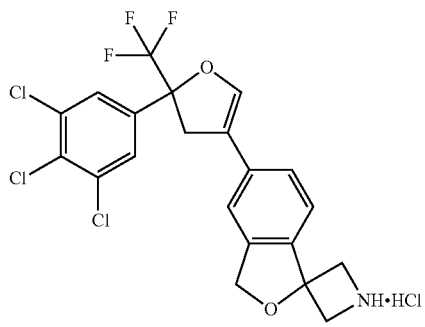

This compound was prepared in an analogous manner to that of Preparation 16 except that tert-butyl 5'-[5-(4-fluoro,3,5-dichlorophenyl)-5-(trifluoromethyl)-4,5-dihydrofuran-3-yl]-3'H-spiro[azetidine-3,1'-[2]benzofuran]carboxylate was used in place of tert-butyl 5'-[5-(3,5-dichlorophenyl)-5-(trifluoromethyl)-4,5-dihydrofuran-3-yl]-3'H-spiro[azetidine-3, 1'-[2]benzofuran]carboxylate. $^1$H NMR (400 MHz, DMSO-d$_6$) δ: 3.21 (d, J=17.16 Hz, 1H), 3.66 (d, J=17.16 Hz, 1H), 4.24-4.27 (m, 4H), 5.00 (s, 2H), 7.16 (s, 1H), 7.26 (d, J=7.84 Hz, 1H), 7.55 (s, 1H), 7.83-7.88 (m, 3H), 9.26 (s, 1H), 9.52 (s, 1H). LC-MS (m/z): 460.0 (M+H).

Example 11

5'-[5-(3,5-dichloro-4-fluorophenyl)-5-(trifluoromethyl)-4,5-dihydrofuran-3-yl]-1-[(methylsulfonyl)acetyl]-3'H-spiro[azetidine-3,1'-[2]benzofuran]

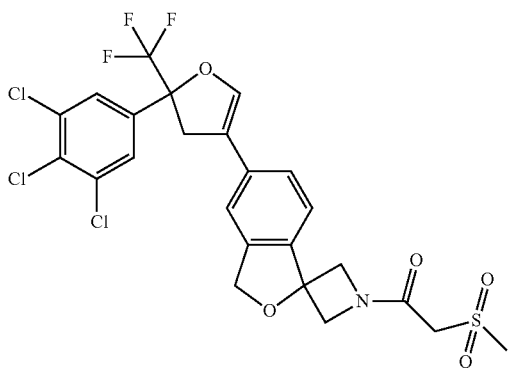 [SMILES: CS(=O)(=O)CC(=O)N1CC2(C1)OCc1cc(C3=COC(c4cc(Cl)c(Cl)c(Cl)c4)(C(F)(F)F)C3)ccc12]

This compound was prepared in an analogous manner to that of Example 7 except that the hydrochloride salt of 5'-[5-(4-fluoro,3,5-dichlorophenyl)-5-(trifluoromethyl)-4,5-dihydrofuran-3-yl]-3'H-spiro[azetidine-3,1'-[2]benzofuran] was used in place of the hydrochloride salt of 5'-[5-(3,5-dichlorophenyl)-5-(trifluoromethyl)-4,5-dihydrofuran-3-yl]-3'H-spiro[azetidine-3,1'-[2]benzofuran].
$^1$H NMR (400 MHz, DMSO-d$_6$) δ: 3.12 (s, 3H), 3.21 (d, J=17.2 Hz, 1H), 3.31 (d, J=17.20 Hz, 1H), 4.15-4.21 (m, 4H), 4.50 (s, 2H), 5.01 (s, 2H), 7.15 (s, 1H), 7.21 (d, J=7.84 Hz, 1H), 7.47 (d, J=7.88 Hz, 1H), 7.54 (s, 1H), 7.87 (d, J=6.36 Hz, 2H). LC-MS (m/z): 579.7 (M+H).

Example 12

5'-[5-(3,5-dichloro-4-fluorophenyl)-5-(trifluoromethyl)-4,5-dihydrofuran-3-yl]-1-isobutyryl-3'H-spiro[azetidine-3,1'-[2]benzofuran]

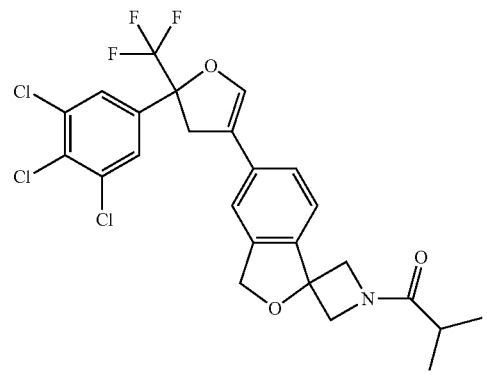 [SMILES: CC(C)C(=O)N1CC2(C1)OCc1cc(C3=COC(c4cc(Cl)c(Cl)c(Cl)c4)(C(F)(F)F)C3)ccc12]

This compound was prepared in an analogous manner to that of Example 11 except that isobutyric acid was used in place of methane sulfonyl acetic acid. $^1$H NMR (400 MHz, CDCl$_3$) δ: 1.00 (t, J=7.14 Hz, 6H), 3.19 (d, J=17.16 hours, 1H), 3.29-3.31 (m, 1H), 3.67 (d, J=18.6 Hz, 1H), 4.05 (s, 2H), 4.35-4.42 (m, 2H), 5.0 (s, 2H), 7.15 (s, 1H), 7.20 (d, J=7.52 Hz, 1H), 7.48 (d, J=7.84 Hz, 1H), 7.54 (s, 1H), 7.87 (d, J=6.36 Hz, 2H). LC-MS (m/z): 527.8 (M−H).

Preparation 23: 3-(3,5-dichloro-4-fluorophenyl)-4,4,4-trifluoro-1-(3'H-spiro[azetidine-3,1'-isobenzofuran]-5'-yl)but-2-en-1-one hydrochloride

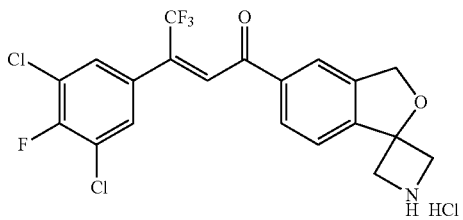 [SMILES: O=C(/C=C(/c1cc(Cl)c(F)c(Cl)c1)C(F)(F)F)c1ccc2c(c1)COC21CNC1 ; Cl]

In a 20 mL microwave vial tert-butyl 5'-(3-(3,5-dichloro-4-fluorophenyl)-4,4,4-trifluorobut-2-enoyl)-3'H-spiro[azetidine-3,1'-isobenzofuran]-1-carboxylate (Preparation 6, 500 mg, 0.92 mmol) was dissolved in methanol (5 mL). Methanolic hydrochloric acid (7.32 mL of a 1.25M solution, 10 eq.) was added and reaction was stirred at 120° C. for 7 minutes in the microwave. Once cooled, reaction was concentrated via rotavap, and chased two times with MTBE. Crude material was a pale yellow foam and was taken forward without purification. $^1$H NMR (400 MHz, DMSO-d$_6$) 7.57-8.07 (m, 6H), 5.11 (s, 2H), 4.32 (s, 4H). LCMS (m/z): 446 (M+H).

Preparation 24: 3-(3,5-dichloro-4-fluorophenyl)-4,4,4-trifluoro-1-(1-(2-(methylsulfonyl)acetyl)-3'H-spiro[azetidine-3,1'-isobenzofuran]-5'-yl)but-2-en-1-one

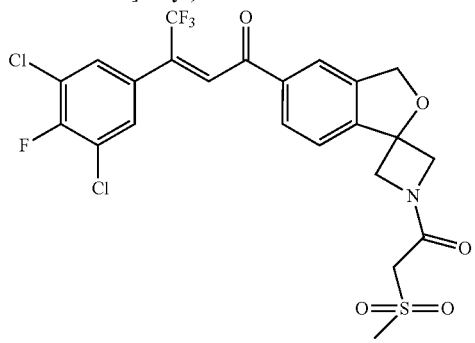

In a vial equipped with stir bar carbonyldiimidazole (210 mg, 1.1 eq.) was dissolved in DMF (2.5 mL) and methylsulfonyl acetic acid (192 mg, 1.2 eq.) was added and stirred for 30 minutes. The resulting activated acid was added to 3-(3,5-dichloro-4-fluorophenyl)-4,4,4-trifluoro-1-(3'H-spiro[azetidine-3,1'-isobenzofuran]-5'-yl)but-2-en-1-one hydrochloride (Preparation 23, 500 mg, 1.12 mmol) dissolved in DMF (2.5 mL). Triethylamine (0.468 mL, 3 eq.) was added slowly and a precipitate formed. The reaction was stirred for 6 hours at ambient temperature. The reaction was partitioned between water (20 mL) and dichloromethane (20 mL). A phase separator column was used to isolate the organics. Crude material was loaded on to ~20 g silica gel precolumn then subjected to chromatography using 40 g RediSepRf silica gel column eluting with 20-100% ethyl acetate in heptanes gradient. Clean fractions were isolated and chased with MTBE to yield 477 mg (75%) as an off white solid. $^1$H NMR (400 MHz, DMSO-d$_6$) 7.58-7.59 (m, 6H), 5.13 (s, 2H), 4.59 (s, 2H), 4.23 (d, J=12.63 Hz, 4H), 3.14 (s, 3H). LC-MS (m/z): 566 (M+H).

Preparation 25: 3-(3,5-dichloro-4-fluorophenyl)-4,4,4-trifluoro-1-(1-isobutyryl-3'H-spiro[azetidine-3,1'-isobenzofuran]-5'-yl)but-2-en-1-one

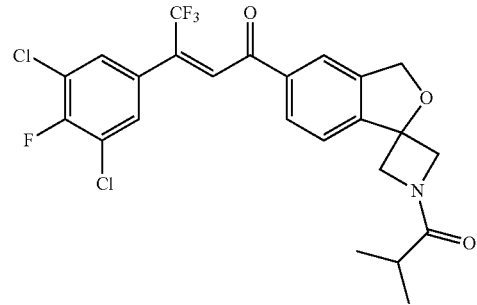 [SMILES: CC(C)C(=O)N1CC2(C1)OCc1cc(C(=O)/C=C(/c3cc(Cl)c(F)c(Cl)c3)C(F)(F)F)ccc12]

To a 40 mL vial equipped with stir bar containing 3-(3,5-dichloro-4-fluorophenyl)-4,4,4-trifluoro-1-(3'H-spiro[azetidine-3,1'-isobenzofuran]-5'-yl)but-2-en-1-one hydrochloride (Preparation 23, 2.0 g, 4.1 mmol) was added DCM (10 mL). The resulting suspension was cooled with an ice bath and isobutyryl chloride (481 μL, 4.56 mmol) was added followed by triethylamine (1.73 mL, 12.4 mmol). Ice bath was removed and heterogeneous mixture was stirred at ambient. Reaction follow by LC-MS and when complete was quenched with water (~20 mL) and organics were isolated by phase separator column then concentrated via rotavap. Desired isolated by chromatography by taking up residue in minimum DCM then loading onto ~25 g silica gel packed precolumn then using 40 g RediSepRf silica gel column eluting with 0-100% ethyl acetate in heptane. Reaction yielded 1.835 g (86%) as a light yellow glass. $^1$H NMR (400 MHz, DMSO-d$_6$) 7.51-7.97 (m, 6H), 5.11 (s, 2H), 4.45 (dd, J=6.82, 9.85 Hz, 2H), 4.12 (s, 2H), 2.57 (spt, J=6.6 Hz, 1H), 1.04 (d, J=6.6 Hz, 6H). LC-MS (m/z): 516 (M+H).

Example 13

1-(5'-(5-(3,5-dichloro-4-fluorophenyl)-5-(trifluoromethyl)-4,5-dihydro-1H-pyrazol-3-yl)-3'H-spiro[azetidine-3,1'-isobenzofuran]-1-yl)-2-(methylsulfonyl)ethanone

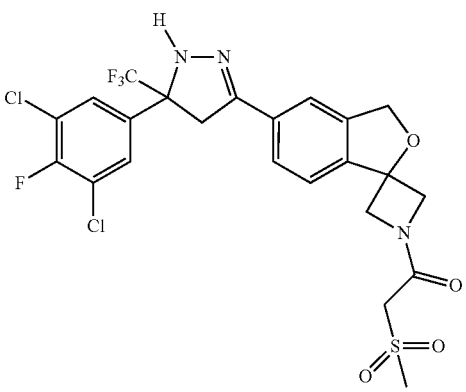 [SMILES: CS(=O)(=O)CC(=O)N1CC2(C1)OCc1cc(C3=NNC(c4cc(Cl)c(F)c(Cl)c4)(C(F)(F)F)C3)ccc12]

An 8 mL vial was charged with 3-(3,5-dichloro-4-fluorophenyl)-4,4,4-trifluoro-1-(1-(2-(methylsulfonyl)acetyl)-3'H-spiro[azetidine-3,1'-isobenzofuran]-5'-yl)but-2-en-1-one (Preparation 24, 200 mg, 0.39 mmol) and ethanol (1 mL). To the resulting heterogeneous mixture was added anhydrous hydrazine (15 μL, 0.48 mmol, 1.3 eq) and the reaction mixture was warmed to reflux. A light yellow solution forms upon heating. Reaction checked by LC-MS after 5 minutes. Reaction appears clean and complete. Removed solvent via rotavap to yield a light yellow foam. Crude residue taken up in minimal DCM and loaded on to ~5 g silica gel pre-column then subjected to chromatography using 12 g RediSepRf silica gel column and eluting with 0-100% ethyl acetate in heptane. Yielded 194 mg (94%) as a white foam. $^1$H-NMR (400 MHz, DMSO-$d_6$) 8.89 (s, 1H), 7.45-7.99 (m, 5H), 5.09 (s, 2H), 4.55 (s, 2H), 4.22 (d, J=14.91 Hz, 4H), 3.82 (dd, J=17.18, 12.63 Hz, 2H), 3.14 (s, 3H). LC-MS (m/z): 580 (M+H).

Example 14

1-(5'-(5-(3,5-dichloro-4-fluorophenyl)-1-methyl-5-(trifluoromethyl)-4,5-di hydro-1H-pyrazol-3-yl)-3'H-spiro[azetidine-3,1'-isobenzofuran]-1-yl)-2-(methyl-sulfonyl)ethanone

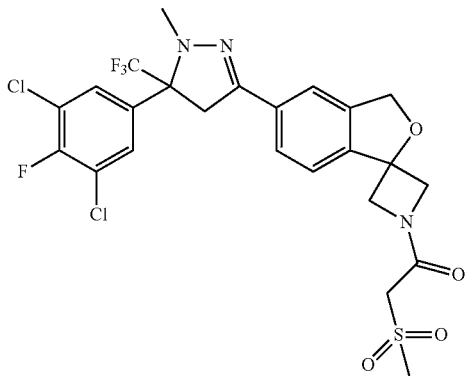 [SMILES: CN1N=C(c2ccc3c(c2)COC32CN(C(=O)CS(C)(=O)=O)C2)CC1(c1cc(Cl)c(F)c(Cl)c1)C(F)(F)F]

This compound was prepared in an analogous manner to that of Example 13 except that methyl hydrazine was used in place of hydrazine and the product was isolated by preparatory HPLC. $^1$H NMR (400 MHz, DMSO-$d_6$) δ 7.67 (d, 1H), 7.55-7.62 (m, 4H), 5.09 (s, 2H), 4.56 (s, 2H), 4.22 (d, J=15.4 Hz, 4H), 4.07 (d, J=18.4 Hz, 1H), 3.73 (d, J=18.2 Hz, 1H), 3.14 (s, 3H), 3.01 (s, 3H). LC-MS (m/z): 594 (M+H).

Example 15

1-(5'-(5-(3,5-dichloro-4-fluorophenyl)-5-(trifluorom-ethyl)-4,5-dihydro-1H-pyrazol-3-yl)-3'H-spiro[azeti-dine-3,1'-isobenzofuran]-1-yl)-2-methylpropan-1-one

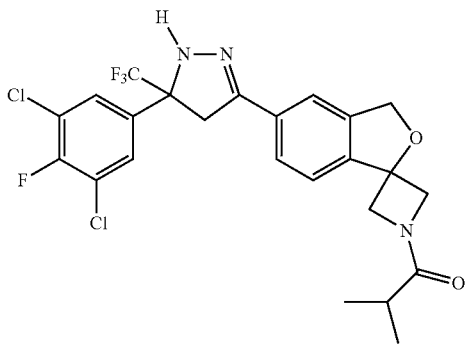 [SMILES: CC(C)C(=O)N1CC2(C1)OCc1cc(C3=NNC(c4cc(Cl)c(F)c(Cl)c4)(C(F)(F)F)C3)ccc12]

This compound was prepared in a manner analogous to Example 13 except that 3-(3,5-dichloro-4-fluorophenyl)-4,4,4-trifluoro-1-(1-isobutyryl-3'H-spiro[azetidine-3,1'-isobenzofuran]-5'-yl)but-2-en-1-one (Preparation 25) was used in place of 3-(3,5-dichloro-4-fluorophenyl)-4,4,4-trifluoro-1-(1-(2-(methylsulfonyl)acetyl)-3'H-spiro[azetidine-3,1'-isobenzofuran]-5'-yl)but-2-en-1-one (Preparation 24). $^1$H NMR (400 MHz, DMSO-$d_6$) 8.88 (s, 1H), 7.47-7.91 (m, 5H), 5.08 (s, 2H), 4.43 (s, 2H), 4.10 (s, 2H), 3.81 (dd, J=18.44, 14.40 Hz, 2H), 2.54 (spt, J=6.8 Hz, 1H), 1.02 (t, J=7.71 Hz, 6H); LC-MS (m/z): 530 (M+H).

Example 16

1-(5'-(5-(3,5-dichloro-4-fluorophenyl)-1-methyl-5-(trifluoromethyl)-4,5-dihydro-1H-pyrazol-3-yl)-3'H-spiro[azetidine-3,1'-isobenzofuran]-1-yl)-2-methyl-propan-1-one

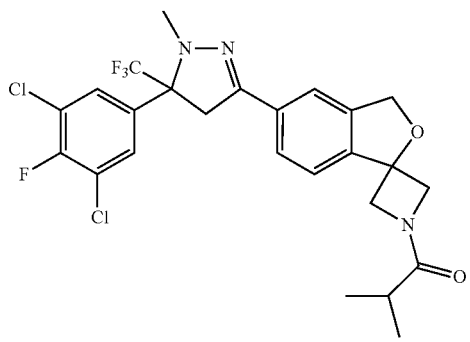 [SMILES: CC(C)C(=O)N1CC2(C1)OCc1cc(C3=NN(C)C(c4cc(Cl)c(F)c(Cl)c4)(C(F)(F)F)C3)ccc12]

This compound was prepared in an analogous manner to that of Example 14 except that except that 3-(3,5-dichloro-4-fluorophenyl)-4,4,4-trifluoro-1-(1-isobutyryl-3'H-spiro[azetidine-3,1'-isobenzofuran]-5'-yl)but-2-en-1-one (Preparation 25) was used in place of 3-(3,5-dichloro-4-fluorophenyl)-4,4,4-trifluoro-1-(1-(2-(methylsulfonyl)acetyl)-3'H-spiro[azetidine-3,1'-isobenzofuran]-5'-yl)but-2-en-1-one (Preparation 24). $^1$H NMR (400 MHz, DMSO-$d_6$) 7.50-7.75 (m, 5H), 5.08 (s, 2H), 4.44 (s, 2H), 3.99-4.19 (m, 3H), 3.73 (d, J=18.44 Hz, 1H), 3.01 (s, 3H), 2.54 (spt, J=6.30 Hz, 1H), 1.03 (t, J=7.20 Hz, 6H); LC-MS (m/z): 544 (M+H).

Preparation 26: 5-(4,4,4-trifluoro-3-(3,4,5-trichlo-rophenyl)but-2-enoyl)-3'H-spiro[azetidine-3,1'-isobenzofuran]hydrochloride

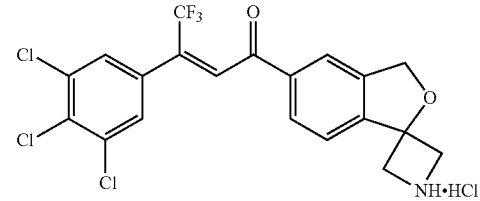

To tert-butyl 5'-(4,4,4-trifluoro-3-(3,4,5-trichlorophenyl)but-2-enoyl)-3'H-spiro[azetidine-3,1'-isobenzofuran]-1-carboxylate (Preparation 2, 3.9 g, 6.94 mmol, 1 eq) was added methanolic HCl (30 mL of 1.25M solution, 37.5 mmol) at 0° C. Resulting reaction mixture was stirred at room temperature for 16 hours. After consumption of starting material, reaction mixture was concentrated to get yellow sticky mass, which was dissolved in chloroform (20 mL) and chloroform was stripped out. This procedure was repeated twice to get title compound as pale yellow solid (3.4 g, crude). Crude compound was used as such for next reaction. LC-MS (m/z): 463.8 (M+H).

Preparation 27: 4,4,4-trifluoro-1-(1-isobutyryl-3'H-spiro[azetidine-3,1-isobenzofuran]-5'-yl)-3-(3,4,5-trichlorophenyl)but-2-en-1-one

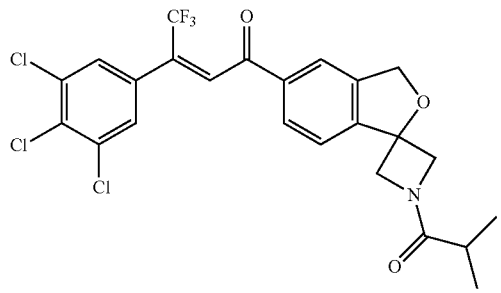 [SMILES: CC(C)C(=O)N1CC2(C1)OCc1cc(C(=O)/C=C(/c3cc(Cl)c(Cl)c(Cl)c3)C(F)(F)F)ccc12]

To the stirred solution of hydrochloride salt of 5'-(4,4,4-trifluoro-3-(3,4,5-trichlorophenyl)but-2-enoyl)-3'H-spiro[azetidine-3,1'-isobenzofuran](Preparation 26, 1.0 g, 2.2 mmol, 1 eq) in DMF (10 mL) was added Et₃N (2.4 mL, 17.3mmol, 8 eq) followed by addition of iso-butyric acid (0.38 g, 4.32mmol, 2 eq), HOBt (0.29 g, 2.16 mmol, 1 eq) and EDC.HCl (0.62 g, 3.24 mmol, 1.5 eq) at room temperature. Resulting reaction mixture was stirred at room temperature for 18 hours under nitrogen atmosphere. After consumption of starting material, reaction mixture was quenched by water (30 mL) and extracted with ethyl acetate (3×25 mL). Combined organic layer was washed with aqueous sodium bicarbonate (50 mL), aqueous LiCl solution (2×50 mL), brine (50 mL) and dried over sodium sulfate. Organic layer was concentrated in vacuo to get brown sticky oil (1.0 g, Crude). Purification was done by Combiflash chromatography using 40 g Redisep column. Compound was eluted in 40% ethyl acetate in n-hexane to get title compound as off white solid (0.5 g, 43%). $^1$H NMR (400 MHz, CDCl₃) δ: 1.13-1.17 (m, 6H), 2.46-2.53 (m, 1H), 4.25 (d, J=10.64 Hz, 1H), 4.30-4.34 (m, 2H), 4.52 (d, J=9.32 Hz, 1H), 5.15 (s, 2H), 7.27 (s, 2H), 7.40 (d, J=1.36 Hz, 1H), 7.49 (d, J=8.04 Hz, 1H), 7.68 (s, 1H), 7.84 (d, J=7.92 Hz, 1H). LC-MS (m/z): 531.9 (M+H).

Example 17

1-(5'-(5-(3,4,5-trichlorophenyl)-5-(trifluoromethyl)-4,5-dihydro-1H-pyrazol-3-yl)-3'H-spiro[azetidine-3,1'-isobenzofuran]-1-yl)propan-1-one

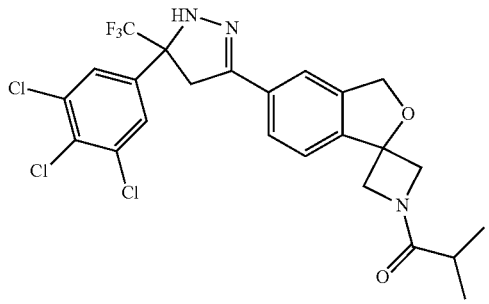 [SMILES: CC(C)C(=O)N1CC2(C1)OCc1cc(C3=NNC(c4cc(Cl)c(Cl)c(Cl)c4)(C(F)(F)F)C3)ccc12]

To the stirred solution of 4,4,4-trifluoro-1-(1-isobutyryl-3'H-spiro[azetidine-3,1'-isobenzofuran]-5'-yl)-3-(3,4,5-trichlorophenyl)but-2-en-1-one (Preparation 27, 0.5 g, 0.938 mmol, 1 eq) in ethanol (5 mL) was added hydrazine (1.0M solution in THF, 1.40 mL, 1.41 mmol, 1.5 eq). Resulting reaction mixture was refluxed for 2 hours under nitrogen atmosphere. After consumption of starting material, Reaction mixture was concentrated to get crude compound. Crude compound was dissolved in minimum quantity of ethyl acetate and adsorbed on silica gel (100-200 mesh). Crude compound purified by Combiflash chromatography using 40 g Redisep column. Desired compound was eluted in 55% ethyl acetate in hexane to afford title compound as off white solid (0.16 g, 31%). $^1$H NMR (400 MHz, DMSO-d₆) δ: 1.00-1.06 (m, 6H), 2.53-2.56 (m, 1H), 3.75-3.88 (m, 2H), 4.10 (s, 2H), 4.40-4.45 (m, 2H), 5.08 (s, 2H), 7.57-7.58 (m, 2H), 7.66 (d, J=8.44 Hz, 1H), 7.88 (s, 2H), 8.91 (s, 1H). LC-MS (m/z): 546.0 (M+H). HPLC Purity: 96.43%.

Example 18

2-(methylsulfonyl)-1-(5'-(5-(3,4,5-trichlorophenyl)-5-(trifluoromethyl)-4,5-dihydro-1H-pyrazol-3-yl)-3'H-spiro[azetidine-3,1'-isobenzofuran]-1-yl)ethanone hydrochloride

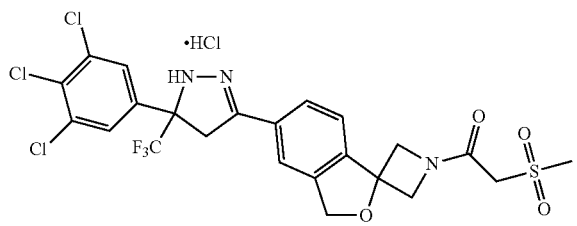 [SMILES: CS(=O)(=O)CC(=O)N1CC2(C1)OCc1cc(C3=NNC(c4cc(Cl)c(Cl)c(Cl)c4)(C(F)(F)F)C3)ccc12 ; Cl]

Step 1: Prepared 4,4,4-trifluoro-1-(1-(2-(methylsulfonyl)acetyl)-3'H-spiro[azetidine-3,1'-isobenzofuran]-5'-yl)-3-(3,4,5-trichlorophenyl)but-2-en-1-one

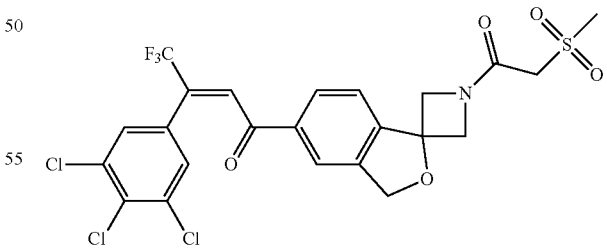

by using procedure similar to that of Preparation 27 using methylsulfonylacetic acid in place of isobutyric acid. Yield 1.34 g (55%). $^1$H NMR (400 MHz, CDCl₃) δ: 3.19 (s, 3H), 3.86 (s, 2H), 4.33 (d, J=11.32 Hz, 1H), 4.44 (d, J=11.12 Hz, 1H), 4.64-4.69 (m, 2H), 5.16 (s, 2H), 7.27 (s, 2H), 7.4 (d, J=1.28 Hz, 1H), 7.63 (d, J=8.0 Hz, 1H), 7.68 (s, 1H), 7.83-7.87 (m, 1H).

Step 2: Prepared 2-(methylsulfonyl)-1-(5'-(5-(3,4,5-trichlorophenyl)-5-(trifluoromethyl)-4,5-dihydro-1H-pyrazol-3-yl)-3'H-spiro[azetidine-3,1'-isobenzofuran]-1-yl)ethanone

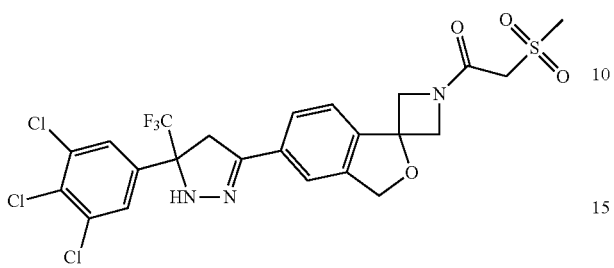

by using procedure similar to that of Example 17 using 4,4,4-trifluoro-1-(1-(2-(methylsulfonyl)acetyl)-3'H-spiro[azetidine-3,1'-isobenzofuran]-5'-yl)-3-(3,4,5-trichlorophenyl)but-2-en-1-one in place of 4,4,4-trifluoro-1-(1-isobutyryl-3'H-spiro[azetidine-3,1'-isobenzofuran]-5'-yl)-3-(3,4,5-trichlorophenyl)but-2-en-1-one. Yield: 0.71 g (Crude). Crude compound was used as such for the next reaction. $^1$H NMR (400 MHz, CDCl$_3$) δ: 3.18 (s, 1H), 3.38 (d, J=17.32 Hz, 1H), 3.82-3.89 (m, 3H), 4.34 (d, J=10.92 Hz, 1H), 4.43 (d, J=11.16 Hz, 1H), 4.62-4.65 (m, 2H), 5.14 (s, 2H), 6.43 (s, 1H), 7.51-7.55 (m, 4H), 7.61 (d, J=8.08 Hz, 1H). LC-MS (m/z): 594.0 (M−H).

Step 3: Prepared tert-butyl 3-(1-(2-(methylsulfonyl)acetyl)-3'H-spiro[azetidine-3,1'-isobenzofuran]-5'-yl)-5-(3,4,5-trichlorophenyl)-5-(trifluoromethyl)-4,5-dihydro-1H-pyrazole-1-carboxylate

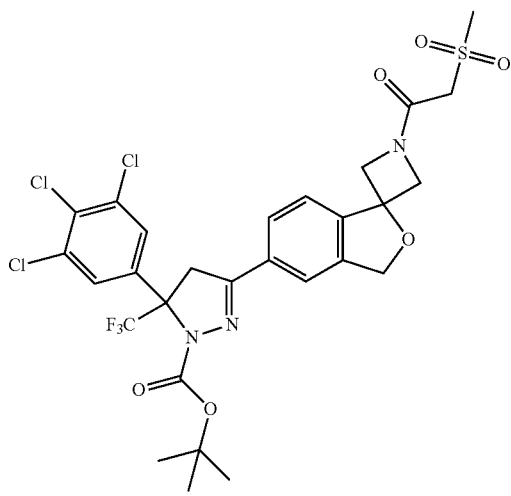 [SMILES: CC(C)(C)OC(=O)N1N=C(c2ccc3c(c2)COC32CN(C(=O)CS(C)(=O)=O)C2)CC1(c1cc(Cl)c(Cl)c(Cl)c1)C(F)(F)F]

by adding triethyl amine (2.2 eq.) to a stirred solution of 2-(methylsulfonyl)-1-(5'-(5-(3,4,5-trichlorophenyl)-5-(trifluoromethyl)-4,5-dihydro-1H-pyrazol-3-yl)-3'H-spiro[azetidine-3,1'-isobenzofuran]-1-yl)ethanone (1 eq) in DCM (0.2M) followed by DMAP (0.5 eq) and di-tert-butyl dicarbonate (2 eq). Resulting reaction mixture was stirred for 12 hours at room temperature under nitrogen atmosphere. After consumption of starting material reaction mixture diluted with ethyl acetate and washed with water then brine. Organic layer dried over sodium sulphate and evaporated to get as yellow solid (crude). Crude compound was purified by column chromatography (100-200 mesh). Title compound eluted in 25% ethyl acetate in hexane. Yielded 0.35 g (42%). $^1$H NMR (400 MHz, CDCl$_3$) δ: 1.31 (s, 9H), 3.18 (s, 3H), 3.55 (d, J=18.24 Hz, 1H), 3.82-3.85 (s, 2H), 3.90-4.08 (m, 1H), 4.34 (d, J=10.6 Hz, 1H), 4.43 (d, J=10.96 Hz, 1H), 4.62-4.68 (m, 2H), 5.14 (s, 2H), 7.39 (s, 1H), 7.51-7.55 (m, 2H), 7.60-7.64 (m, 1H), 7.73 (bs, 1H). LC-MS (m/z): 696.0 (M−H).

Step 4: Prepared 2-(methylsulfonyl)-1-(5'-(5-(3,4,5-trichlorophenyl)-5-(trifluoromethyl)-4,5-dihydro-1H-pyrazol-3-yl)-3'H-spiro[azetidine-3,1'-isobenzofuran]-1-yl)ethanone hydrochloride

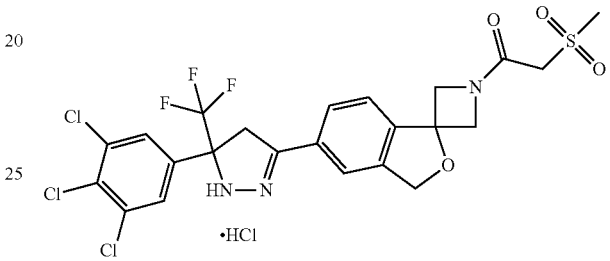

by dissolving tert-butyl 3-(1-(2-(methylsulfonyl)acetyl)-3'H-spiro[azetidine-3,1'-isobenzofuran]-5'-yl)-5-(3,4,5-trichlorophenyl)-5-(trifluoromethyl)-4,5-dihydro-1H-pyrazole-1-carboxylate in dioxane (0.2M) and purged with HCl gas at 0° C. for 30 minutes. Reaction mixture was then stirred for 30 minutes at room temperature. After consumption of starting material, reaction mixture reaction mixture was concentrated in vacuo to get an orange semisolid. Crude was triturated with Chloroform:hexane (1:8) to afford title compound as off white solid. Yield: 105 mg (35%). $^1$H NMR (400 MHz, CDCl$_3$) δ: 3.18 (s, 3H), 3.38 (d, J=17.2 Hz, 1H), 3.85-3.89 (m, 3H), 4.33 (d, J=9.8 Hz, 1H), 4.43 (d, J=11.08 Hz, 1H), 4.65 (s, 2H), 5.14 (s, 2H), 6.42 (s, 1H), 7.50-7.54 (m, 4H), 7.60-7.62 (d, J=7.8 Hz, 1H). LC-MS (m/z):=593.8 (M−H). HPLC 87.81%.

Example 19

1-(5'-(5-(3,5-dichlorophenyl)-5-(trifluoromethyl)-4,5-dihydro-1H-pyrazol-3-yl)-3'H-spiro[azetidine-3,1'-isobenzofuran]-1-yl)-2-methylpropan-1-one hydrochloride

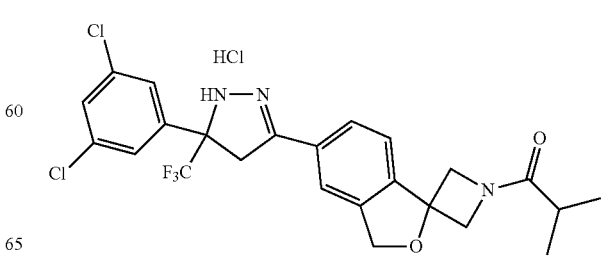

Step 1: Prepared 3-(3,5-dichlorophenyl)-4,4,4-trifluoro-1-(3'H-spiro[azetidine-3,1'-isobenzofuran]-5'-yl)but-2-en-1-one hydrochloride

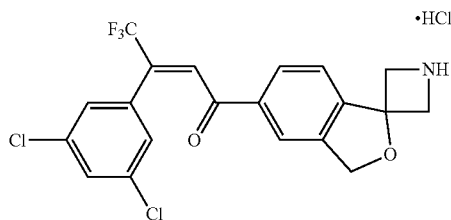 [SMILES: Cl ; O=C(/C=C(\c1cc(Cl)cc(Cl)c1)C(F)(F)F)c1ccc2c(c1)COC21CNC1]

in a manner analogous to Preparation 26 using tert-butyl 5'-(3-(3,5-dichlorophenyl)-4,4,4-trifluorobut-2-enoyl)-3'H-spiro[azetidine-3,1'-isobenzofuran]-1-carboxylate in place of tert-butyl 5'-(4,4,4-trifluoro-3-(3,4,5-trichlorophenyl)but-2-enoyl)-3'H-spiro[azetidine-3,1'-isobenzofuran]-1-carboxylate. Yield: 3.6 g (Crude). Crude compound was used as such for the next reaction. LC-MS (m/z): 427.7 (M+H).

Step 2: Prepared 3-(3,5-dichlorophenyl)-4,4,4-trifluoro-1-(1-isobutyryl-3'H-spiro[azetidine-3,1'-isobenzofuran]-5'-yl)but-2-en-1-one

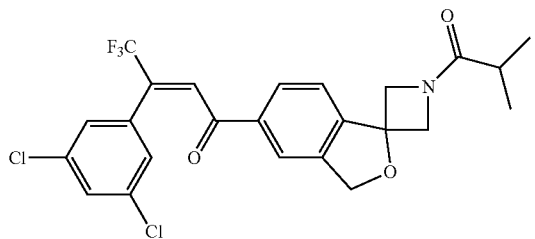 [SMILES: CC(C)C(=O)N1CC2(C1)OCc1cc(C(=O)/C=C(\c3cc(Cl)cc(Cl)c3)C(F)(F)F)ccc12]

in a manner analogous to Preparation 27 using 3-(3,5-dichlorophenyl)-4,4,4-trifluoro-1-(3'H-spiro[azetidine-3,1'-isobenzofuran]-5'-yl)but-2-en-1-one hydrochloride in place of 4,4,4-trifluoro-1-(3'H-spiro[azetidine-3,1'-isobenzofuran]-5'-yl)-3-(3,4,5-trichlorophenyl)but-2-en-1-one hydrochloride. Yield: 75 mg (Crude). Crude compound was used as such for the next reaction.
$^1$H NMR (400 MHz, CDCl$_3$) δ: 1.15 (t, J=6.56 Hz, 6H), 2.48-2.52 (m, 1H), 3.41 (d, J=17.32 Hz, 1H), 4.05 (d, J=17.24 Hz, 1H), 4.22-4.37 (m, 3H), 4.50 (d, J=9.12 Hz, 1H), 5.13 (s, 2H), 6.43 (s, 1H), 7.38-7.43 (m, 4H), 7.53 (bs, 1H), 7.62 (d, J=7.92 Hz, 1H). LC-MS (m/z): 510.0 (M−H).

Step 3: Prepared 1-(5'-(5-(3,5-dichlorophenyl)-5-(trifluoromethyl)-4,5-dihydro-1H-pyrazol-3-yl)-3'H-spiro[azetidine-3,1'-isobenzofuran]-1-yl)-2-methylpropan-1-one

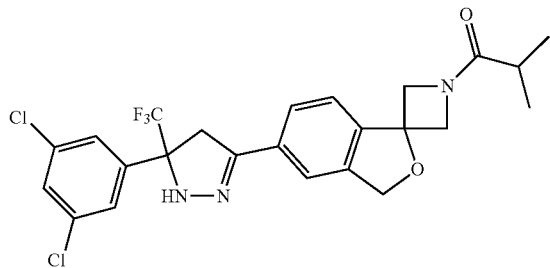 [SMILES: CC(C)C(=O)N1CC2(C1)OCc1cc(C3=NNC(c4cc(Cl)cc(Cl)c4)(C(F)(F)F)C3)ccc12]

in a manner analogous to Example 17 using 3-(3,5-dichlorophenyl)-4,4,4-trifluoro-1-(1-isobutyryl-3'H-spiro[azetidine-3,1'-isobenzofuran]-5'-yl)but-2-en-1-one in place of 4,4,4-trifluoro-1-(1-isobutyryl-3'H-spiro[azetidine-3,1'-isobenzofuran]-5'-yl)-3-(3,4,5-trichlorophenyl)but-2-en-1-one. Yield: 75 mg (crude). Crude compound was used as such for the next reaction. $^1$H NMR (400 MHz, CDCl$_3$) δ: 1.15 (t, J=6.56 Hz, 6H), 2.48-2.52 (m, 1H), 3.41 (d, J=17.32 Hz, 1H), 4.05 (d, J=17.24 Hz, 1H), 4.22-4.37 (m, 3H), 4.50 (d, J=9.12 Hz, 1H), 5.13 (s, 2H), 6.43 (s, 1H), 7.38-7.43 (m, 4H), 7.53 (bs, 1H), 7.62 (d, J=7.92 Hz, 1H). LC-MS (m/z): 510.0 (M−H).

Step 4: Prepared tert-butyl 5-(3,5-dichlorophenyl)-3-(1-isobutyryl-3'H-spiro[azetidine-3,1'-isobenzofuran]-5'-yl)-5-(trifluoromethyl)-4,5-dihydro-1H-pyrazole-1-carboxylate

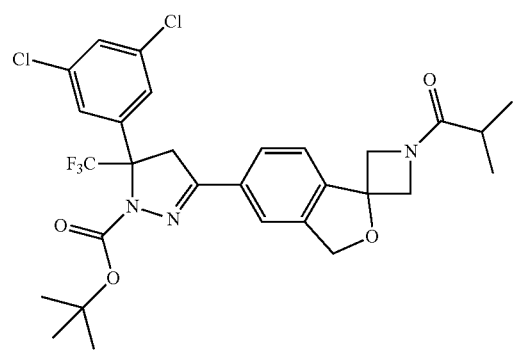 [SMILES: CC(C)C(=O)N1CC2(C1)OCc1cc(C3=NN(C(=O)OC(C)(C)C)C(c4cc(Cl)cc(Cl)c4)(C(F)(F)F)C3)ccc12]

using a procedure similar to that if Example 18 Step 3 using 1-(5'-(5-(3,5-dichlorophenyl)-5-(trifluoromethyl)-4,5-dihydro-1H-pyrazol-3-yl)-3'H-spiro[azetidine-3,1'-isobenzofuran]-1-yl)-2-methylpropan-1-one in place of 2-(methylsulfonyl)-1-(5'-(5-(3,4,5-trichlorophenyl)-5-(trifluoromethyl)-4,5-dihydro-1H-pyrazol-3-yl)-3'H-spiro[azetidine-3,1'-isobenzofuran]-1-yl)ethanone. Yield: 0.45 g (50%). $^1$H NMR (400 MHz, CDCl$_3$) δ: 1.14 (t, J=6.12 Hz, 6H), 1.28 (bs, 9H), 2.47-2.54 (m, 1H), 3.57 (d, J=19 Hz, 1H), 4.05 (d, J=19.04 Hz, 1H), 4.24 (d, J=10.32 Hz, 1H), 4.34 (dd, J$_1$=9.52 Hz, J$_2$=13.12 Hz, 2H), 4.51 (d, J=9.04 Hz, 1H), 5.13 (s, 2H), 7.26 (s, 2H), 7.36 (s, 1H), 7.44 (d, J=8.08 Hz, 1H), 7.65-7.71 (m, 2H), LC-MS (m/z):=610.0 (M−H).

Step 5: Prepared 1-(5'-(5-(3,5-dichlorophenyl)-5-(trifluoromethyl)-4,5-dihydro-1H-pyrazol-3-yl)-3'H-spiro[azetidine-3,1'-isobenzofuran]-1-yl)-2-methylpropan-1-one hydrochloride

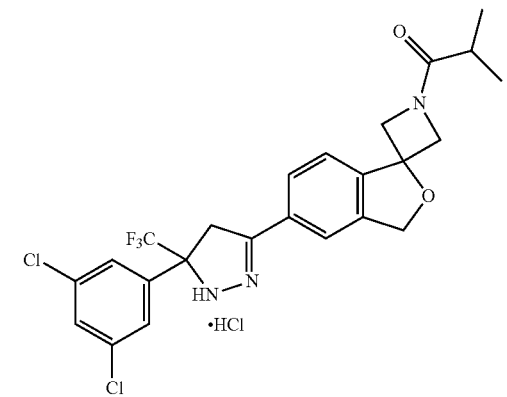 [SMILES: CC(C)C(=O)N1CC2(C1)OCc1cc(C3=NNC(c4cc(Cl)cc(Cl)c4)(C(F)(F)F)C3)ccc12 ; Cl]

in a manner analogous to Example 18 Step 4 using tert-butyl 5-(3,5-dichlorophenyl)-3-(1-isobutyryl-3'H-spiro[azetidine-3,1'-isobenzofuran]-5-yl)-5-(trifluoromethyl)-4,5-dihydro-1H-pyrazole-1-carboxylate in place of tert-butyl 3-(1-(2-(methylsulfonyl)acetyl)-3'H-spiro[azetidine-3,1'-isobenzofuran]-5'-yl)-5-(3,4,5-trichlorophenyl)-5-(trifluoromethyl)-4,5-dihydro-1H-pyrazole-1-carboxylate. Yield: 110 mg (29%). $^1$H NMR (400 MHz, CDCl$_3$) δ: 1.14 (d, J=6.0 Hz, 6H), 2.47-2.54 (m, 1H), 3.40 (d, J=17.16 Hz, 1H), 3.87 (d, J=17.2 Hz, 1H), 4.26-4.36 (m, 3H), 4.40-4.49 (m, 1H), 5.13 (s, 2H), 6.42 (s, 1H), 7.38-7.43 (m, 4H), 7.53 (s, 1H), 7.62 (d, J=7.56 Hz, 1H). LC-MS (m/z): 512.3 (M+H).

Example 20

1-(5'-(5-(3,5-dichlorophenyl)-5-(trifluoromethyl)-4,5-dihydro-1H-pyrazol-3-yl)-3'H-spiro[azetidine-3,1'-isobenzofuran]-1-yl)methylsulfonyl)-ethanone

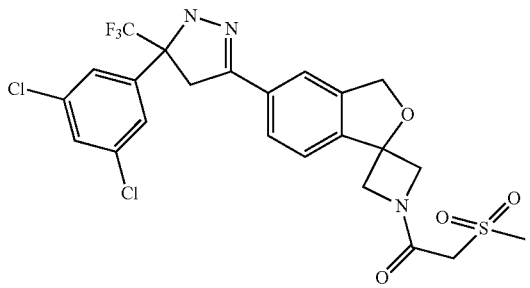 [SMILES: CS(=O)(=O)CC(=O)N1CC2(C1)OCc1cc(C3=NNC(c4cc(Cl)cc(Cl)c4)(C(F)(F)F)C3)ccc12]

This compound was prepared in an analogous manner to that of Example 17, except that 3-(3,5-dichlorophenyl)-4,4,4-trifluoro-1-(1-(2-(methylsulfonyl)-acetyl)-3'H-spiro[azetidine-3,1'-isobenzofuran]-5-yl)but-2-en-1-one was used in place of 4,4,4-trifluoro-1-(1-isobutyryl-3'H-spiro[azetidine-3,1'-isobenzofuran]-5'-yl)-3-(3,4,5-trichloro phenyl)but-2-en-1-one. Yield: 75 mg (15%). $^1$H NMR (400 MHz, DMSO-d$_6$) δ: 3.13 (s, 3H), 3.72-3.88 (m, 2H), 4.21 (d, J=17.08 Hz, 4H), 4.54 (s, 2H), 5.09 (s, 2H), 7.56-7.59 (m, 2H), 7.66-7.69 (m, 3H), 7.71-7.72 (m, 1H), 8.91 (s, 1H). LC-MS (m/z): 559.9 (M−H). HPLC Purity: 98.10%.

Preparation 28: benzyl-trimethylsilanylmethyl-amine

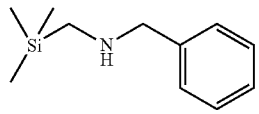

To a stirred solution of chloromethyl-trimethyl-silane (25 g, 203.79 mmol, 1 eq.) in acetonitrile (250 mL) was added distilled benzyl amine (44.56 mL, 407.59 mmol, 2 eq) at room temperature. Resulting reaction mixture was refluxed for 16 hours. After consumption of starting material, reaction mixture was cooled to room temperature; benzyl amine hydrochloride salt was precipitate out. Solid was removed by filtration and filtrate was concentrated under reduced pressure to get yellow semi solid. Water was added to residue and extracted with ethyl acetate (3×100 mL). Combined organic layer was washed with brine (200 mL), dried over anhydrous sodium sulfate and concentrated under reduced pressure to afford product as yellow liquid (25 g, crude). Crude used as such for next reaction. $^1$H-NMR (400 MHz, CDCl$_3$) δ: 0.03 (s, 9H), 2.04 (s, 2H), 3.79 (s, 2H), 3.86 (s, 1H), 7.29-7.33 (m, 5H). (m/z): 193.8 (M+H)

Preparation 29: benzyl-methoxymethyl-trimethylsilanylmethyl-amine

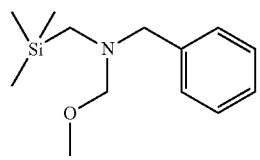 [SMILES: COCN(Cc1ccccc1)C[Si](C)(C)C]

To a stirred solution of benzyl-trimethylsilanylmethyl-amine (Preparation 28, 25 g, 128.86 mmol) in methanol (300 mL), formaldehyde solution (37-41% w/v, 4.253 g, 141.75 mmol) was added at 0° C. Resulting reaction mixture was stirred at 0° C. for 1 hour and 10-15° C. for 3 hours. K$_2$CO$_3$ (21.34 g, 154.69 mmol) was added to reaction mixture and reaction was stirred at 10-15° C. for 2 hours. After complete consumption of starting material, the resulting reaction mixture was filtered through Buchner funnel; solid was washed by ethyl acetate (3×20 mL). Combined filtrate was concentrated in vacuo to afford product as faint yellow oil (23 g, Crude). Crude compound was used as such for next reaction. (m/z): 195.1 (M+H).

Preparation 30: 1-benzyl-3-(3,5-dichloro-4-fluoro-phenyl)-3-trifluoromethyl-pyrrolidine

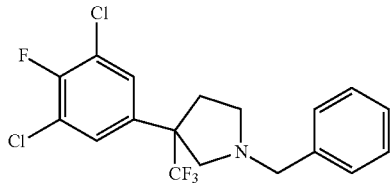 [SMILES: Fc1c(Cl)cc(C2(C(F)(F)F)CCN(Cc3ccccc3)C2)cc1Cl]

To a stirred solution of 1,3-dichloro-2-fluoro-5-(1-trifluoromethyl-vinyl)-benzene (10 g, 38.61 mmol) in DCM (150 mL) was added benzyl-methoxymethyl-trimethylsilanylmethyl-amine (36.6 g, 154.44 mmol) at room temperature and reaction mixture was cooled to 0° C. followed by slow addition of TFA (0.29 mL, 3.861 mmol). Resulting reaction mixture was stirred at room temperature for 5 hours. After complete consumption of starting material, the reaction mixture was quenched with aqueous Na$_2$CO$_3$ and extracted with DCM (3×100 mL). Combined organic layer was dried over Na$_2$SO$_4$ and concentrated under vacuum to afford brown oil (9.7 g, crude). Crude compound was purified by column chromatography using 100-200 mesh silica gel. Desired product was eluted in 4% ethyl acetate in hexane to afford product as brownish solid (6.1 g, impure). Impure compound was used as such for next reaction. $^1$H-NMR (400 MHz, CDCl$_3$) δ: 2.24-2.31 (m, 1H), 2.53-2.59 (m, 1H), 2.68-2.78 (m, 1H), 2.80-2.83 (m, 1H), 3.01-3.08 (m, 2H), 3.61-3.69 (m, 2H), 7.29-7.34 (m, 7H). (m/z): 280.4 (M+H).

Preparation 31: 3-(3,5-dichloro-4-fluoro-phenyl)-3-trifluoromethyl-pyrrolidine

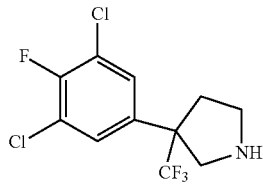 [SMILES: Fc1c(Cl)cc(C2(C(F)(F)F)CCNC2)cc1Cl]

To a stirred solution of 1-benzyl-3-(3,5-dichloro-4-fluoro-phenyl)-3-trifluoromethyl-pyrrolidine (Preparation 30, 6.1 g, 15.60 mmol) in 1,2-dichloroethane (50 mL) was added 1-chloroethyl chloroformate (3.01 mL, 28.08 mmol) at room temperature. Resulting reaction mixture was refluxed for 3 hours. After complete consumption of starting material, reaction mixture was concentrated in vacuo to afford brown thick oil. Brown thick oil was dissolved in MeOH (50 mL) and refluxed for 2 hours. Progress of reaction was monitored by TLC. After complete consumption of starting material, reaction mixture was again concentrated to afford brown thick oil, to which water was added (100 mL) and washed with hexane (3×50 mL). Aqueous layer was basified by saturated sodium bicarbonate solution, extracted with ethyl acetate (3×50 mL). Combined organic layer was dried over anhydrous sodium sulfate, concentrated under reduced pressure to afford product as brown thick oil (6.1 g, crude). Crude was purified by column chromatography on (100-200 mesh silica). Desired product was eluted in 25% ethyl acetate in hexane to afford brown semi solid (3.8 g, 80.68%). $^1$H-NMR (400 MHz, DMSO-$d_6$) δ: 2.39-2.46 (m, 1H), 2.53-2.58 (m, 1H), 2.99-3.13 (m, 2H), 3.53 (d, 1H, J=12.84 Hz), 3.65 (d, 1H, J=12.84 Hz), 7.77 (d, 2H J=6.28 Hz). (m/z): 302.2 (M+H).

Preparation 32: 5'-[3-(3,5-dichloro-4-fluorophenyl)-3-(trifluoromethyl)pyrrolidin-1yl]-1-tert-butyl 3'H-spiro[azetidine-3,1'-[2]benzofuran carbamate

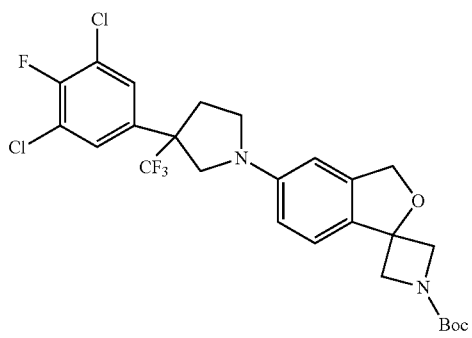 [SMILES: CC(C)(C)OC(=O)N1CC2(C1)OCc1cc(N3CCC(c4cc(Cl)c(F)c(Cl)c4)(C(F)(F)F)C3)ccc12]

To a stirred solution of 3-(3,5-dichloro-4-fluoro-phenyl)-3-trifluoromethyl-pyrrolidine (Preparation 31, 1 g, 3.32 mmol) in dry toluene (15 mL) was added tert-butyl 5'-bromo-3'H-spiro[azetidine-3,1'-isobenzofuran]-1-carboxylate (Intermediate 1) (1.01 g, 2.99 mmol) and reaction mixture was then degassed for 30 minutes by nitrogen gas. Pd$_2$(dba)$_3$ chloroform adduct (0.069 g, 0.066 mmol), sodium tertiary butoxide (0.478 g, 4.98 mmol) and Xantphos (0.115 g, 0.199 mmol) were added at room temperature. Resulting reaction mixture was refluxed for 6 hours. After complete consumption of starting material, reaction mixture was quenched with water (20 mL) and extracted with ethyl acetate (3×50 mL). Combined organic layer was washed with brine (100 mL), dried over anhydrous sodium sulfate and concentrated under vacuum to afford brown oil (1.9 g, crude). Crude compound was purified by column chromatography (100-200 mesh silica). Desired product was eluted in 12% ethyl acetate in hexane to afford product as yellow oil (0.25 g, 13.44%). $^1$H-NMR (400 MHz, CDCl$_3$) δ: 1.46 (s, 9H), 2.50-2.55 (m, 1H), 2.80-2.86 (m, 1H), 3.48-3.51 (m, 1H), 3.53-3.55 (m, 1H), 3.76 (d, 1H J=10.24 Hz), 4.03 (d, 1H J=10.28 Hz), 4.10 (d, 2H J=9.48 Hz), 4.27 (d, 2H J=9.4 Hz), 5.06 (s, 2H), 6.39 (s, 1H), 6.59 (dd, 1H, J$_1$=8.3 Hz, J$_2$=1.68 Hz), 7.31-7.35 (m, 3H). (m/z): 561.0 (M+H).

Preparation 33: 5'-[3-(3,5-dichloro-4-fluorophenyl)-3-(trifluoromethyl)pyrrolidin-1yl]-3'H-spiro[azetidine-3,1'-[2]benzofuran

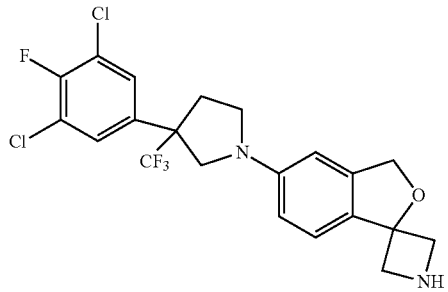 [SMILES: Fc1c(Cl)cc(C2(C(F)(F)F)CCN(c3ccc4c(c3)COC43CNC3)C2)cc1Cl]

To a stirred solution of 5'-[3-(3,5-dichloro-4-fluorophenyl)-3-(trifluoromethyl)pyrrolidin-1yl]-1-tert-butyl 3'H-spiro[azetidine-3,1'-[2]benzofuran carbamate (Preparation 32, 0.85 g, 1.518 mmol, 1 eq) in MeOH (2 mL) was purged dry HCl gas for 15 minutes at 0° C. After complete consumption of starting material, the reaction mixture was concentrated under reduced pressure to afford brown colored thick oil, which was triturated with n-pentane (4×10 mL) to afford product as brownish solid (0.45 g, crude). Crude compound was used as such for next reaction. $^1$H-NMR (400 MHz, CDCl$_3$) δ: 2.50-2.55 (m, 1H), 2.81-2.87 (m, 1H), 3.46-3.47 (m, 1H), 3.51-3.55 (m, 1H), 3.76 (d, 1H, J=10.4 Hz), 4.02 (d, 1H, J=10.32 Hz), 4.35 (bs, 2H), 4.51 (bs, 2H), 5.06 (s, 2H), 6.37 (s, 1H), 6.66 (d, 1H, J=7.56 Hz), 7.34 (d, 2H J=5.92 Hz), 7.91 (d, 1H, J=8.4 Hz), 9.81 (bs, 1H), 10.29 (bs, 1H). (m/z): 460.7 (M+H).

Example 21

5'-[3-(3,5-dichloro-4-fluorophenyl)-3-(trifluoromethyl)pyrrolidin-1yl]-1-isobutyryl-3'H-spiro[azetidine-3,1'-[2]benzofuran

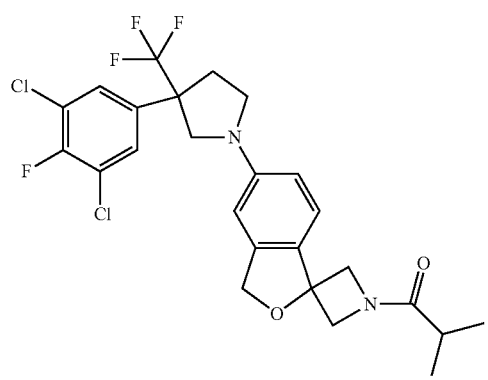 [SMILES: CC(C)C(=O)N1CC2(C1)OCc1cc(N3CCC(c4cc(Cl)c(F)c(Cl)c4)(C(F)(F)F)C3)ccc12]

To a stirred solution of 5'-[3-(3,5-dichloro-4-fluorophenyl)-3-(trifluoromethyl)pyrrolidin-1yl]-3'H-spiro[azetidine-3,1'-[2]benzofuran (Preparation 33, 0.3 g, 0.651 mmol) in dry DMF (2 mL) was added isobutyric acid (0.119 mL, 1.302 mmol) followed by addition of EDC.HCl (0.152 g, 0.976 mmol), HOBt (0.088 g, 0651 mmol) and triethyl amine (0.451 mL, 3.254 mmol) at room temperature. Resulting reaction mixture was stirred at room temperature for 16 hours. After complete consumption of starting material, reaction mixture was concentrated under reduced pressure to obtain brown liquid (0.350 g, crude). Crude compound was purified by column chromatography (100-200 mesh silica). Desired compound was eluted in 0.3% methanol in dichloromethane to afford product as brown solid (0.145 mg, 41.93%). $^1$H-NMR (400 MHz, CDCl$_3$) δ: 1.12-1.15 (m, 6H), 2.48-2.53 (m, 2H), 2.80-2.83 (m, 1H), 3.54-3.56 (m, 1H), 3.75-3.77 (m, 1H), 3.76 (d, 1H, J=10.24 Hz), 4.03 (d, 1H, J=10.32 Hz), 4.20-4.23 (m, 1H), 4.28-4.30 (m, 2H), 4.46 (d, 1H, J=9 Hz), 5.08 (s, 2H), 6.41 (d, 1H, J=1.64 Hz), 6.59 (dd, 1H, J$_1$=8.33 Hz, J$_2$=2.08 Hz), 7.25-7.28 (m, 1H), 7.34 (d, 2H, J=5.96 Hz). (m/z): 531.2 (M+H).

Example 22

1-(5-(3-(3,5-dichloro-4-fluorophenyl)-3-(trifluoromethyl)pyrrolidin-1-yl)-3'H-spiro[azetidine-3,1'-isobenzofuran]-1-yl)-2-(methylsulfonyl)ethanone

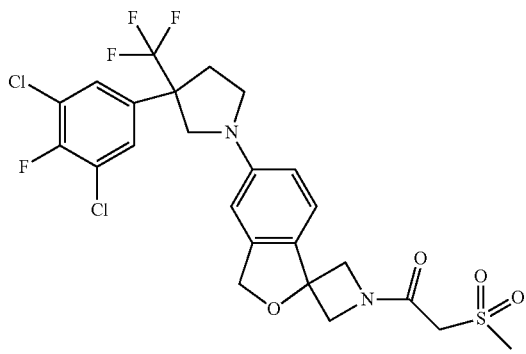 [SMILES: CS(=O)(=O)CC(=O)N1CC2(C1)OCc1cc(N3CCC(c4cc(Cl)c(F)c(Cl)c4)(C(F)(F)F)C3)ccc12]

This compound was prepared in an analogous manner to that of Example 21 except that methane sulfonyl acetic acid was used in place of isobutyric acid. $^1$H-NMR (400 MHz, CDCl$_3$) δ: 2.50-2.56 (m, 1H), 2.81-2.87 (m, 1H), 3.18 (s, 3H), 3.42-3.47 (m, 1H), 3.51-3.56 (m, 1H), 3.76 (d, 1H, J=10.12 Hz), 3.81-3.89 (m, 2H), 4.03 (d, 1H, J=10.48 Hz), 4.31 (d, 1H, J=10.88 Hz), 4.40 (d, 1H, J=11.08 Hz), 4.56-4.62 (m, 2H), 5.09 (s, 2H), 6.40 (s, 1H), 6.61 (dd, 1H, J$_1$=8.4 Hz, J$_2$=2 Hz), 7.33-7.37 (m, 3H). (m/z): 581.0 (M+H).

Preparation 34: 1-benzyl-3-(3,5-dichloro-phenyl)-3-trifluoromethyl-pyrrolidine

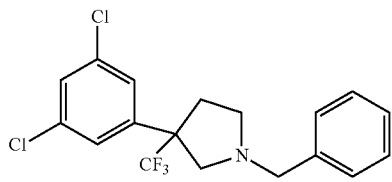 [SMILES: FC(F)(F)C1(c2cc(Cl)cc(Cl)c2)CCN(Cc2ccccc2)C1]

To a stirred solution of 1,3-dichloro-5-(1-trifluoromethyl-vinyl)-benzene (10 g, 41.49 mmol) in DCM (150 mL) was added benzyl-methoxymethyl-trimethylsilanylmethyl-amine (Preparation 29, 39.33 g, 165.97 mmol) at room temperature. Resulting reaction mixture was cooled to 0° C. and TFA (0.32 mL, 0.41) was added slowly and stirred at room temperature for 5 hours. After complete consumption of starting material, reaction mixture was basified by aqueous Na$_2$CO$_3$ and extracted with DCM (3×100 mL). Combined organic layer was dried over Na$_2$SO$_4$, and concentrated under vacuum to afford brown oil (9.5 g, crude). Crude compound was purified by column chromatography using 100-200 mesh silica gel. Desired product was eluted in 2% ethyl acetate in hexane to afford product as brown solid (7.5 g, 48.29%). $^1$H-NMR (400 MHz, CDCl$_3$) δ: 2.28-2.35 (m, 1H), 2.53-2.60 (m, 1H), 2.69-2.81 (m, 2H), 3.03-3.11 (m, 2H), 3.66 (s, 2H), 7.26-7.35 (m, 8H).

Preparation 35: 3-(3,5-dichloro-phenyl)-3-trifluoromethyl-pyrrolidine

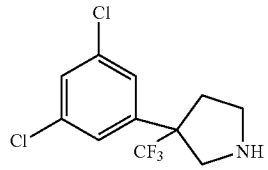

To a stirred solution of 1-benzyl-3-(3,5-dichloro-phenyl)-3-trifluoromethyl-pyrrolidine (Preparation 34, 7.5 g, 20.1 mmol) in 1.2-dichloroethane (50 mL) was added 1-chloroethyl chloroformate (3.87 mL, 36.19 mmol) at room temperature. Resulting reaction mixture was refluxed for 3 hours. After complete consumption of starting material, reaction mixture was concentrated under reduced pressure to afford brown thick oil, which was dissolved in MeOH (50 mL) and refluxed for 2 hours. After complete consumption of starting material, reaction mixture was concentrated in vacuo to afford brown oil, to which water was added (100 mL) and extracted with hexane (2×50 mL). Aqueous layer was basified by saturated sodium bicarbonate solution and extracted by ethyl acetate (3×50 mL). Combined organic layer was dried over anhydrous sodium sulfate, concentrated in vacuo to afford brown oil (7.5 g, crude). Crude compound was purified by column chromatography (100-200 mesh silica). Desired product was eluted in 25% ethyl acetate in hexane to afford product as brown oil (5.1 g, 89.32%). $^1$H-NMR (400 MHz, DMSO-d$_6$) δ: 2.33-2.39 (m, 1H), 2.40-2.45 (m, 1H), 2.85-2.98 (m, 2H), 3.34 (d, 1H, J=12.72 Hz), 3.52 (d, 1H, J=12.56 Hz), 7.28-7.34 (m, 1H), 7.46-7.52 (m, 2H), 7.64 (d, 1H J=1.25 Hz). (m/z): 284.0 (M+H).

Preparation 36: 5'-[3-(3,5-dichlorophenyl)-3-(trifluoromethyl)pyrrolidin-1yl]-1-tert-butyl 3'H-spiro[azetidine-3,1'-[2]benzofuran carbamate

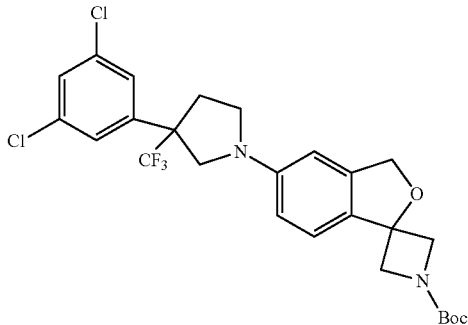 [SMILES: CC(C)(C)OC(=O)N1CC2(C1)OCc1cc(N3CCC(c4cc(Cl)cc(Cl)c4)(C(F)(F)F)C3)ccc12]

To a stirred solution of 3-(3,5-dichloro-phenyl)-3-trifluoromethyl-pyrrolidine (Preparation 35, 1 g, 3.534 mmol, 1 eq) in dry toluene (15 mL), tert-butyl 5'-bromo-3'H-spiro[azetidine-3,1'-isobenzofuran]-1-carboxylate (Intermediate 1) (1.081 g, 3.18 mmol, 0.9 eq) was added and reaction mixture was degassed for 30 minutes using nitrogen gas. Pd$_2$(dba)$_3$ chloroform adduct (0.073 g, 0.071 mmol, 0.02 eq), sodium tertiary butoxide (0.509 g, 5.3 mmol, 1.5 eq) and Xantphos (0.123 g, 0.212 mmol, 0.06 eq) was added. Resulting reaction mixture was refluxed for 6 hours. After complete consumption of starting material, reaction mixture was quenched by water (50 mL) and extracted with ethyl acetate (3×50 mL). Combined organic layer was dried over anhydrous sodium sulfate, and concentrated under reduced pressure to afford brown thick oil (2.1 g, crude). Crude compound was purified by column chromatography (100-200 mesh silica). Desired product was eluted in 12% ethyl acetate in hexane to give product as yellow oil (0.5 g, 26.18%). $^1$H-NMR (400 MHz, CDCl$_3$) δ: 1.46 (s, 9H), 2.51-2.55 (m, 1H), 2.81-2.87 (m, 1H), 3.45-3.48 (m, 1H), 3.51-3.55 (m, 1H), 3.77 (d, 1H J=10.32 Hz), 4.04 (d, 1H J=10.32 Hz), 4.10 (d, 2H, J=9.48 Hz), 4.27 (d, 2H, J=9.44 Hz), 5.06 (s, 2H), 6.39 (d, 1H, J=0.96 Hz), 6.59 (dd, 1H, J$_1$=8.4 Hz, J$_1$=2 Hz), 7.28 (s, 2H), 7.32 (d, 1H J=8.32 Hz), 7.37-7.38 (m, 1H). (m/z): 543.0 (M+H)

Preparation 37: 5'-[3-(3,5-dichlorophenyl)-3-(trifluoromethyl)pyrrolidin-1 yl]-3'H-spiro[azetidine-3,1'-[2]benzofuran

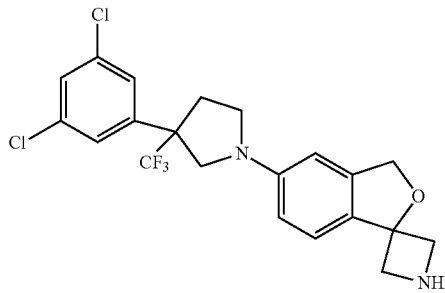 [SMILES: FC(F)(F)C1(c2cc(Cl)cc(Cl)c2)CCN(c2ccc3c(c2)COC32CNC2)C1]

To a stirred solution of 5'-[3-(3,5-dichlorophenyl)-3-(trifluoromethyl)-pyrrolidin-1yl]-1-tert-butyl 3'H-spiro[azetidine-3,1'-[2]benzofuran carbamate (Preparation 36, 0.6 g, 1.107 mmol) in MeOH (7 mL) and dry HCl gas was purged for 15 minutes at room temperature. After complete consumption of starting material, reaction mixture was concentrated under reduced pressure to afford faint brown semisolid, which was triturated with n-pentane (3×10 mL) to afford product as brown solid (0.4 g, crude). Crude compound was used as such for the next step. $^1$H-NMR (400 MHz, CDCl$_3$) δ: 2.55-2.57 (m, 1H), 2.82-2.88 (m, 1H), 3.45-3.47 (m, 1H), 3.51-3.55 (m, 1H), 3.77 (d, 1H, J=10.4 Hz), 4.03 (d, 1H, J=10.32 Hz), 4.35 (bs, 2H), 4.50 (bs, 2H), 5.06 (s, 2H), 6.37 (s 1H), 6.66 (d, 1H, J=7.96 Hz), 7.26 (s, 2H), 7.37 (d, 1H, J=1.56 Hz), 7.91 (d, 1H, J=8.28 Hz), 9.80 (bs, 1H), 10.28 (bs, 1H). (m/z): 442.9 (M+H).

Example 23

5'-[3-(3,5-dichlorophenyl)-3-(trifluoromethyl)pyrrolidine-1-yl]-1-[(methylsulfonyl)acetyl]-3'H-spiro[azitidine-3,1'-[2]benzofuran]

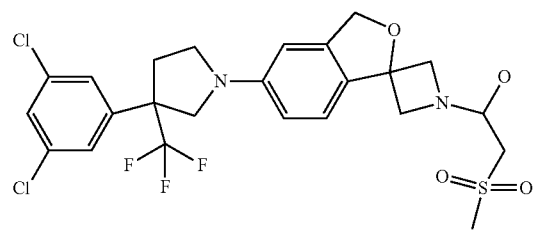 [SMILES: CS(=O)(=O)CC(O)N1CC2(C1)OCc1cc(N3CCC(c4cc(Cl)cc(Cl)c4)(C(F)(F)F)C3)ccc12]

To a stirred solution of 5'-[3-(3,5-dichlorophenyl)-3-(trifluoromethyl)-pyrrolidin-1yl]-3'H-spiro[azetidine-3,1'-[2]benzofuran: (Preparation 37, 0.5 g, 1.129 mmol) in dry DMF (5 mL) was added methane sulfonyl acetic acid (0.311 g, 2.257 mmol) followed by EDC.HCl (0.263 g, 1.693 mmol), HOBt (0.153 g, 1.129 mmol) and Et$_3$N (0.782 mL, 5.64 mmol) at room temperature. Resulting reaction mixture was stirred at room temperature for 16 hours. After complete consumption of starting material, reaction mixture was concentrated under reduced pressure to afford brown oil (1.2 g, crude). Crude compound was purified by column chromatography (100-200 mesh silica). Desired compound was eluted in 0.3% methanol in dichloromethane to afford product as off white solid (0.3 g, 47.18%). $^1$H-NMR (400 MHz, CDCl$_3$) δ: 2.55-2.57 (m, 1H), 2.82-2.88 (m, 1H), 3.18 (s, 3H), 3.45-3.46 (m, 1H), 3.53-3.55 (m, 1H), 3.77 (d, 1H, J=10.32 Hz), 3.84-3.85 (m, 2H), 4.04 (d, 1H, J=10.36 Hz), 4.29 (d, 1H, J=11.16 Hz), 4.39 (d, 1H, J=11.16 Hz), 4.56-4.62 (m, 2H), 5.09 (s, 2H), 6.40 (s 1H), 6.61 (dd, 1H, J$_1$=8.42 Hz, J$_2$=2 Hz), 7.27 (d, 2H, J=0.88 Hz), 7.34-7.38 (m, 2H). (m/z): 562.9 (M+H).

Example 24

5'-[3-(3,5-dichlorophenyl)-3-(trifluoromethyl)pyrrolidin-1yl]-1-isobutyryl-3'H-spiro[azetidine-3,1'-[2]benzofuran

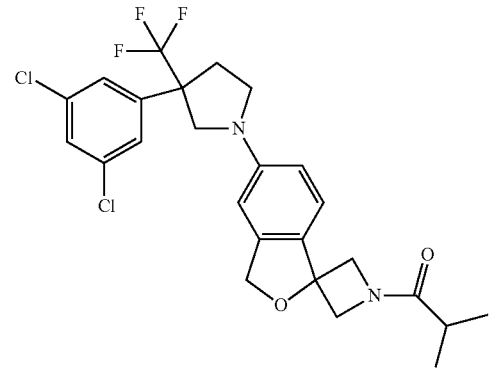 [SMILES: CC(C)C(=O)N1CC2(C1)OCc1cc(N3CCC(c4cc(Cl)cc(Cl)c4)(C(F)(F)F)C3)ccc12]

To a stirred solution of 5'-[3-(3,5-dichlorophenyl)-3-(trifluoromethyl)-pyrrolidin-1yl]-3'H-spiro[azetidine-3,1'-[2]benzofuran (Preparation 37, 0.2 g, 0.451 mmol) in dry DMF (5 mL) was added isobutyric acid (0.083 mL, 0.903 mmol) followed by EDC.HCl (0.106 g, 0.677 mmol), HOBt (0.061 g, 0.451 mmol) and Et₃N (0.313 mL, 2.25 mmol) at room temperature. Resulting reaction mixture was stirred at room temperature for 16 hours. After complete consumption of starting material, reaction mixture was concentrated under reduced pressure to afford brown oil (0.5 g, crude). Crude compound was purified by column chromatography (100-200 mesh silica). Desired compound was eluted in 0.4% methanol in dichloromethane to afford product as off white solid (0.175 g, 75.51%). ¹H-NMR (400 MHz, CDCl₃) δ: 1.09-1.15 (m, 6H), 2.47-2.55 (m, 2H), 2.82-2.87 (m, 1H), 3.46-3.48 (m, 1H), 3.53-3.55 (m, 1H), 3.77 (d, 1H, J=10.28 Hz), 4.04 (d, 1H, J=10.32 Hz), 4.22 (d, 1H, J=10.72 Hz), 4.28-4.32 (m, 2H), 4.46 (d, 1H, J=9 Hz), 5.08 (s, 2H), 6.41 (s, 1H), 6.59 (dd, 1H, J₁=8.34 Hz, J₂=1.96 Hz), 7.24-7.27 (m, 3H), 7.37-7.38 (m, 1H). (m/z): 513.2 (M+H).

Preparation 38: 1-benzyl-3-(3,4,5-trichloro-phenyl)-3-trifluoromethyl-pyrrolidine

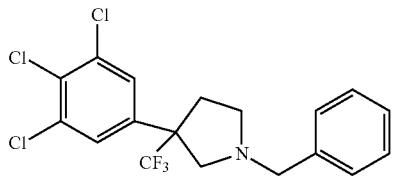 [SMILES: FC(F)(F)C1(c2cc(Cl)c(Cl)c(Cl)c2)CCN(Cc2ccccc2)C1]

To a stirred solution of 1,2,3-trichloro-5-(1-trifluoromethyl-vinyl)benzene (5 g, 18.21 mmol) in dry DCM (50 mL) was added benzyl-methoxymethyl-trimethylsilanylmethyl-amine (Preparation 29, 18.64 mL, 72.86 mmol). Resulting reaction mixture was cooled to 0° C. and TFA (0.14 mL, 1.825 mmol) was added slowly. Reaction mixture was stirred at room temperature for 5 hours. After complete consumption of starting material, reaction mixture was concentrated in vacuo to afford yellow thick oil, which was dissolved in ethyl acetate (50 mL) and washed with saturated sodium bicarbonate solution (3×50 mL). Organic layer was dried over anhydrous sodium sulfate, concentrated in vacuo to afford crude compound which was purified by column chromatography using 230-400 mesh silica to afford product as oily liquid (4.1 g, 55.11%). ¹H-NMR (400 MHz, CDCl₃) δ: 2.28-2.32 (m, 1H), 2.53-2.62 (m, 1H), 2.67-2.73 (m, 1H), 2.79-2.84 (m, 1H), 3.05 (s, 2H), 3.61-3.70 (m, 2H), 7.26-7.35 (m, 5H), 7.42 (s, 2H). (m/z): 407.9 (M+H).

Preparation 39: 3-(3,4,5-trichloro-phenyl)-3-trifluoromethyl-pyrrolidine

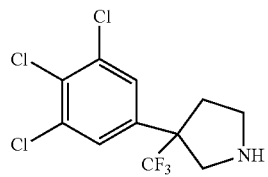 [SMILES: FC(F)(F)C1(c2cc(Cl)c(Cl)c(Cl)c2)CCNC1]

To a stirred solution of 1-benzyl-3-(3,4,5-trichloro-phenyl)-3-trifluoromethyl-pyrrolidine (Preparation 38, 4 g, 9.828 mmol) in 1,2-dichloroethane (40 mL) was added 1-chloroethyl chloroformate (1.91 mL, 17.69 mmol) and the resulting reaction mixture was refluxed for 3 hours. After complete consumption of starting material, reaction mixture was concentrated under reduced pressure to afford yellow oily residue, which was dissolved in MeOH (40 mL) and the mixture was refluxed at 2 hours. After complete consumption of starting material, reaction mixture was concentrated in vacuo to afford yellow oil, to which water (50 mL) was added and extracted with hexane (3×50 mL). Aqueous layer was basified using saturated sodium bicarbonate solution and extracted with ethyl acetate (3×50 mL). Combined organic layer was dried over anhydrous sodium sulfate and concentrated under reduced pressure to afford brown thick oil (5.5 g, crude). Crude compound was purified by column chromatography using 100-200 mesh silica gel. Desired compound was eluted in 4% methanol in dichloromethane to afford product as yellow thick oil (2.9 g, impure). Impure compound was as such for next reaction. (m/z): 317.9 (M+H).

Preparation 40: 1-tertbutyl-5'-[3-(3,4,5-trichlorophenyl)-3-(trifluoromethyl)pyrrolidin-1yl]-3'H-spiro[azetidine-3,1'-[2]benzofuran carbamate

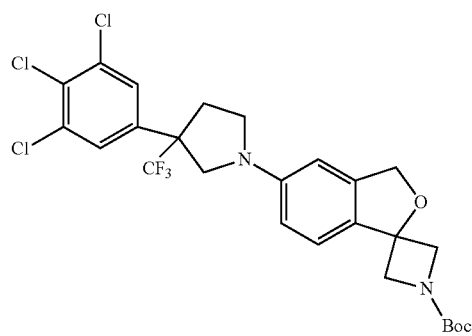 [SMILES: CC(C)(C)OC(=O)N1CC2(C1)OCc1cc(N3CCC(c4cc(Cl)c(Cl)c(Cl)c4)(C(F)(F)F)C3)ccc12]

To a stirred solution of 3-(3,4,5-trichloro-phenyl)-3-trifluoromethyl-pyrrolidine (Preparation 39, 2.4 g, 7.534 mmol) in dry toluene (28 mL) was added tert-butyl 5'-bromo-3'H-spiro[azetidine-3,1'-isobenzofuran]-1-carboxylate (2.305 g, 6.781 mmol, 0.9 eq) and reaction mixture was degassed for 30 minutes using nitrogen gas. Pd₂(dba)₃ chloroform adduct (0.156 g, 0.151 mmol) was added followed by sodium tertiary butoxide (1.085 g, 11.301 mmol) and Xantphos (0.262 g, 0.452 mmol). Resulting reaction mixture was refluxed for 12 hours. After complete consumption of starting material, reaction mixture was quenched by water (50 mL) and extracted with ethyl acetate (3×100 mL). Combined organic layer was dried over anhydrous sodium sulfate and concentrated under reduced pressure to afford brown thick oil (5.1 g, crude). Crude was purified by column chromatography using 100-200 mesh silica gel. Desired compound was eluted in 12% ethyl acetate in hexanes to afford product as yellow oil (1.2 g, impure). Impure compound was used as such for next reaction. ¹H-NMR (400 MHz, CDCl₃): 1.46 (S, 9H), 2.50-2.53 (m, 1H), 2.82-2.86 (m, 1H), 3.46-3.48 (m, 1H), 3.51-3.55 (m, 1H), 3.76 (d, 1H, J=10.2 Hz), 4.03 (d, 1H, J=10.28 Hz), 4.09 (d, 2H, J=9.56 Hz), 4.27 (d, 2H, J=9.56 Hz), 5.06 (S, 2H), 6.39 (S, 1H), 6.60 (dd, 1H, J1=2.08 Hz, J2=2.04 Hz), 7.32 (d, 1H, J=8.28 Hz), 7.41 (S, 2H). (m/z): 577.8 (M+H).

Preparation 41: 5'-[3-(3,4,5-trichlorophenyl)-3-(trifluoromethyl)pyrrolidin-1yl]-3'H-spiro[azetidine-3,1'-[2]benzofuran

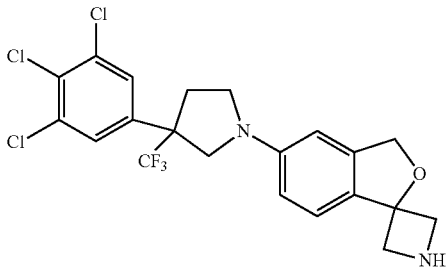 [SMILES: FC(F)(F)C1(c2cc(Cl)c(Cl)c(Cl)c2)CCN(c2ccc3c(c2)COC32CNC2)C1]

To a stirred solution of 1-tertbutyl-5'-[3-(3,4,5-trichlorophenyl)-3-(trifluoromethyl)pyrrolidin-1yl]-3'H-spiro[azetidine-3,1'-[2]benzofuran carbamate (Preparation 40, 1.3 g, 2.249 mmol) in MeOH (20 mL) was purged dry HCl gas for 15 minutes at room temperature. After complete consumption of starting material, the reaction mixture was concentrated under reduced pressure to afford faint brown semi solid, which was triturated with n-pentane (4×15 mL) to afford product as faint yellow solid (1.05 g, impure). Impure compound was used as it is for next reaction. $^1$H-NMR (400 MHz, DMSO-$d_6$) δ: 2.62-2.67 (m, 1H), 2.89-2.94 (m, 1H), 3.39-3.41 (m, 1H), 3.80 (d, 1H, J=11.32 Hz), 4.14-4.26 (m, 6H), 5.00 (s, 2H), 6.56 (s, 1H), 6.74 (d, 1H, J=8.48 Hz), 7.71 (d, 1H, J=8.4 Hz), 7.89 (s, 2H), 9.26 (bs 1H), 9.47 (bs 1H). (m/z): 476.8 (M+H).

Example 25

1-isobutyryl-5'-[3-(3,4,5-trichlorophenyl)-3-(trifluoromethyl)pyrrolidin-1yl]-3'H-spiro[azetidine-3,1'-[2]benzofuran

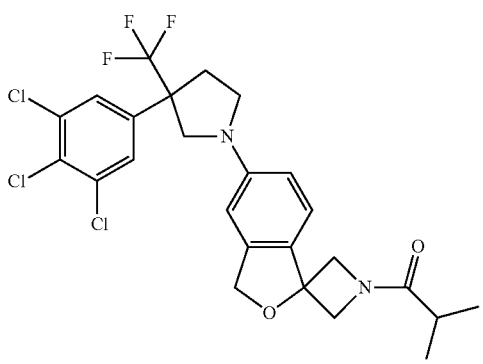 [SMILES: CC(C)C(=O)N1CC2(C1)OCc1cc(N3CCC(c4cc(Cl)c(Cl)c(Cl)c4)(C(F)(F)F)C3)ccc12]

To a stirred solution of 5'-[3-(3,4,5-trichlorophenyl)-3-(trifluoromethyl)-pyrrolidin-1yl]-3'H-spiro[azetidine-3,1'-[2]benzofuran (Preparation 41, 0.5 g, 1.048 mmol) in dry THF (10 mL) was added T$_3$P (1.572 mL, 5.241 mmol, 50% solution in ethyl acetate), DIPEA (1.834 mL, 10.48 mmol, 10 eq) and isobutyric acid (0.192 mL, 2.096 mmol) at room temperature. Resulting reaction mixture was stirred for 12 hours at room temperature. After complete consumption of starting material, reaction mixture was diluted with water (25 mL) and extracted with ethyl acetate (3×30 mL). Combined organic layer was dried over anhydrous sodium sulfate and concentrated under reduced pressure to obtain crude mass which was purified by column chromatography (100-200 mesh silica). Desired compound was eluted in 0.4% methanol in dichloromethane to afford product as off white solid (0.11 g, 19.3%). $^1$H-NMR (400 MHz, CDCl$_3$) δ: 1.14 (t, 6H J=6.56 Hz), 2.47-2.56 (m, 2H), 2.81-2.86 (m, 1H), 3.46-3.48 (m, 1H), 3.52-3.56 (m, 1H), 3.77 (d, 1H, J=10.28 Hz), 4.03 (d, 1H, J=10.28 Hz), 4.22 (d, 1H, J=10.68 Hz), 4.30 (t, 1H, J=10.76 Hz), 4.46 (d, 1H, J=9.24 Hz), 5.08 (s, 2H), 6.41 (s, 1H), 6.59 (d, 1H, J=8.52 Hz), 7.26-7.28 (m, 1H), 7.41 (s, 2H). (m/z): 546.8 (M+H).

Example 26

5'-[3-(3,4,5-trichloro)-3-(trifluoromethyl)pyrrolidin-1-yl]-1-[(methylsulfonyl)acetyl]-3'H-spiro[azetidine-3,1'-[2]benzofuran]

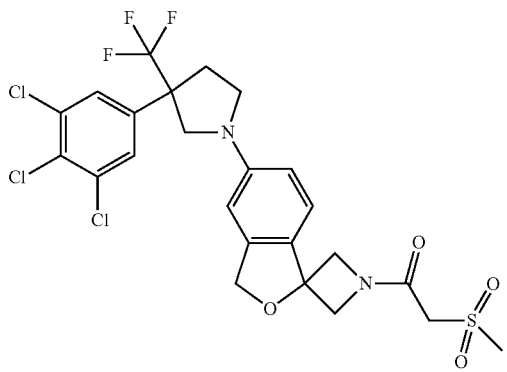 [SMILES: CS(=O)(=O)CC(=O)N1CC2(C1)OCc1cc(N3CCC(c4cc(Cl)c(Cl)c(Cl)c4)(C(F)(F)F)C3)ccc12]

This compound was prepared by using procedure similar to that of Example 25 using methane sulfonyl acetic acid in place of isobutyric acid. $^1$H-NMR (400 MHz, CDCl$_3$) δ: 2.49-2.55 (m, 1H), 2.80-2.88 (m, 1H), 3.18 (s, 3H), 3.45-3.49 (m, 1H), 3.50-3.56 (m, 1H), 3.76 (d, 1H, J=10.32 Hz), 3.80-3.90 (m, 2H), 4.03 (d, 1H, J=10.4 Hz), 4.31 (dd, 1H, J$_1$=1.12 Hz, J$_2$=10.96 Hz), 4.40 (d, 1H, J=11.24 Hz), 4.55-4.63 (m, 2H), 5.09 (s, 2H), 6.40 (d, 1H, J=1.64 Hz), 6.60 (dd, 1H, J$_1$=2.16 Hz, J$_2$=6.28 Hz), 7.36 (d, 1H, J=8.36 Hz), 7.41 (s, 2H). (m/z): 596.9 (M+H).

Preparation 42: tert-butyl 5'-formyl-3'H-spiro[azetidine-3,1'-isobenzofuran]-1-carboxylate

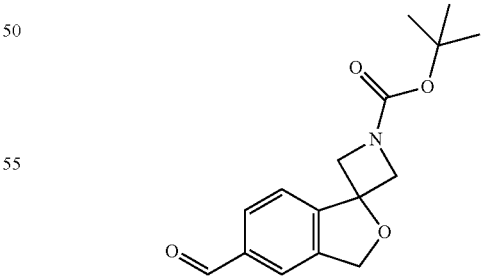

To a stirred solution of tert-butyl 5'-bromo-3'H-spiro[azetidine-3,1-isobenzofuran]-1-carboxylate (Intermediate 1, 2 g, 5.879 mmol, 1 eq) in dry THF (40 mL) was added n-BuLi (6.42 mL, 7.054 mmol, 1.2 eq) at −78° C. under nitrogen atmosphere. Reaction mixture was stirred for 10 minutes at −78° C. under nitrogen atmosphere. At −78° C., DMF (0.678 mL, 8.818 mmol, 1.5 eq) was added in drop wise manner over period of 10 minutes. Resulting reaction mixture was allowed to warm to −20° C. and stirred for 3 hours under nitrogen atmosphere. After complete consumption of starting material, reaction was quenched with 10% NH₄Cl solution (5 mL) followed by water (70 mL) and extracted with ethyl acetate (3×30 mL). Combined organic phase was washed with brine solution (50 mL), dried over anhydrous Na₂SO₄ and concentrated under reduced pressure to afford title compound as pale yellow thick oil (1.5 g, crude). Crude compound was used as such for next reaction. (m/z): 290.1 (M+H).

Preparation 43: tert-butyl 5'-((hydroxyimino)methyl)-3'H-spiro[azetidine-3,1-isobenzofuran]-1-carboxylate

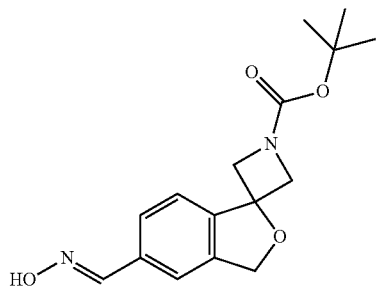 [SMILES: CC(C)(C)OC(=O)N1CC2(C1)OCc1cc(/C=N/O)ccc12]

To a stirred solution of tert-butyl 5'-formyl-3'H-spiro[azetidine-3,1-isobenzofuran]-1-carboxylate (Preparation 42, 1.5 g, 5.184 mmol, 1 eq) in mixture of methanol (20 mL) and water (10 mL) was added hydroxyl amine hydrochloride (0.537 g, 7.777 mmol, 1.5 eq) followed by addition of sodium acetate (0.765 g, 9.332 mmol, 1.8 eq) at room temperature. Resulting reaction mixture was stirred at room temperature for 24 hours. After complete consumption of starting material, reaction mixture was concentrated in vacuo to afforded yellow colored residue, which was diluted by water (70 mL) and extracted with ethyl acetate (3×30 mL). Combined organic phase was washed with brine solution (50 mL), dried over anhydrous Na₂SO₄ and concentrated under reduced pressure to get yellow semi solid (1.9 g, crude). Crude was purified by Combiflash using 40 g Redisep column. Desired compound was eluted in 24% ethyl acetate in hexane to afford title compound as yellow semi solid (1.1 g, 69.62%). ¹H NMR (400 MHz, CDCl₃) δ: 1.47 (s, 9H), 4.13 (d, J=9.6 Hz, 2H), 4.31 (d, J=9.84 Hz, 2H), 5.10 (s, 2H), 7.43 (s, 1H), 7.47 (d, J=7.88 Hz, 1H), 7.56 (d, J=7.92 Hz, 1H), 8.14 (s, 1H). (m/z): 303.3 (M−H).

Preparation 44: tert-butyl 5'-(5-(3,5-dichloro-4-fluorophenyl)-5-(trifluoromethyl)-1,4,2-dioxazol-3-yl)-3'H-spiro[azetidine-3,1'-isobenzofuran]-1-carboxylate

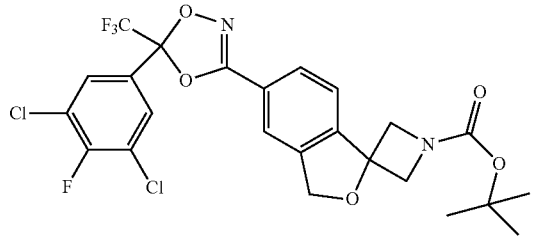 [SMILES: CC(C)(C)OC(=O)N1CC2(C1)OCc1cc(C3=NOC(c4cc(Cl)c(F)c(Cl)c4)(C(F)(F)F)O3)ccc12]

To a stirred solution of tert-butyl 5'-((hydroxyimino)methyl)-3'H-spiro[azetidine-3,1'-isobenzofuran]-1-carboxylate (Preparation 43) (0.5 g, 1.645 mmol, 1 eq) in DMF (6.5 mL) was added NCS (0.218 g, 1.645 mmol, 1 eq). Reaction mixture was stirred at 55° C. for 1 hour under nitrogen atmosphere. After 1 hour (chloro intermediate formation), 1-(3,5-dichloro-4-fluoro-phenyl)-2,2,2-trifluoro-ethanone (0.437 g, 1.678 mmol, 1.02 eq) was added followed by addition of sodium bicarbonate (0.140 g, 1.678 mmol, 1.02 eq) at room temperature. Resulting reaction mixture was stirred at 55° C. for 3 hours under nitrogen atmosphere. After complete consumption of starting material, reaction mixture was quenched by water (10 mL) and extracted with ethyl acetate (3×50 mL). Combined organic phase was washed with brine solution (20 mL), dried over anhydrous Na₂SO₄ and concentrated under reduced pressure to get brown thick oil (0.6 g, crude). Crude compound was purified by Combiflash using 40 g Redisep column. Desired compound was eluted in 25% ethyl acetate in hexane to afford title compound as colorless thick oil (0.33 g, impure). ¹H NMR (400 MHz, CDCl₃) δ: 1.46 (s, 9H), 4.11 (d, J=10.04 Hz, 2H), 4.32 (d, J=9.92 Hz, 2H), 5.15 (s, 2H), 7.56-7.58 (m, 1H), 7.64-7.68 (m, 3H), 7.86 (d, J=8.04 Hz, 1H), 8.02-8.04 (dd, J₁=6.12 Hz, J₂=0.64 Hz, 1H). LC-MS (m/z): No ionization.

Preparation 45: trifluoroacetic acid salt of 5'-(5-(3,5-dichloro-4-fluorophenyl)-5-(trifluoromethyl)-1,4,2-dioxazol-3-yl)-3'H-spiro[azetidine-3,1'-isobenzofuran]

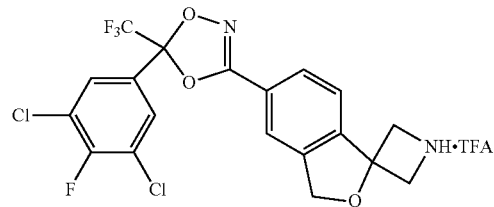

To a stirred solution of tert-butyl 5'-(5-(3,5-dichloro-4-fluorophenyl)-5-(trifluoromethyl)-1,4,2-dioxazol-3-yl)-3'H-spiro[azetidine-3,1'-isobenzofuran]-1-carboxylate (Preparation 44, 0.33 g, 0.586 mmol, 1 eq) in DCM (7 mL) was added trifluoro acetic acid (1.34 mL, 17.574 mmol, 30 eq) at 0° C. in drop wise manner over period of 15 minutes. Resulting reaction mixture was stirred at room temperature for 1 hour. After complete consumption of starting material, reaction mixture was concentrated in vacuo to afford brown thick oil, which was stripped out with chloroform (3×20 mL) to remove traces of trifluoro acetic acid under reduced pressure to afford title compound as brown thick oil (0.3 g, crude). Crude compound was used as such for the next reaction. LC-MS (m/z): 462.8 (M+H)

Example 27

1-(5'-(5-(3,5-dichloro-4-fluorophenyl)-5-(trifluoromethyl)-1,4,2-dioxazol-3-yl)-3'H-spiro[azetidine-3,1'-isobenzofuran]-1-yl)-2-(methylsulfonyl)ethanone

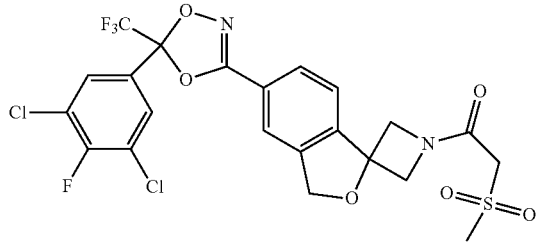 [SMILES: CS(=O)(=O)CC(=O)N1CC2(C1)OCc1cc(C3=NOC(c4cc(Cl)c(F)c(Cl)c4)(C(F)(F)F)O3)ccc12]

To a stirred solution of trifluoroacetic acid salt of 5'-(5-(3,5-dichloro-4-fluorophenyl)-5-(trifluoromethyl)-1,4,2-dioxazol-3-yl)-3'H-spiro[azetidine-3,1'-isobenzofuran](Preparation 45, 0.3 g, 0.648 mmol, 1 eq) in DMF (5 mL) was added triethyl amine (0.727 mL, 5.181mmol, 8 eq), followed by addition of EDC.HCl (0.185 g, 0.971 mmol, 1.5 eq), HOBt (0.087 g, 0.648 mmol, 1 eq) and methane sulfonyl acetic acid (0.178 g, 1.295 mmol, 2 eq) at room temperature. Resulting reaction mixture was stirred at room temperature for 18 hours under nitrogen atmosphere. After complete consumption of starting material, reaction mixture was quenched by water (50 mL) and extracted with ethyl acetate (3×30 mL). Combined organic phase was washed with saturated solution of LiCl solution (30 mL), brine (30 mL), dried over anhydrous $Na_2SO_4$ and concentrated under reduced pressure to get brown thick oil (0.48 g, crude). Crude was purified by combiflash using 40 g Redisep column. Desired compound was eluted in 52% ethyl acetate in hexane to afford title compound as off white solid (0.228 g, 60.35%). $^1$H NMR (400 MHz, $CDCl_3$) δ: 3.19 (s, 3H), 3.86 (s, 2H), 4.35 (d, J=11.16 Hz, 1H), 4.45 (d, J=11.16 Hz, 1H), 4.67 (t, J=10.72 Hz, 2H), 5.19 (s, 2H), 7.63-7.66 (m, 3H), 7.70 (s, 1H), 7.89 (d, J=8.08 Hz, 1H). (m/z): 580.9 (M−H), HPLC Purity: 95.78%.

Example 28

1-(5'-(5-(3,5-dichloro-4-fluorophenyl)-5-(trifluoromethyl)-1,4,2-dioxazol-3-yl)-3'H-spiro[azetidine-3,1'-isobenzofuran]-1-yl)-2-methyl propan-1-one

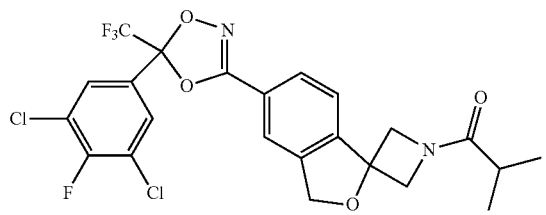 [SMILES: CC(C)C(=O)N1CC2(C1)OCc1cc(C3=NOC(c4cc(Cl)c(F)c(Cl)c4)(C(F)(F)F)O3)ccc12]

This compound was prepared in an analogous manner to that of Example 27 except that isobutyric acid was used in place of methane sulfonyl acetic acid. Yield=0.3 g (36.19%). $^1$H NMR (400 MHz, $CDCl_3$) δ: 1.15 (t, J=6.32 Hz, 6H), 2.47-2.54 (m, 1H), 4.25 (d, J=10.64 Hz, 1H), 4.31-4.39 (m, 2H), 4.53 (d, J=9.08 Hz, 1H), 5.18 (s, 2H), 7.52 (d, J=7.96 Hz, 1H), 7.65 (d, J=5.95 Hz, 2H), 7.70 (s, 1H), 7.87 (d, J=8.08 Hz, 1H). (m/z): 532.9 (M+H), HPLC Purity: 95.58%.

Example 29

1-(5-(5-(3,5-dichlorophenyl)-5-(trifluoromethyl)-1,4,2-dioxazol-3-yl)-3'H-spiro[azetidine-3,1'-isobenzofuran]-1-yl)-2-(methylsulfonyl)ethanone

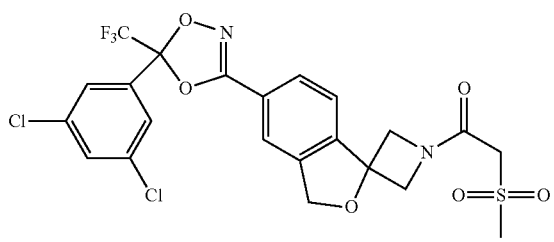 [SMILES: CS(=O)(=O)CC(=O)N1CC2(C1)OCc1cc(C3=NOC(c4cc(Cl)cc(Cl)c4)(C(F)(F)F)O3)ccc12]

This compound was prepared similarly to Example 27 except that 1-(3,5-dichloro-phenyl)-2,2,2-trifluoro-ethanone was used in place of 1-(3,5-dichloro-4-fluoro-phenyl)-2,2,2-trifluoro-ethanone. Yield=0.510 g (36.43%). $^1$H NMR (400 MHz, $CDCl_3$) δ: 3.19 (s, 3H), 3.86 (s, 2H), 4.35 (d, J=11.12 Hz, 1H), 4.45 (d, J=11.24 Hz, 1H), 4.64-4.70 (m, 2H), 5.19 (s, 2H), 7.50 (t, J=1.84 Hz, 1H), 7.56 (s, 2H), 7.64 (d, J=8.0 Hz, 1H), 7.71 (s, 1H), 7.89 (d, J=8.0 Hz, 1H). LC-MS (m/z): 562.8 (M−H), HPLC Purity: 98.32%.

Example 30

1-(5-(5-(3,5-dichlorophenyl)-5-(trifluoromethyl)-1,4,2-dioxazol-3-yl)-3'H-spiro[azetidine-3,1'-isobenzofuran]-1-yl)-2-methylpropan-1-one

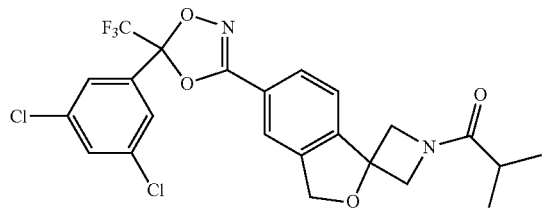 [SMILES: CC(C)C(=O)N1CC2(C1)OCc1cc(C3=NOC(c4cc(Cl)cc(Cl)c4)(C(F)(F)F)O3)ccc12]

This compound was prepared similarly to Example 29 except that isobutryic acid was used in place of methane sulfonyl acetic acid. Yield=0.310 g (24.41%). $^1$H NMR (400 MHz, $CDCl_3$) δ: 1.15 (d, J=6.76 Hz, 6H), 2.47-2.54 (m, 1H), 4.29 (d, J=9.68 Hz, 2H), 4.44 (bs, 2H), 5.18 (s, 2H), 7.50-7.53 (m, 2H), 7.56 (d, J=1.72 Hz, 2H), 7.71 (s, 1H), 7.88 (d, J=7.76 Hz, 1H). (m/z): 514.9 (M+H), HPLC Purity: 98.76%.

Example 31

1-(5'-(5-(3,4,5-trichlorophenyl)-5-(trifluoromethyl)-1,4,2-dioxazol-3-yl)-3'H-spiro[azetidine-3,1'-isobenzofuran]-1-yl)propan-1-one

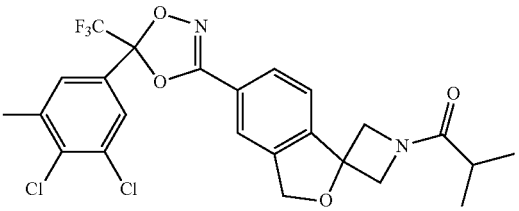

This compound was prepared similarly to Example 30 except that 1-(3,4,5-trichloro-phenyl)-2,2,2-trifluoro-ethanone was used in place of 1-(3,5-dichloro-phenyl)-2,2,2-trifluoro-ethanone. Yield=0.285 g (31.67%). $^1$H NMR (400 MHz, $CDCl_3$) δ: 1.13 (t, J=16.4 Hz, 6H), 2.45-2.55 (m, 1H), 4.25 (d, J=10.68 Hz, 1H), 4.31-4.39 (m, 2H), 4.53 (d, J=9.08 Hz, 1H), 5.18 (s, 2H), 7.52 (d, J=7.96 Hz, 1H), 7.70 (d, J=4.92 Hz, 3H), 7.87 (d, J=8.04 Hz, 1H). (m/z): 548.9 (M+H), HPLC Purity: 97.17%.

Example 32

2-(methylsulfonyl)-1-(5'-(5-(3,4,5-trichlorophenyl)-5-(trifluoro methyl)-1,4,2-dioxazol-3-yl)-3'H-spiro[azetidine-3,1'-isobenzofuran]-1-yl)ethanone

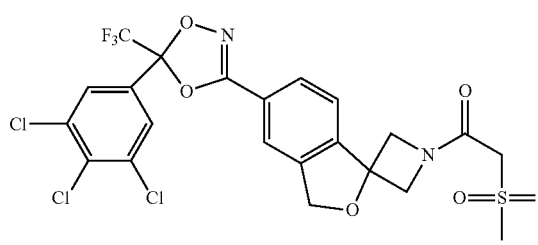

This compound was prepared similarly to Example 27 except that 1-(3,4,5-trichloro-phenyl)-2,2,2-trifluoro-ethanone was used in place of 1-(3,5-dichloro-4-fluoro-phenyl)-2,2,2-trifluoro-ethanone. Yield: 0.285 g (29.08%). $^1$H NMR (400 MHz, CDCl$_3$) δ: 3.18 (s, 3H), 3.86 (s, 2H), 4.35 (d, J=11.2 Hz, 1H), 4.45 (d, J=11.16 Hz, 1H), 4.64-4.70 (m, 2H), 5.18 (s, 2H), 7.65 (d, J=8 Hz, 1H), 7.70 (d, J=5.92 Hz, 3H), 7.88 (d, J=8.04 Hz, 1H). (m/z): 598.6 (M+H), HPLC Purity: 97.05%.

By the methods described herein, the following spirocyclic dihydrofuranyls of Table 1 (Examples 33-92) can be prepared from Formula (1.2A).

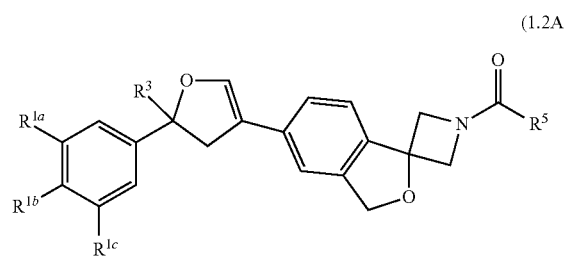

(1.2A)

For Table 1 compounds, $R^3$ is trifluoromethyl.

TABLE 1

Spirocyclic Dihydrofuranyls

| Example No. | $R^{1a}$ | $R^{1b}$ | $R^{1c}$ | $R^5$ |
|---|---|---|---|---|
| 33 | Cl | Cl | Cl | Methyl |
| 34 | Cl | H | Cl | Methyl |
| 35 | Cl | F | Cl | Methyl |
| 36 | Cl | Cl | Cl | Ethyl |
| 37 | Cl | H | Cl | Ethyl |
| 38 | Cl | F | Cl | Ethyl |
| 39 | Cl | Cl | Cl | Propyl |
| 40 | Cl | H | Cl | Propyl |
| 41 | Cl | F | Cl | Propyl |
| 42 | Cl | Cl | Cl | Isobutyl |
| 43 | Cl | H | Cl | Isobutyl |
| 44 | Cl | F | Cl | Isobutyl |
| 45 | Cl | Cl | Cl | CH$_2$OH |
| 46 | Cl | H | Cl | CH$_2$OH |
| 47 | Cl | F | Cl | CH$_2$OH |
| 48 | Cl | Cl | Cl | Cyclopropyl |
| 49 | Cl | H | Cl | Cyclopropyl |
| 50 | Cl | F | Cl | Cyclopropyl |
| 51 | Cl | Cl | Cl | Cyclobutyl |
| 52 | Cl | H | Cl | Cyclobutyl |
| 53 | Cl | F | Cl | Cyclobutyl |
| 54 | Cl | Cl | Cl | CH$_2$—cyclopropyl |
| 55 | Cl | H | Cl | CH$_2$—cyclopropyl |
| 56 | Cl | F | Cl | CH$_2$—cyclopropyl |
| 57 | Cl | Cl | Cl | CH$_2$—cyclobutyl |
| 58 | Cl | H | Cl | CH$_2$—cyclobutyl |
| 59 | Cl | F | Cl | CH$_2$—cyclobutyl |
| 60 | Cl | Cl | Cl | CH$_2$CF$_3$ |
| 61 | Cl | H | Cl | CH$_2$CF$_3$ |
| 62 | Cl | F | Cl | CH$_2$CF$_3$ |
| 63 | Cl | Cl | Cl | —CH$_2$SCH$_3$ |
| 64 | Cl | H | Cl | —CH$_2$SCH$_3$ |
| 65 | Cl | F | Cl | —CH$_2$SCH$_3$ |
| 66 | Cl | Cl | Cl | thietanyl |
| 67 | Cl | H | Cl | thietanyl |
| 68 | Cl | F | Cl | thietanyl |
| 69 | Cl | Cl | Cl | thietanyl S-oxide |
| 70 | Cl | H | Cl | thietanyl S-oxide |
| 71 | Cl | F | Cl | thietanyl S-oxide |
| 72 | Cl | Cl | Cl | thietanyl S,S-dioxide |
| 73 | Cl | H | Cl | thietanyl S,S-dioxide |
| 74 | Cl | F | Cl | thietanyl S,S-dioxide |
| 75 | Cl | Cl | Cl | cyclopropyl-OH |
| 76 | Cl | H | Cl | cyclopropyl-OH |

TABLE 1-continued

Spirocyclic Dihydrofuranyls

| Example No. | $R^{1a}$ | $R^{1b}$ | $R^{1c}$ | $R^5$ |
|---|---|---|---|---|
| 77 | Cl | F | Cl | cyclopropyl-OH |
| 78 | Cl | Cl | Cl | CH2-pyrazol-1-yl |
| 79 | Cl | H | Cl | CH2-pyrazol-1-yl |
| 80 | Cl | F | Cl | CH2-pyrazol-1-yl |
| 81 | Cl | Cl | Cl | 1-(CF3)cyclopropyl |
| 82 | Cl | H | Cl | 1-(CF3)cyclopropyl |
| 83 | Cl | F | Cl | 1-(CF3)cyclopropyl |
| 84 | Cl | Cl | Cl | CH2-(3-methylpyrazol-1-yl) |
| 85 | Cl | H | Cl | CH2-(3-methylpyrazol-1-yl) |
| 86 | Cl | F | Cl | CH2-(3-methylpyrazol-1-yl) |
| 87 | Cl | Cl | Cl | 2,2-difluorocyclopropyl |
| 88 | Cl | H | Cl | 2,2-difluorocyclopropyl |
| 89 | Cl | F | Cl | 2,2-difluorocyclopropyl |
| 90 | Cl | Cl | Cl | CH2-(pyridin-2-yl) |
| 91 | Cl | H | Cl | CH2-(pyridin-2-yl) |
| 92 | Cl | F | Cl | CH2-(pyridin-2-yl) |

By the methods described herein, the following spirocyclic dihydropyrrolyls of Table 2 (Examples 93-152) can be prepared from Formula (2.2A).

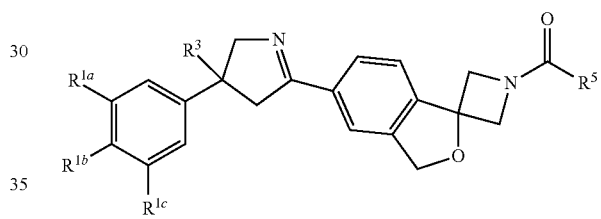

(2.2A)

For Table 2: $R^3$ is trifluoromethyl.

TABLE 2

Spirocyclic Dihyrdropyrrrolyls

| Example No. | $R^{1a}$ | $R^{1b}$ | $R^{1c}$ | $R^5$ |
|---|---|---|---|---|
| 93 | Cl | Cl | Cl | Methyl |
| 94 | Cl | H | Cl | Methyl |
| 95 | Cl | F | Cl | Methyl |
| 96 | Cl | Cl | Cl | Ethyl |
| 97 | Cl | H | Cl | Ethyl |
| 98 | Cl | F | Cl | Ethyl |
| 99 | Cl | Cl | Cl | Propyl |
| 100 | Cl | H | Cl | Propyl |
| 101 | Cl | F | Cl | Propyl |
| 102 | Cl | Cl | Cl | Isobutyl |
| 103 | Cl | H | Cl | Isobutyl |
| 104 | Cl | F | Cl | Isobutyl |
| 105 | Cl | Cl | Cl | $CH_2OH$ |
| 106 | Cl | H | Cl | $CH_2OH$ |
| 107 | Cl | F | Cl | $CH_2OH$ |
| 108 | Cl | Cl | Cl | Cyclopropyl |
| 109 | Cl | H | Cl | Cyclopropyl |
| 110 | Cl | F | Cl | Cyclopropyl |
| 111 | Cl | Cl | Cl | Cyclobutyl |
| 112 | Cl | H | Cl | Cyclobutyl |
| 113 | Cl | F | Cl | Cyclobutyl |
| 114 | Cl | Cl | Cl | $CH_2$—cyclopropyl |
| 115 | Cl | H | Cl | $CH_2$—cyclopropyl |
| 116 | Cl | F | Cl | $CH_2$—cyclopropyl |
| 117 | Cl | Cl | Cl | $CH_2$—cyclobutyl |
| 118 | Cl | H | Cl | $CH_2$—cyclobutyl |

TABLE 2-continued

Spirocyclic Dihyrdropyrrrolyls

| Example No. | $R^{1a}$ | $R^{1b}$ | $R^{1c}$ | $R^5$ |
|---|---|---|---|---|
| 119 | Cl | F | Cl | CH$_2$—cyclobutyl |
| 120 | Cl | Cl | Cl | CH$_2$CF$_3$ |
| 121 | Cl | H | Cl | CH$_2$CF$_3$ |
| 122 | Cl | F | Cl | CH$_2$CF$_3$ |
| 123 | Cl | Cl | Cl | —CH$_2$SCH$_3$ |
| 124 | Cl | H | Cl | —CH$_2$SCH$_3$ |
| 125 | Cl | F | Cl | —CH$_2$SCH$_3$ |
| 126 | Cl | Cl | Cl | thietanyl |
| 127 | Cl | H | Cl | thietanyl |
| 128 | Cl | F | Cl | thietanyl |
| 129 | Cl | Cl | Cl | thietane S-oxide |
| 130 | Cl | H | Cl | thietane S-oxide |
| 131 | Cl | F | Cl | thietane S-oxide |
| 132 | Cl | Cl | Cl | thietane S,S-dioxide |
| 133 | Cl | H | Cl | thietane S,S-dioxide |
| 134 | Cl | F | Cl | thietane S,S-dioxide |
| 135 | Cl | Cl | Cl | 1-hydroxycyclopropyl |
| 136 | Cl | H | Cl | 1-hydroxycyclopropyl |
| 137 | Cl | F | Cl | 1-hydroxycyclopropyl |
| 138 | Cl | Cl | Cl | CH$_2$-pyrazol-1-yl |
| 139 | Cl | H | Cl | CH$_2$-pyrazol-1-yl |
| 140 | Cl | F | Cl | CH$_2$-pyrazol-1-yl |
| 141 | Cl | Cl | Cl | 1-(CF$_3$)cyclopropyl |
| 142 | Cl | H | Cl | 1-(CF$_3$)cyclopropyl |
| 143 | Cl | F | Cl | 1-(CF$_3$)cyclopropyl |
| 144 | Cl | Cl | Cl | CH$_2$-(3-methylpyrazol-1-yl) |
| 145 | Cl | H | Cl | CH$_2$-(3-methylpyrazol-1-yl) |
| 146 | Cl | F | Cl | CH$_2$-(3-methylpyrazol-1-yl) |
| 147 | Cl | Cl | Cl | 2,2-difluorocyclopropyl |
| 148 | Cl | H | Cl | 2,2-difluorocyclopropyl |
| 149 | Cl | F | Cl | 2,2-difluorocyclopropyl |
| 150 | Cl | Cl | Cl | CH$_2$-pyridin-2-yl |

TABLE 2-continued

Spirocyclic Dihyrdropyrrrolyls

| Example No. | $R^{1a}$ | $R^{1b}$ | $R^{1c}$ | $R^5$ |
|---|---|---|---|---|
| 151 | Cl | H | Cl | 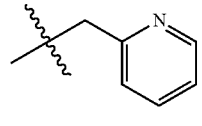 [SMILES: *Cc1ccccn1] |
| 152 | Cl | F | Cl | (2-pyridylmethyl) |

By the methods described herein, the following spirocyclic pyrrolidinyls of Table 3 (Examples 153-212) can be prepared from Formula (3.2A).

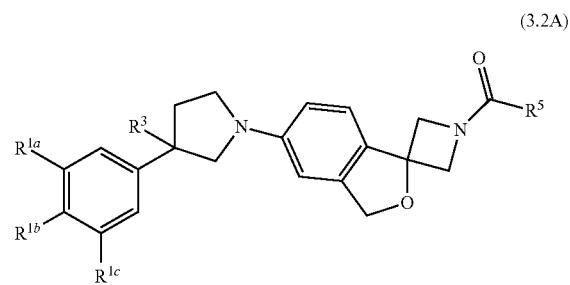

(3.2A)

For Table 3: $R^3$ is trifluoromethyl.

TABLE 3

Spirocyclic Pyrrolidinyls

| Example No. | $R^{1a}$ | $R^{1b}$ | $R^{1c}$ | $R^5$ |
|---|---|---|---|---|
| 153 | Cl | Cl | Cl | Methyl |
| 154 | Cl | H | Cl | Methyl |
| 155 | Cl | F | Cl | Methyl |
| 156 | Cl | Cl | Cl | Ethyl |
| 157 | Cl | H | Cl | Ethyl |
| 158 | Cl | F | Cl | Ethyl |
| 159 | Cl | Cl | Cl | Propyl |
| 160 | Cl | H | Cl | Propyl |
| 161 | Cl | F | Cl | Propyl |
| 162 | Cl | Cl | Cl | Isobutyl |
| 163 | Cl | H | Cl | Isobutyl |
| 164 | Cl | F | Cl | Isobutyl |
| 165 | Cl | Cl | Cl | $CH_2OH$ |
| 166 | Cl | H | Cl | $CH_2OH$ |
| 167 | Cl | F | Cl | $CH_2OH$ |
| 168 | Cl | Cl | Cl | Cyclopropyl |
| 169 | Cl | H | Cl | Cyclopropyl |
| 170 | Cl | F | Cl | Cyclopropyl |
| 171 | Cl | Cl | Cl | Cyclobutyl |
| 172 | Cl | H | Cl | Cyclobutyl |
| 173 | Cl | F | Cl | Cyclobutyl |
| 174 | Cl | Cl | Cl | $CH_2$—cyclopropyl |
| 175 | Cl | H | Cl | $CH_2$—cyclopropyl |
| 176 | Cl | F | Cl | $CH_2$—cyclopropyl |
| 177 | Cl | Cl | Cl | $CH_2$—cyclobutyl |
| 178 | Cl | H | Cl | $CH_2$—cyclobutyl |
| 179 | Cl | F | Cl | $CH_2$—cyclobutyl |
| 180 | Cl | Cl | Cl | $CH_2CF_3$ |
| 181 | Cl | H | Cl | $CH_2CF_3$ |
| 182 | Cl | F | Cl | $CH_2CF_3$ |
| 183 | Cl | Cl | Cl | —$CH_2SCH_3$ |

TABLE 3-continued

Spirocyclic Pyrrolidinyls

| Example No. | $R^{1a}$ | $R^{1b}$ | $R^{1c}$ | $R^5$ |
|---|---|---|---|---|
| 184 | Cl | H | Cl | —$CH_2SCH_3$ |
| 185 | Cl | F | Cl | —$CH_2SCH_3$ |
| 186 | Cl | Cl | Cl | (thietanyl) |
| 187 | Cl | H | Cl | (thietanyl) |
| 188 | Cl | F | Cl | (thietanyl) |
| 189 | Cl | Cl | Cl | (thietanyl S=O) |
| 190 | Cl | H | Cl | (thietanyl S=O) |
| 191 | Cl | F | Cl | (thietanyl S=O) |
| 192 | Cl | Cl | Cl | (thietanyl $SO_2$) |
| 193 | Cl | H | Cl | (thietanyl $SO_2$) |
| 194 | Cl | F | Cl | (thietanyl $SO_2$) |
| 195 | Cl | Cl | Cl | (hydroxycyclopropyl) |
| 196 | Cl | H | Cl | (hydroxycyclopropyl) |
| 197 | Cl | F | Cl | (hydroxycyclopropyl) |
| 198 | Cl | Cl | Cl | 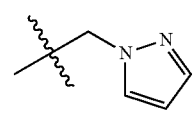 [SMILES: *Cn1cccn1] |

TABLE 3-continued

Spirocyclic Pyrrolidinyls

| Example No. | $R^{1a}$ | $R^{1b}$ | $R^{1c}$ | $R^5$ |
|---|---|---|---|---|
| 199 | Cl | H | Cl | pyrazol-1-ylmethyl |
| 200 | Cl | F | Cl | pyrazol-1-ylmethyl |
| 201 | Cl | Cl | Cl | 1-(trifluoromethyl)cyclopropyl |
| 202 | Cl | H | Cl | 1-(trifluoromethyl)cyclopropyl |
| 203 | Cl | F | Cl | 1-(trifluoromethyl)cyclopropyl |
| 204 | Cl | Cl | Cl | (3-methyl-1H-pyrazol-1-yl)methyl |
| 205 | Cl | H | Cl | (3-methyl-1H-pyrazol-1-yl)methyl |
| 206 | Cl | F | Cl | (3-methyl-1H-pyrazol-1-yl)methyl |
| 207 | Cl | Cl | Cl | 2,2-difluorocyclopropyl |
| 208 | Cl | H | Cl | 2,2-difluorocyclopropyl |
| 209 | Cl | F | Cl | 2,2-difluorocyclopropyl |
| 210 | Cl | Cl | Cl | pyridin-2-ylmethyl |
| 211 | Cl | H | Cl | pyridin-2-ylmethyl |
| 212 | Cl | F | Cl | pyridin-2-ylmethyl |

By the methods described herein, the following spirocyclic dihydropyrazolyls of Table 4 (Examples 213-273) can be prepared from Formula (6.2A).

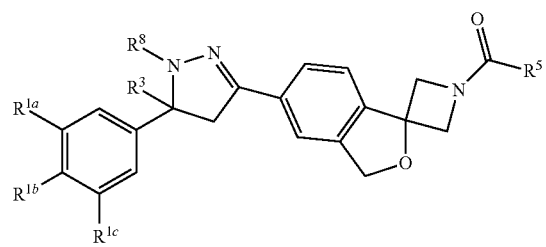

(6.2A)

For Table 4: $R^3$ is trifluoromethyl and $R^8$ is H.

TABLE 4

Spirocyclic Dihydropyrazolyls

| Example No. | $R^{1a}$ | $R^{1b}$ | $R^{1c}$ | $R^5$ |
|---|---|---|---|---|
| 213 | Cl | Cl | Cl | Methyl |
| 214 | Cl | H | Cl | Methyl |
| 215 | Cl | F | Cl | Methyl |
| 216 | Cl | Cl | Cl | Ethyl |
| 217 | Cl | H | Cl | Ethyl |
| 218 | Cl | F | Cl | Ethyl |
| 219 | Cl | Cl | Cl | Propyl |
| 220 | Cl | H | Cl | Propyl |
| 221 | Cl | F | Cl | Propyl |
| 222 | Cl | Cl | Cl | Isobutyl |
| 223 | Cl | H | Cl | Isobutyl |
| 224 | Cl | F | Cl | Isobutyl |
| 225 | Cl | Cl | Cl | $CH_2OH$ |
| 226 | Cl | H | Cl | $CH_2OH$ |
| 227 | Cl | F | Cl | $CH_2OH$ |
| 228 | Cl | Cl | Cl | Cyclopropyl |
| 229 | Cl | H | Cl | Cyclopropyl |
| 230 | Cl | F | Cl | Cyclopropyl |
| 231 | Cl | Cl | Cl | Cyclobutyl |
| 232 | Cl | H | Cl | Cyclobutyl |
| 233 | Cl | F | Cl | Cyclobutyl |
| 234 | Cl | Cl | Cl | $CH_2$—cyclopropyl |
| 235 | Cl | H | Cl | $CH_2$—cyclopropyl |
| 236 | Cl | F | Cl | $CH_2$—cyclopropyl |
| 237 | Cl | Cl | Cl | $CH_2$—cyclobutyl |
| 238 | Cl | H | Cl | $CH_2$—cyclobutyl |
| 239 | Cl | F | Cl | $CH_2$—cyclobutyl |
| 240 | Cl | Cl | Cl | $CH_2CF_3$ |
| 241 | Cl | H | Cl | $CH_2CF_3$ |
| 242 | Cl | F | Cl | $CH_2CF_3$ |
| 243 | Cl | Cl | Cl | —$CH_2SCH_3$ |
| 244 | Cl | H | Cl | —$CH_2SCH_3$ |
| 245 | Cl | F | Cl | —$CH_2SCH_3$ |
| 246 | Cl | Cl | Cl | —$CH_2S(O)CH_3$ |

TABLE 4-continued

Spirocyclic Dihydropyrazolyls

| Example No. | R¹ᵃ | R¹ᵇ | R¹ᶜ | R⁵ |
|---|---|---|---|---|
| 247 | Cl | Cl | Cl | thietane |
| 248 | Cl | H | Cl | thietane |
| 249 | Cl | F | Cl | thietane |
| 250 | Cl | Cl | Cl | thietane S-oxide |
| 251 | Cl | H | Cl | thietane S-oxide |
| 252 | Cl | F | Cl | thietane S-oxide |
| 253 | Cl | Cl | Cl | thietane S,S-dioxide |
| 254 | Cl | H | Cl | thietane S,S-dioxide |
| 255 | Cl | F | Cl | thietane S,S-dioxide |
| 256 | Cl | Cl | Cl | cyclopropyl-OH |
| 257 | Cl | H | Cl | cyclopropyl-OH |
| 258 | Cl | F | Cl | cyclopropyl-OH |
| 259 | Cl | Cl | Cl | CH₂-pyrazol-1-yl |
| 260 | Cl | H | Cl | CH₂-pyrazol-1-yl |
| 261 | Cl | F | Cl | CH₂-pyrazol-1-yl |
| 262 | Cl | Cl | Cl | 1-CF₃-cyclopropyl |
| 263 | Cl | H | Cl | 1-CF₃-cyclopropyl |
| 264 | Cl | F | Cl | 1-CF₃-cyclopropyl |
| 265 | Cl | Cl | Cl | CH₂-(3-methylpyrazol-1-yl) |
| 266 | Cl | H | Cl | CH₂-(3-methylpyrazol-1-yl) |
| 267 | Cl | F | Cl | CH₂-(3-methylpyrazol-1-yl) |
| 268 | Cl | Cl | Cl | 2,2-difluorocyclopropyl |
| 269 | Cl | H | Cl | 2,2-difluorocyclopropyl |
| 270 | Cl | F | Cl | 2,2-difluorocyclopropyl |
| 271 | Cl | Cl | Cl | CH₂-pyridin-2-yl |
| 272 | Cl | H | Cl | CH₂-pyridin-2-yl |

TABLE 4-continued

Spirocyclic Dihydropyrazolyls

| Example No. | $R^{1a}$ | $R^{1b}$ | $R^{1c}$ | $R^5$ |
|---|---|---|---|---|
| 273 | Cl | F | Cl | 2-pyridylmethyl (gem-dimethyl) |

By the methods described herein, the following spirocyclic dihydropyrazolyls of Table 5 (Examples 274-339) can be prepared from Formula (6.2A).

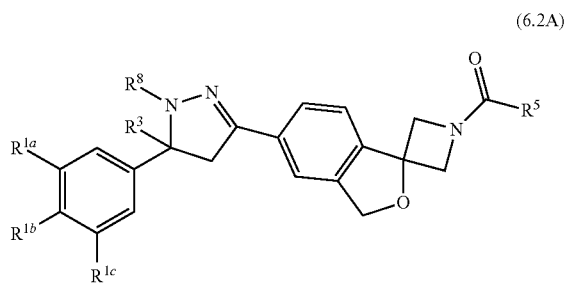

(6.2A)

For Table 5: $R^3$ is trifluoromethyl and $R^8$ is methyl.

TABLE 5

Spirocyclic Dihydropyrazolyls

| Example No. | $R^{1a}$ | $R^{1b}$ | $R^{1c}$ | $R^5$ |
|---|---|---|---|---|
| 274 | Cl | Cl | Cl | Methyl |
| 275 | Cl | H | Cl | Methyl |
| 276 | Cl | F | Cl | Methyl |
| 277 | Cl | Cl | Cl | Ethyl |
| 278 | Cl | H | Cl | Ethyl |
| 279 | Cl | F | Cl | Ethyl |
| 280 | Cl | Cl | Cl | Propyl |
| 281 | Cl | H | Cl | Propyl |
| 282 | Cl | F | Cl | Propyl |
| 283 | Cl | Cl | Cl | Isopropyl |
| 284 | Cl | H | Cl | Isopropyl |
| 285 | Cl | Cl | Cl | Isobutyl |
| 286 | Cl | H | Cl | Isobutyl |
| 287 | Cl | F | Cl | Isobutyl |
| 288 | Cl | Cl | Cl | $CH_2OH$ |
| 289 | Cl | H | Cl | $CH_2OH$ |
| 290 | Cl | F | Cl | $CH_2OH$ |
| 291 | Cl | Cl | Cl | Cyclopropyl |
| 292 | Cl | H | Cl | Cyclopropyl |
| 293 | Cl | F | Cl | Cyclopropyl |
| 294 | Cl | Cl | Cl | Cyclobutyl |
| 295 | Cl | H | Cl | Cyclobutyl |
| 296 | Cl | F | Cl | Cyclobutyl |
| 297 | Cl | Cl | Cl | $CH_2$—cyclopropyl |
| 298 | Cl | H | Cl | $CH_2$—cyclopropyl |
| 299 | Cl | F | Cl | $CH_2$—cyclopropyl |
| 300 | Cl | Cl | Cl | $CH_2$—cyclobutyl |
| 301 | Cl | H | Cl | $CH_2$—cyclobutyl |
| 302 | Cl | F | Cl | $CH_2$—cyclobutyl |
| 303 | Cl | Cl | Cl | $CH_2CF_3$ |
| 304 | Cl | H | Cl | $CH_2CF_3$ |
| 305 | Cl | F | Cl | $CH_2CF_3$ |
| 306 | Cl | Cl | Cl | —$CH_2SCH_3$ |
| 307 | Cl | H | Cl | —$CH_2SCH_3$ |
| 308 | Cl | F | Cl | —$CH_2SCH_3$ |
| 309 | Cl | Cl | Cl | —$CH_2S(O)CH_3$ |
| 310 | Cl | H | Cl | —$CH_2S(O)CH_3$ |
| 311 | Cl | Cl | Cl | —$CH_2S(O)_2CH_3$ |
| 312 | Cl | H | Cl | —$CH_2S(O)_2CH_3$ |
| 313 | Cl | Cl | Cl | thietanyl |
| 314 | Cl | H | Cl | thietanyl |
| 315 | Cl | F | Cl | thietanyl |
| 316 | Cl | Cl | Cl | thietanyl S-oxide |
| 317 | Cl | H | Cl | thietanyl S-oxide |
| 318 | Cl | F | Cl | thietanyl S-oxide |
| 319 | Cl | Cl | Cl | thietanyl S,S-dioxide |
| 320 | Cl | H | Cl | thietanyl S,S-dioxide |
| 321 | Cl | F | Cl | thietanyl S,S-dioxide |
| 322 | Cl | Cl | Cl | cyclopropyl-OH |
| 323 | Cl | H | Cl | cyclopropyl-OH |
| 324 | Cl | F | Cl | cyclopropyl-OH |
| 325 | Cl | Cl | Cl | $CH_2$-pyrazol-1-yl |

TABLE 5-continued

Spirocyclic Dihydropyrazolyls

| Example No. | $R^{1a}$ | $R^{1b}$ | $R^{1c}$ | $R^5$ |
|---|---|---|---|---|
| 326 | Cl | H | Cl | pyrazol-1-ylmethyl |
| 327 | Cl | F | Cl | pyrazol-1-ylmethyl |
| 328 | Cl | Cl | Cl | 1-(trifluoromethyl)cyclopropyl |
| 329 | Cl | H | Cl | 1-(trifluoromethyl)cyclopropyl |
| 330 | Cl | F | Cl | 1-(trifluoromethyl)cyclopropyl |
| 331 | Cl | Cl | Cl | (3-methyl-1H-pyrazol-1-yl)methyl |
| 332 | Cl | H | Cl | (3-methyl-1H-pyrazol-1-yl)methyl |
| 333 | Cl | F | Cl | (3-methyl-1H-pyrazol-1-yl)methyl |
| 334 | Cl | Cl | Cl | 2,2-difluorocyclopropyl |
| 335 | Cl | H | Cl | 2,2-difluorocyclopropyl |
| 336 | Cl | F | Cl | 2,2-difluorocyclopropyl |
| 337 | Cl | Cl | Cl | (pyridin-2-yl)methyl |
| 338 | Cl | H | Cl | (pyridin-2-yl)methyl |
| 339 | Cl | F | Cl | (pyridin-2-yl)methyl |

By the methods described herein, the following spirocyclic dioxazolyls of Table 6 (Examples 340-399) can be prepared from Formula (5.2A).

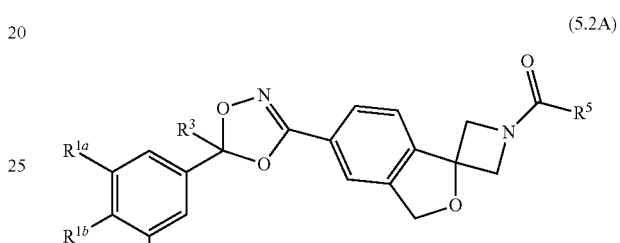

(5.2A)

For Table 6: $R^3$ is trifluoromethyl.

TABLE 6

Spirocyclic Dioxazolyls

| Example No. | $R^{1a}$ | $R^{1b}$ | $R^{1c}$ | $R^5$ |
|---|---|---|---|---|
| 340 | Cl | Cl | Cl | Methyl |
| 341 | Cl | H | Cl | Methyl |
| 342 | Cl | F | Cl | Methyl |
| 343 | Cl | Cl | Cl | Ethyl |
| 344 | Cl | H | Cl | Ethyl |
| 345 | Cl | F | Cl | Ethyl |
| 346 | Cl | Cl | Cl | Propyl |
| 347 | Cl | H | Cl | Propyl |
| 348 | Cl | F | Cl | Propyl |
| 349 | Cl | Cl | Cl | Isobutyl |
| 350 | Cl | H | Cl | Isobutyl |
| 351 | Cl | F | Cl | Isobutyl |
| 352 | Cl | Cl | Cl | $CH_2OH$ |
| 353 | Cl | H | Cl | $CH_2OH$ |
| 354 | Cl | F | Cl | $CH_2OH$ |
| 355 | Cl | Cl | Cl | Cyclopropyl |
| 356 | Cl | H | Cl | Cyclopropyl |
| 357 | Cl | F | Cl | Cyclopropyl |
| 358 | Cl | Cl | Cl | Cyclobutyl |
| 359 | Cl | H | Cl | Cyclobutyl |
| 360 | Cl | F | Cl | Cyclobutyl |
| 361 | Cl | Cl | Cl | $CH_2$—cyclopropyl |
| 362 | Cl | H | Cl | $CH_2$—cyclopropyl |
| 363 | Cl | F | Cl | $CH_2$—cyclopropyl |
| 364 | Cl | Cl | Cl | $CH_2$—cyclobutyl |
| 365 | Cl | H | Cl | $CH_2$—cyclobutyl |
| 366 | Cl | F | Cl | $CH_2$—cyclobutyl |
| 367 | Cl | Cl | Cl | $CH_2CF_3$ |
| 368 | Cl | H | Cl | $CH_2CF_3$ |
| 369 | Cl | F | Cl | $CH_2CF_3$ |
| 370 | Cl | Cl | Cl | —$CH_2SCH_3$ |
| 371 | Cl | H | Cl | —$CH_2SCH_3$ |
| 372 | Cl | F | Cl | —$CH_2SCH_3$ |

TABLE 6-continued

Spirocyclic Dioxazolyls

| Example No. | R¹ᵃ | R¹ᵇ | R¹ᶜ | R⁵ |
|---|---|---|---|---|
| 373 | Cl | Cl | Cl | thietane |
| 374 | Cl | H | Cl | thietane |
| 375 | Cl | F | Cl | thietane |
| 376 | Cl | Cl | Cl | thietane S=O |
| 377 | Cl | H | Cl | thietane S=O |
| 378 | Cl | F | Cl | thietane S=O |
| 379 | Cl | Cl | Cl | thietane SO₂ |
| 380 | Cl | H | Cl | thietane SO₂ |
| 381 | Cl | F | Cl | thietane SO₂ |
| 382 | Cl | Cl | Cl | cyclopropyl-OH |
| 383 | Cl | H | Cl | cyclopropyl-OH |
| 384 | Cl | F | Cl | cyclopropyl-OH |
| 385 | Cl | Cl | Cl | CH₂-pyrazol-1-yl |
| 386 | Cl | H | Cl | CH₂-pyrazol-1-yl |
| 387 | Cl | F | Cl | CH₂-pyrazol-1-yl |
| 388 | Cl | Cl | Cl | 1-CF₃-cyclopropyl |
| 389 | Cl | H | Cl | 1-CF₃-cyclopropyl |
| 390 | Cl | F | Cl | 1-CF₃-cyclopropyl |
| 391 | Cl | Cl | Cl | CH₂-(3-methylpyrazol-1-yl) |
| 392 | Cl | H | Cl | CH₂-(3-methylpyrazol-1-yl) |
| 393 | Cl | F | Cl | CH₂-(3-methylpyrazol-1-yl) |
| 394 | Cl | Cl | Cl | 2,2-difluorocyclopropyl |
| 395 | Cl | H | Cl | 2,2-difluorocyclopropyl |
| 396 | Cl | F | Cl | 2,2-difluorocyclopropyl |
| 397 | Cl | Cl | Cl | CH₂-(pyridin-2-yl) |
| 398 | Cl | H | Cl | CH₂-(pyridin-2-yl) |

TABLE 6-continued

Spirocyclic Dioxazolyls

| Example No. | $R^{1a}$ | $R^{1b}$ | $R^{1c}$ | $R^5$ |
|---|---|---|---|---|
| 399 | Cl | F | Cl | ![pyridinylmethyl] |

By the methods described herein, the following spirocyclic dihydrooxazolyls of Table 7 (Examples 400-68) can be prepared from Formula (4.2A).

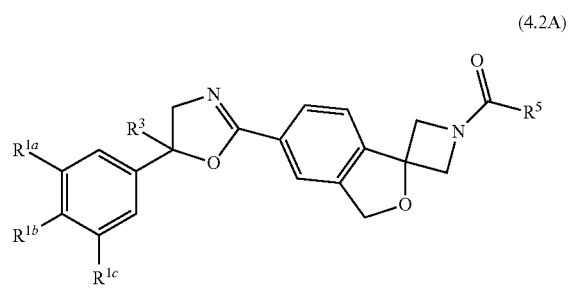

(4.2A)

For Table 7: $R^3$ is trifluoromethyl.

TABLE 7

Spirocyclic Dihydrooxazolyls

| Example No. | $R^{1a}$ | $R^{1b}$ | $R^{1c}$ | $R^5$ |
|---|---|---|---|---|
| 400 | Cl | Cl | Cl | Methyl |
| 401 | Cl | H | Cl | Methyl |
| 402 | Cl | F | Cl | Methyl |
| 403 | Cl | Cl | Cl | Ethyl |
| 404 | Cl | H | Cl | Ethyl |
| 405 | Cl | F | Cl | Ethyl |
| 406 | Cl | Cl | Cl | Propyl |
| 407 | Cl | H | Cl | Propyl |
| 408 | Cl | F | Cl | Propyl |
| 409 | Cl | Cl | Cl | Isopropyl |
| 410 | Cl | H | Cl | Isopropyl |
| 411 | Cl | F | Cl | Isopropyl |
| 412 | Cl | Cl | Cl | Isobutyl |
| 413 | Cl | H | Cl | Isobutyl |
| 414 | Cl | F | Cl | Isobutyl |
| 415 | Cl | Cl | Cl | $CH_2OH$ |
| 416 | Cl | H | Cl | $CH_2OH$ |
| 417 | Cl | F | Cl | $CH_2OH$ |
| 418 | Cl | Cl | Cl | Cyclopropyl |
| 419 | Cl | H | Cl | Cyclopropyl |
| 420 | Cl | F | Cl | Cyclopropyl |
| 421 | Cl | Cl | Cl | Cyclobutyl |
| 422 | Cl | H | Cl | Cyclobutyl |
| 423 | Cl | F | Cl | Cyclobutyl |
| 424 | Cl | Cl | Cl | $CH_2$—cyclopropyl |
| 425 | Cl | H | Cl | $CH_2$—cyclopropyl |
| 426 | Cl | F | Cl | $CH_2$—cyclopropyl |
| 427 | Cl | Cl | Cl | $CH_2$—cyclobutyl |
| 428 | Cl | H | Cl | $CH_2$—cyclobutyl |
| 429 | Cl | F | Cl | $CH_2$—cyclobutyl |
| 430 | Cl | Cl | Cl | $CH_2CF_3$ |
| 431 | Cl | H | Cl | $CH_2CF_3$ |
| 432 | Cl | F | Cl | $CH_2CF_3$ |
| 433 | Cl | Cl | Cl | —$CH_2SCH_3$ |
| 434 | Cl | H | Cl | —$CH_2SCH_3$ |
| 435 | Cl | F | Cl | —$CH_2SCH_3$ |
| 436 | Cl | Cl | Cl | —$CH_2S(O)CH_3$ |
| 437 | Cl | H | Cl | —$CH_2S(O)CH_3$ |
| 438 | Cl | F | Cl | —$CH_2S(O)CH_3$ |
| 439 | Cl | Cl | Cl | —$CH_2S(O)_2CH_3$ |
| 440 | Cl | H | Cl | —$CH_2S(O)_2CH_3$ |
| 441 | Cl | F | Cl | —$CH_2S(O)_2CH_3$ |
| 442 | Cl | Cl | Cl | thietanyl |
| 443 | Cl | H | Cl | thietanyl |
| 444 | Cl | F | Cl | thietanyl |
| 445 | Cl | Cl | Cl | thietanyl S-oxide |
| 446 | Cl | H | Cl | thietanyl S-oxide |
| 447 | Cl | F | Cl | thietanyl S-oxide |
| 448 | Cl | Cl | Cl | thietanyl S,S-dioxide |
| 449 | Cl | H | Cl | thietanyl S,S-dioxide |
| 450 | Cl | F | Cl | thietanyl S,S-dioxide |
| 451 | Cl | Cl | Cl | cyclopropyl-OH |
| 452 | Cl | H | Cl | cyclopropyl-OH |
| 453 | Cl | F | Cl | cyclopropyl-OH |

TABLE 7-continued

Spirocyclic Dihydrooxazolyls

| Example No. | $R^{1a}$ | $R^{1b}$ | $R^{1c}$ | $R^5$ |
|---|---|---|---|---|
| 454 | Cl | Cl | Cl | 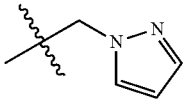 [SMILES: *Cn1cccn1] |
| 455 | Cl | H | Cl | 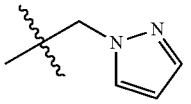 [SMILES: *Cn1cccn1] |
| 456 | Cl | F | Cl | 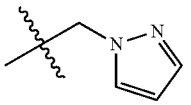 [SMILES: *Cn1cccn1] |
| 457 | Cl | Cl | Cl | 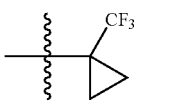 [SMILES: *C1(C(F)(F)F)CC1] |
| 458 | Cl | H | Cl | 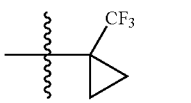 [SMILES: *C1(C(F)(F)F)CC1] |
| 459 | Cl | F | Cl | 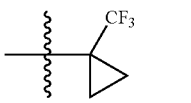 [SMILES: *C1(C(F)(F)F)CC1] |
| 460 | Cl | Cl | Cl | 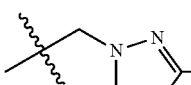 |
| 461 | Cl | H | Cl | 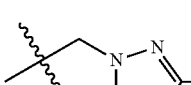 |
| 462 | Cl | F | Cl | 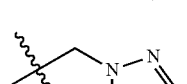 |
| 463 | Cl | Cl | Cl |  |
| 464 | Cl | H | Cl |  |
| 465 | Cl | F | Cl | 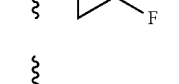 |
| 466 | Cl | Cl | Cl | 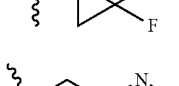 |
| 467 | Cl | H | Cl | 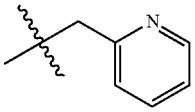 [SMILES: *Cc1ccccn1] |
| 468 | Cl | F | Cl | 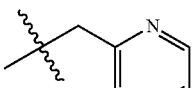 |

Biological Assays

The biological activity of the compounds of the present invention were tested against soft ticks, fleas, and mosquito larvae using the test methods described below.

Flea (*Ctenocephalides felis*) Membrane Feed Assay-Adult

Compounds were dissolved in DMSO and aliquots were added to citrated bovine blood in membrane covered wells warmed to 37° C. Adult fleas were newly emerged (3-7 days) and unfed. Feeding wells containing approximately 10 adult fleas were placed onto the treated blood wells, and the fleas were allowed to feed on the treated blood for 24 hours. Fleas were observed for knockdown and/or death at 24 hours. Each compound was tested at half-log intervals, and endpoint data was recorded as Minimum Effective Concentration in μM. MEC is a subjective visual assessment of organism viability, and is the lowest dose to cause mortality ≥50%. In this assay, Examples 2-4 had an MEC of 0.1 μM; Examples 1 and 5 had an MEC of 0.3 μM; Examples 6 and 16 had an MEC of 1 μM; and Examples 13-15, 17-32 had an MEC of ≥3 μM.

Soft Tick (*Ornithidorus turicata*) Blood Feed Assay

Compounds of the present invention were dissolved in dimethylsulfoxide (DMSO) and aliquots added to citrated bovine blood in a membrane covered Petri dish. The Petri dish is placed on a warming tray. Approximately 5 nymph stage ticks are placed onto the membrane, covered, and left to feed. Fed ticks are removed and placed into a Petri dish with sand. Fed ticks were observed at approximately 24, 48 and 72 hours for paralysis and/or death. Endpoint data was recorded as a 100% lethal dose ($LD^{100}$) in μg/mL. In this assay, Examples 2-5 and 21 had an $LD^{100}$ of 0.01 μg/mL; Examples 1, 6, 13, 15, 16, and 22 had an $LD^{100}$ of 0.03 μg/mL; Examples 14, 17-20, 26, and 28 had an $LD^{100}$ of 0.1 μg/mL; Examples 23-25, 30, and 31 had an $LD^{100}$ of 0.3 μg/mL; and Examples 27 and 29 had an $LD^{100}$ of ≥0.3 μg/mL.

Mosquito (*Aedes aeqypti*) Larval Assay

Compounds were dissolved in DMSO and aliquots were spotted to empty wells. First instar mosquito larvae and maintenance media were added to the wells to obtain between 8 and 15 larvae per well in the appropriate final assay volume. Larvae were incubated in the treated media at 25° C. for 24 hours. Mosquito larvae motility was measured at 24 hours. Each compound was tested at half-log intervals, and endpoint results were recorded as Minimum Effective Concentration (MEC) in μM. MEC is an objective assessment of organism motility, and is the lowest dose to inhibit motility ≥50% of untreated controls. In this assay, Examples 3 and 5 had an MEC of 0.03 μM; Examples 1, 2, 4, 6, 13, 19, and 20 had an MEC of 0.1 μM; Examples 14-17, 28, and 31 had an MEC of 0.3 μM; and Examples 7-12, 22-27, 29, and 32 had an MEC of >3 μM.

We claim:

1. A compound of Formula (V.1) or Formula (V.2)

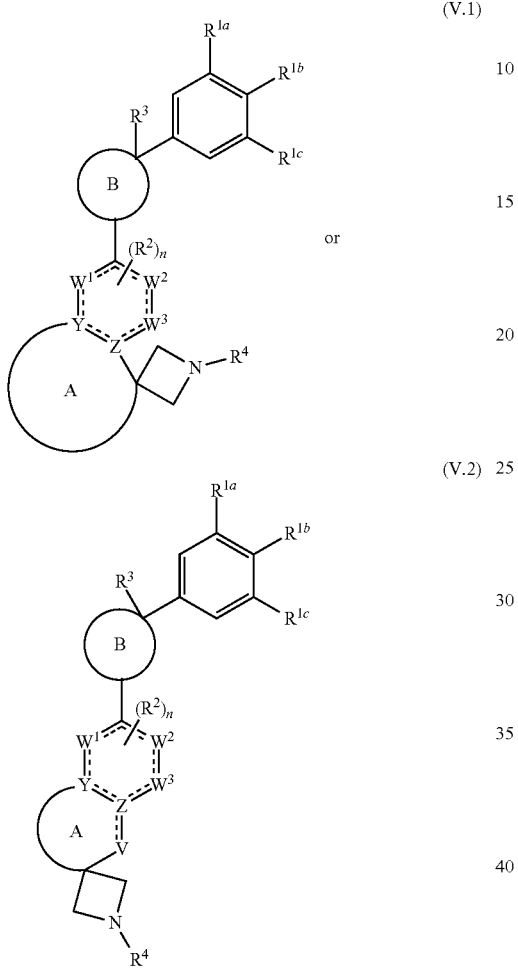

wherein
Y and Z are each independently C or N;
$W^1$, $W^2$, and $W^3$ are each independently C or N;
V is C, N, O, or S;
A taken together with Y and Z or V, Y, and Z is a 5- to 7-membered partially saturated or saturated carbocyclic or heterocyclic ring where the heterocyclic ring contains at least 1 to 3 heteroatoms selected from N, O, or S, and where ring A is optionally substituted with at least one substituent selected from oxo, =S, =NR$^7$, halo, hydroxyl, cyano, $C_1$-$C_6$alkyl, $C_1$-$C_6$haloalkyl, and $C_1$-$C_6$alkoxy;
B is

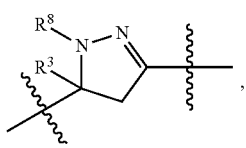

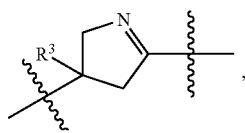

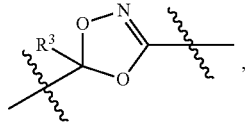

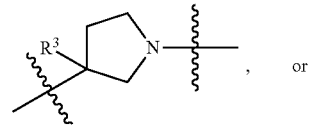

wherein "〜〜" represents the point of attachment;
$R^{1a}$, $R^{1b}$, and $R^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkyl$C_3$-$C_6$ cycloalkyl, $C_1$-$C_6$haloalkoxy, —C(O)NH$_2$, —SF$_5$, or —S(O)$_p$R;
$R^2$ is halo, cyano, $C_1$-$C_6$alkyl, $C_1$-$C_6$haloalkyl, nitro, hydroxyl, —C(O)NR$^a$R$^b$, $C_2$-$C_6$alkenyl, $C_2$-$C_6$alkynyl, —S(O)$_p$R, or —OR;
$R^3$ is cyano, $C_1$-$C_6$alkyl, $C_1$-$C_6$haloalkyl, —C(O)NR$^a$R$^b$, $C_2$-$C_6$alkenyl, $C_2$-$C_6$alkynyl, $C_2$-$C_6$haloalkenyl, or $C_2$-$C_6$haloalkynyl;
$R^4$ is hydrogen, $C_1$-$C_6$alkyl, $C_0$-$C_6$alkyl$C_3$-$C_6$cycloalkyl, —C(O)R$^5$, —C(S)R$^5$, —C(O)NR$^a$R$^5$, —C(O)C(O) NR$^a$R$^5$, —S(O)$_p$R$^c$, —S(O)$_2$NR$^a$R$^5$, —C(NR$^7$)R$^5$, —C(NR$^7$)NR$^a$R$^5$, $C_0$-$C_6$alkylphenyl, $C_0$-$C_6$alkylheteroaryl, or $C_0$-$C_6$alkylheterocycle;
$R^5$ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;
$R^7$ is hydrogen, $C_1$-$C_6$alkyl, hydroxyl, cyano, nitro, —S(O)$_p$R$^c$, or $C_1$-$C_6$alkoxy;
$R^8$ is hydrogen, $C_1$-$C_6$alkyl, hydroxyl, cyano, —S(O)$_p$R$^c$, or $C_1$-$C_6$alkoxy;
R is $C_1$-$C_6$alkyl or $C_3$-$C_6$cycloalkyl optionally substituted with at least one halo substituent;
$R^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;
$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;
$R^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R, —SON, or —C(O)NR$^a$R$^b$;

each of R$^4$ and R$^5$ $C_1$-$C_6$alkyl or $C_0$-$C_6$alkyl$C_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxyl$C_1$-$C_6$alkyl-, —S(O)$_p$R$^c$, —SH, —S(O)$_p$NR$^a$R$^b$, —NR$^a$R$^b$, —NR$^a$C(O)R$^b$, —SC(O)R, —SON, or —C(O)NR$^a$R$^b$; and wherein each of R$^4$ and R$^5$ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =NR$^7$, hydroxyl, $C_1$-$C_6$alkoxy, hydroxyl$C_1$-$C_6$alkyl-, $C_1$-$C_6$alkyl, $C_1$-$C_6$haloalkyl, —SH, —S(O)$_p$R, and $C_1$-$C_6$haloalkoxy;

n is the integer 0, 1, or 2, and when n is 2, each R$^2$ may be identical or different from each other;

p is the integer 0, 1, or 2; and

"----" is a single or double bond;

stereoisomers thereof, and veterinary acceptable salts thereof.

2. A composition comprising a therapeutic amount of a compound of Formula (V.1) or (Formula V.2) of claim 1, and further comprising a veterinary acceptable excipient, diluent, carrier, or mixture thereof.

3. The compound of Formula (V.1) of claim 1 having Formula (V.1.2)

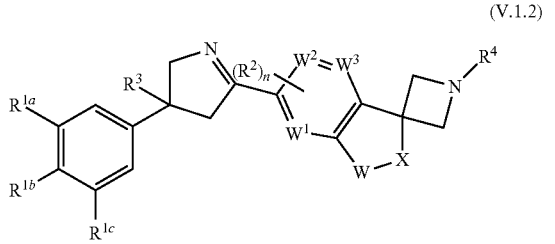

(V.1.2)

wherein X and W are each independently —O—, —S(O)$_p$—, —NR$^6$, —CH$_2$—, —C(O)—, —C(NR$^7$)—, or —C(S)—, and when X is —O—, —S(O)$_p$—, or —NR$^6$, then W is —CH$_2$—, —C(O)—, —C(NR$^7$)—, or —C(S)—, and when W is —O—, —S(O)$_p$—, or —NR$^6$, then X is —CH$_2$—, —C(O)—, —C(NR$^7$)—, or —C(S)—; and R$^6$ is hydrogen, $C_1$-$C_6$alkyl, hydroxyl, or $C_1$-$C_6$alkoxy; stereoisomers thereof, and veterinary acceptable salts thereof.

4. The compound of claim 3 having Formula (2.2)

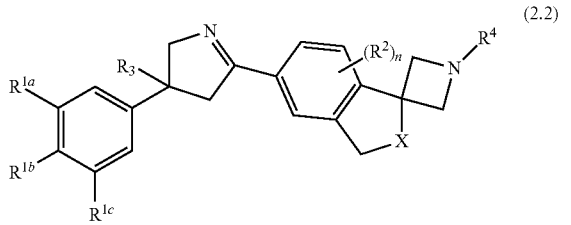

(2.2)

wherein X is —O— or —S(O)$_p$—; stereoisomers thereof, and veterinary acceptable salts thereof.

5. The compound of claim 4 wherein

X is —O—;

n is the integer 0;

R$^{1a}$, R$^{1b}$, and R$^{1c}$ are each independently hydrogen, halo, cyano, $C_1$-$C_6$alkyl, $C_1$-$C_6$haloalkyl, or $C_1$-$C_6$alkoxy;

R$^3$ is $C_1$-$C_6$haloalkyl; and

R$^4$ is —C(O)R$^5$, stereoisomers thereof, and veterinary acceptable salts thereof.

6. The compound of claim 5 wherein R$^{1a}$, R$^{1b}$, and R$^{1c}$ are each independently hydrogen, halo, or $C_1$-$C_6$haloalkyl; and R$^3$ is CF$_3$, stereoisomers thereof, and veterinary acceptable salts thereof.

7. The compound of Formula (V.1) of claim 1 having Formula (V.1.6)

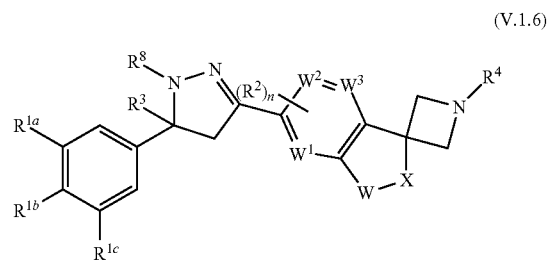

(V.1.6)

wherein X and W are each independently —O—, —S(O)$_p$—, —NR$^6$, —CH$_2$—, —C(O)—, —C(NR$^7$)—, or —C(S)—, and when X is —O—, —S(O)$_p$—, or —NR$^6$, then W is —CH$_2$—, —C(O)—, —C(NR$^7$)—, or —C(S)—, and when W is —O—, —S(O)$_p$—, or —NR$^6$, then X is —CH$_2$—, —C(O)—, —C(NR$^7$)—, or —C(S)—; and R$^6$ is hydrogen, $C_1$-$C_6$alkyl, hydroxyl, or $C_1$-$C_6$alkoxy, stereoisomers thereof, and veterinary acceptable salts thereof.

8. The compound of claim 7 having Formula (6.2)

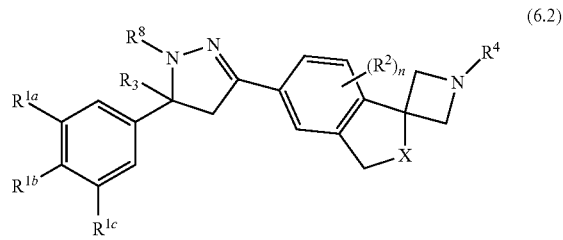

(6.2)

wherein X is —O— or —S(O)$_p$—; stereoisomers thereof, and veterinary acceptable salts thereof.

9. The compound of claim 8 wherein X is —O—;

n is the integer 0;

R$^{1a}$, R$^{1b}$, and R$^{1c}$ are each independently hydrogen, halo, cyano, $C_1$-$C_6$alkyl, $C_1$-$C_6$haloalkyl, or $C_1$-$C_6$alkoxy;

R$^3$ is $C_1$-$C_6$haloalkyl;

R$^4$ is —C(O)R$^5$; and

R$^5$ is hydrogen or $C_1$-$C_6$alkyl, stereoisomers thereof, and veterinary acceptable salts thereof.

10. The compound of Formula (V.1) of claim 1 having Formula (3.2), (4.2), or (5.2)

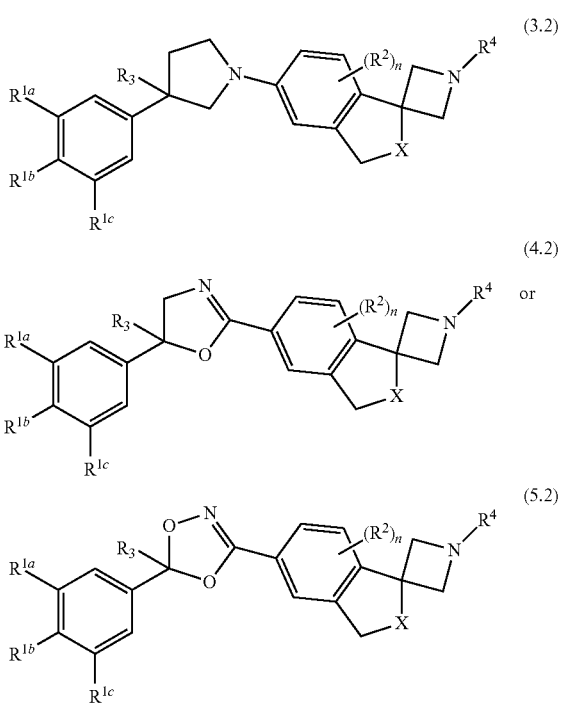

wherein X is —O—;
n is the integer 0;
$R^{1a}$, $R^{1b}$, and $R^{1c}$ are each independently hydrogen, halo, cyano, $C_1$-$C_6$alkyl, $C_1$-$C_6$haloalkyl, or $C_1$-$C_6$alkoxy;
$R^3$ is $C_1$-$C_6$haloalkyl; and
$R^4$ is —C(O)$R^5$, stereoisomers thereof, and veterinary acceptable salts thereof.

11. A compound of claim 1 of Formula (V.1) selected from:
2-(methylsulfonyl)-1-(5'-(3-(3,4,5-trichlorophenyl)-3-(trifluoromethyl)-3,4-dihydro-2H-pyrrol-5-yl)-3'H-spiro[azetidine-3,1'-isobenzofuran]-1-yl)ethanone;
2-methyl-1-(5-(3-(3,4,5-trichlorophenyl)-3-(trifluoromethyl)-3,4-dihydro-2H-pyrrol-5-yl)-3'H-spiro[azetidine-3,1'-isobenzofuran]-1-yl)propan-1-one;
1-(5'-(3-(3,5-dichloro-4-fluorophenyl)-3-(trifluoromethyl)-3,4-dihydro-2H-pyrrol-5-yl)-3'H-spiro[azetidine-3,1'-isobenzofuran]-1-yl)-2-(methylsulfonyl)ethanone;
1-(5'-(3-(3,5-dichloro-4-fluorophenyl)-3-(trifluoromethyl)-3,4-dihydro-2H-pyrrol-5-yl)-3'H-spiro[azetidine-3,1'-isobenzofuran]-1-yl)-2-methylpropan-1-one;
1-(5-(3-(3,5-dichlorophenyl)-3-(trifluoromethyl)-3,4-dihydro-2H-pyrrol-5-yl)-3'H-spiro[azetidine-3,1'-isobenzofuran]-1-yl)-2-(methylsulfonyl)ethanone;
5'-[3-(3,5-dichlorophenyl)-3-(trifluoromethyl)-3,4-dihydro-2H-pyrrol-5-yl]-1-isobutyryl-3'H-spiro[azetidine-3,1'-[2]benzofuran];
1-(5'-(5-(3,5-dichloro-4-fluorophenyl)-5-(trifluoromethyl)-4,5-dihydro-1H-pyrazol-3-yl)-3'H-spiro[azetidine-3,1'-isobenzofuran]-1-yl)-2-(methylsulfonyl)ethanone;
1-(5'-(5-(3,5-dichloro-4-fluorophenyl)-1-methyl-5-(trifluoromethyl)-4,5-dihydro-1H-pyrazol-3-yl)-3'H-spiro[azetidine-3,1'-isobenzofuran]-1-yl)-2-(methylsulfonyl)ethanone;
1-(5'-(5-(3,5-dichloro-4-fluorophenyl)-5-(trifluoromethyl)-4,5-dihydro-1H-pyrazol-3-yl)-3'H-spiro[azetidine-3,1'-isobenzofuran]-1-yl)-2-methylpropan-1-one;
1-(5'-(5-(3,5-dichloro-4-fluorophenyl)-1-methyl-5-(trifluoromethyl)-4,5-dihydro-1H-pyrazol-3-yl)-3'H-spiro[azetidine-3,1'-isobenzofuran]-1-yl)-2-methylpropan-1-one;
1-(5'-(5-(3,4,5-trichlorophenyl)-5-(trifluoromethyl)-4,5-dihydro-1H-pyrazol-3-yl)-3'H-spiro[azetidine-3,1'-isobenzofuran]-1-yl)propan-1-one;
1-(5'-(5-(3,5-dichlorophenyl)-5-(trifluoromethyl)-4,5-dihydro-1H-pyrazol-3-yl)-3'H-spiro[azetidine-3,1'-isobenzofuran]-1-yl)-2-methylpropan-1-one hydrochloride;
2-(methylsulfonyl)-1-(5'-(5-(3,4,5-trichlorophenyl)-5-(trifluoromethyl)-4,5-dihydro-1H-pyrazol-3-yl)-3'H-spiro[azetidine-3,1'-isobenzofuran]-1-yl)ethanone hydrochloride;
1-(5'-(5-(3,5-dichlorophenyl)-5-(trifluoromethyl)-4,5-dihydro-1H-pyrazol-3-yl)-3'H-spiro[azetidine-3,1'-isobenzofuran]-1-yl)methylsulfonylethanone;
5'-[3-(3,5-dichloro-4-fluorophenyl)-3-(trifluoromethyl)pyrrolidin-1yl]-1-isobutyryl-3'H-spiro[azetidine-3,1'-[2]benzofuran;
1-(5'-(3-(3,5-dichloro-4-fluorophenyl)-3-(trifluoromethyl)pyrrolidin-1-yl)-3'H-spiro[azetidine-3,1'-isobenzofuran]-1-yl)-2-(methylsulfonyl)ethanone;
5'-[3-(3,5-dichlorophenyl)-3-(trifluoromethyl)pyrrolidine-1-yl]-1-[(methylsulfonyl)acetyl]-3'H-spiro[azitidine-3,1'-[2]benzofuran];
5'-[3-(3,5-dichlorophenyl)-3-(trifluoromethyl)pyrrolidin-1yl]-1-isobutyryl-3'H-spiro[azetidine-3,1'-[2]benzofuran;
1-isobutyryl-5'-[3-(3,4,5-trichlorophenyl)-3-(trifluoromethyl)pyrrolidin-1yl]-3'H-spiro[azetidine-3,1'-[2]benzofuran;
5'-[3-(3,4,5-trichloro)-3-(trifluoromethyl)pyrrolidin-1-yl]-1-[(methylsulfonyl)acetyl]-3'H-spiro[azetidine-3, 1'-[2]benzofuran];
1-(5'-(5-(3,5-dichloro-4-fluorophenyl)-5-(trifluoromethyl)-1,4,2-dioxazol-3-yl)-3'H-spiro[azetidine-3,1'-isobenzofuran]-1-yl)-2-(methylsulfonyl)ethanone;
1-(5'-(5-(3,5-dichloro-4-fluorophenyl)-5-(trifluoromethyl)-1,4,2-dioxazol-3-yl)-3'H-spiro[azetidine-3,1'-isobenzofuran]-1-yl)-2-methylpropan-1-one;
1-(5'-(5-(3,5-dichlorophenyl)-5-(trifluoromethyl)-1,4,2-dioxazol-3-yl)-3'H-spiro[azetidine-3,1'-isobenzofuran]-1-yl)-2-(methylsulfonyl)ethanone;
1-(5'-(5-(3,5-dichlorophenyl)-5-(trifluoromethyl)-1,4,2-dioxazol-3-yl)-3'H-spiro[azetidine-3,1'-isobenzofuran]-1-yl)-2-methylpropan-1-one;
1-(5'-(5-(3,4,5-trichlorophenyl)-5-(trifluoromethyl)-1,4,2-dioxazol-3-yl)-3'H-spiro[azetidine-3,1'-isobenzofuran]-1-yl)propan-1-one; and
2-(methylsulfonyl)-1-(5'-(5-(3,4,5-trichlorophenyl)-5-(trifluoro methyl)-1,4,2-dioxazol-3-yl)-3'H-spiro[azetidine-3,1'-isobenzofuran]-1-yl)ethanone, stereoisomers thereof, and veterinary acceptable salts thereof.

12. A composition comprising a compound of Formula (V.1.2), (V.1.3), (V.1.4), (V.1.5), or Formula (V.1.6)

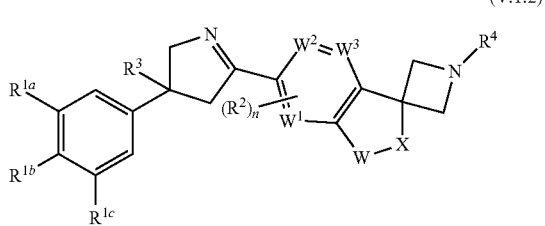
(V.1.2)

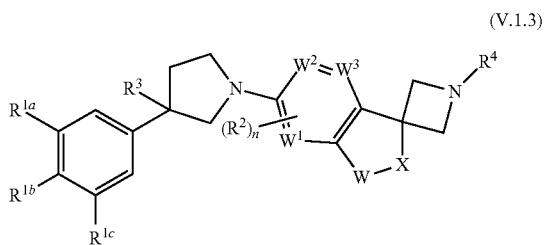
(V.1.3)

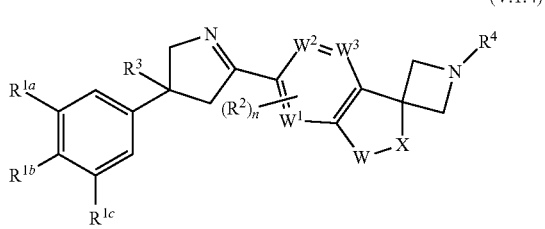
(V.1.4)

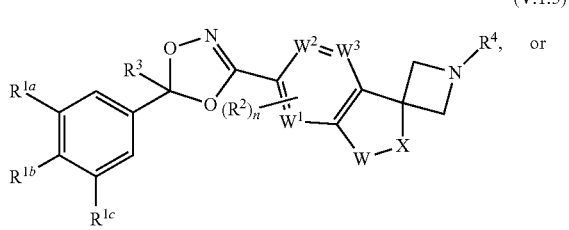
(V.1.5)

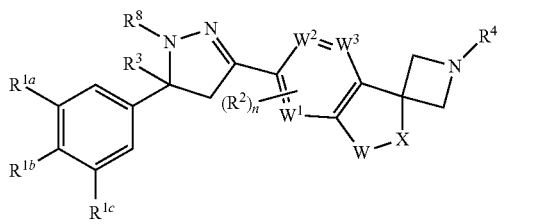
(V.1.6)

wherein

X is —O— and W is —CH$_2$—;

$W^1$, $W^2$, and $W^3$ are each independently C or N;

$R^{1a}$, $R^{1b}$, and $R^{1c}$ are each independently hydrogen, halo, hydroxyl, cyano, nitro, C$_1$-C$_6$alkyl, C$_1$-C$_6$haloalkyl, C$_1$-C$_6$alkoxy, C$_0$-C$_3$alkylC$_3$-C$_6$ cycloalkyl, C$_1$-C$_6$haloalkoxy, —C(O)NH$_2$, —SF$_5$, or —S(O)$_p$R;

$R^2$ is halo, cyano, C$_1$-C$_6$alkyl, C$_1$-C$_6$haloalkyl, nitro, hydroxyl, —C(O)NR$^a$R$^b$, C$_2$-C$_6$alkenyl, C$_2$-C$_6$alkynyl, —S(O)$_p$R, or —OR;

$R^3$ is cyano, C$_1$-C$_6$alkyl, C$_1$-C$_6$haloalkyl, —C(O)NR$^a$R$^b$, C$_2$-C$_6$alkenyl, C$_2$-C$_6$alkynyl, C$_2$-C$_6$haloalkenyl, or C$_2$-C$_6$haloalkynyl;

$R^4$ is hydrogen, C$_1$-C$_6$alkyl, C$_0$-C$_6$alkylC$_3$-C$_6$cycloalkyl, —C(O)R$^5$, —C(S)R$^5$, —C(O)NR$^a$R$^5$, —C(O)C(O)NR$^a$R$^5$, —S(O)$_p$R$^c$, —S(O)$_2$NR$^a$R$^5$, —C(NR$^7$)R$^5$, —C(NR$^7$)NR$^a$R$^5$, C$_0$-C$_6$alkylphenyl, C$_0$-C$_6$alkylheteroaryl, or C$_0$-C$_6$alkylheterocycle;

$R^5$ is hydrogen, C$_1$-C$_6$alkyl, C$_2$-C$_6$alkenyl, C$_0$-C$_6$alkylC$_3$-C$_6$cycloalkyl, C$_0$-C$_6$alkylphenyl, C$_0$-C$_6$alkylheteroaryl, or C$_0$-C$_6$alkylheterocycle;

$R^7$ is hydrogen, C$_1$-C$_6$alkyl, hydroxyl, cyano, nitro, —S(O)$_p$R$^c$, or C$_1$-C$_6$alkoxy;

$R^8$ is hydrogen, C$_1$-C$_6$alkyl, hydroxyl, cyano, —S(O)$_p$R$^c$, or C$_1$-C$_6$alkoxy;

R is C$_1$-C$_6$alkyl or C$_3$-C$_6$cycloalkyl optionally substituted with at least one halo substituent;

$R^a$ is hydrogen, C$_1$-C$_6$alkyl, or C$_0$-C$_3$alkylC$_3$-C$_6$cycloalkyl; wherein the alkyl and alkylcycloalkyl is optionally substituted by cyano or at least one halo substituent;

$R^b$ is hydrogen, C$_1$-C$_6$alkyl, C$_3$-C$_6$cycloalkyl, C$_0$-C$_3$alkylphenyl, C$_0$-C$_3$alkylheteroaryl, or C$_0$-C$_3$alkylheterocycle, each optionally substituted, where chemically possible, with at least one substituent selected from hydroxyl, cyano, halo, or —S(O)$_p$R;

$R^c$ is C$_1$-C$_6$alkyl, C$_1$-C$_6$haloalkyl, C$_1$-C$_6$haloalkylC$_3$-C$_6$cycloalkyl, C$_0$-C$_3$alkylC$_3$-C$_6$cycloalkyl, C$_0$-C$_3$alkylphenyl, C$_0$-C$_3$alkylheteroaryl, or C$_0$-C$_3$alkylheterocycle each optionally substituted with at least one substituent selected from cyano, halo, hydroxyl, oxo, C$_1$-C$_6$alkoxy, C$_1$-C$_6$haloalkoxy, C$_1$-C$_6$haloalkyl, —S(O)$_p$R, —SH, —S(O)$_p$NR$^a$R$^b$, —NR$^a$R$^b$, —NR$^a$C(O)R$^b$, —SC(O)R, —SON, or —C(O)NR$^a$R$^b$;

each of $R^4$ and $R^5$ C$_1$-C$_6$alkyl or C$_0$-C$_6$alkylC$_3$-C$_6$cycloalkyl moiety can be optionally and independently substituted by at least one substituent selected from cyano, halo, hydroxyl, oxo, C$_1$-C$_6$alkoxy, C$_1$-C$_6$haloalkoxy, C$_1$-C$_6$haloalkyl, C$_1$-C$_6$alkyl, hydroxylC$_1$-C$_6$alkyl-, —S(O)$_p$R$^c$, —SH, —S(O)$_p$NR$^a$R$^b$, —NR$^a$R$^b$, —NR$^a$C(O)R$^b$, —SC(O)R, —SON, or —C(O)NR$^a$R$^b$; and wherein each of $R^4$ and $R^5$ C$_0$-C$_6$alkylphenyl, C$_0$-C$_6$alkylheteroaryl, or C$_0$-C$_6$alkylheterocycle moiety can be further optionally substituted with at least one substituent selected from cyano, halo, oxo, =S, =NR$^7$, hydroxyl, C$_1$-C$_6$alkoxy, hydroxylC$_1$-C$_6$alkyl-, C$_1$-C$_6$alkyl, C$_1$-C$_6$haloalkyl, —SH, —S(O)$_p$R, and C$_1$-C$_6$haloalkoxy;

n is the integer 0, 1, or 2, and when n is 2, each $R^2$ may be identical or different from each other; and p is the integer 0, 1, or 2; stereoisomers thereof, and veterinary acceptable salts thereof, and further comprising an acceptable veterinary acceptable excipient, diluent, carrier, or mixture thereof, and optionally, comprising at least one additional veterinary agent.

13. A method of treating a parasitic infection in an animal, comprising administering a therapeutically effective amount of a compound of Formula (V.1) or Formula (V.2)

(V.1)

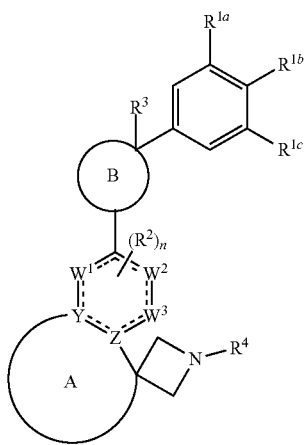

or (V.2)

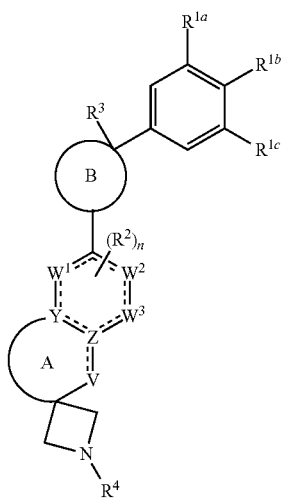

wherein
Y and Z are each independently C or N;
W$^1$, W$^2$, and W$^3$ are each independently C or N;
V is C, N, O, or S;
A taken together with Y and Z or V, Y, and Z is a 5- to 7-membered partially saturated or saturated carbocyclic or heterocyclic ring where the heterocyclic ring contains at least 1 to 3 heteroatoms selected from N, O, or S, and where ring A is optionally substituted with at least one substituent selected from oxo, =S, =NR$^7$, halo, hydroxyl, cyano, C$_1$-C$_6$alkyl, C$_1$-C$_6$haloalkyl, and C$_1$-C$_6$alkoxy;
B is B1
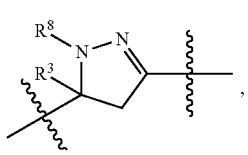, B2
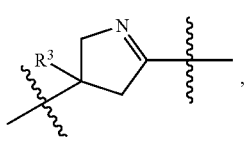, -continued B3
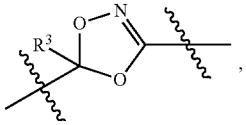, B4
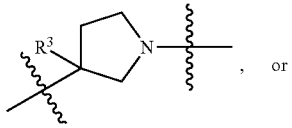, or B5
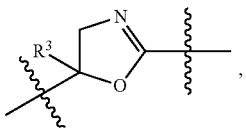, wherein "〰" represents the point of attachment;
R$^{1a}$, R$^{1b}$, and R$^{1c}$ are each independently hydrogen, halo, hydroxyl, cyano, nitro, C$_1$-C$_6$alkyl, C$_1$-C$_6$haloalkyl, C$_1$-C$_6$alkoxy, C$_0$-C$_3$alkylC$_3$-C$_6$ cycloalkyl, C$_1$-C$_6$haloalkoxy, —C(O)NH$_2$, —SF$_5$, or —S(O)$_p$R;
R$^2$ is halo, cyano, C$_1$-C$_6$alkyl, C$_1$-C$_6$haloalkyl, nitro, hydroxyl, —C(O)NR$^a$R$^b$, C$_2$-C$_6$alkenyl, C$_2$-C$_6$alkynyl, —S(O)$_p$R, or —OR;
R$^3$ is cyano, C$_1$-C$_6$alkyl, C$_1$-C$_6$haloalkyl, —C(O)NR$^a$R$^b$, C$_2$-C$_6$alkenyl, C$_2$-C$_6$alkynyl, C$_2$-C$_6$haloalkenyl, or C$_2$-C$_6$haloalkynyl;
R$^4$ is hydrogen, C$_1$-C$_6$alkyl, C$_0$-C$_6$alkylC$_3$-C$_6$cycloalkyl, —C(O)R$^5$, —C(S)R$^5$, —C(O)NR$^a$R$^5$, —C(O)C(O)NR$^a$R$^5$, —S(O)$_p$R$^c$, —S(O)$_2$NR$^a$R$^5$, —C(NR$^7$)R$^5$, —C(NR$^7$)NR$^a$R$^5$, C$_0$-C$_6$alkylphenyl, C$_0$-C$_6$alkylheteroaryl, or C$_0$-C$_6$alkylheterocycle;
R$^5$ is hydrogen, C$_1$-C$_6$alkyl, C$_2$-C$_6$alkenyl, C$_0$-C$_6$alkylC$_3$-C$_6$cycloalkyl, C$_0$-C$_6$alkylphenyl, C$_0$-C$_6$alkylheteroaryl, or C$_0$-C$_6$alkylheterocycle;
R$^7$ is hydrogen, C$_1$-C$_6$alkyl, hydroxyl, cyano, nitro, —S(O)$_p$R$^c$, or C$_1$-C$_6$alkoxy;
R$^8$ is hydrogen, C$_1$-C$_6$alkyl, hydroxyl, cyano, —S(O)$_p$R$^c$, or C$_1$-C$_6$alkoxy;
R is C$_1$-C$_6$alkyl or C$_3$-C$_6$cycloalkyl optionally substituted with at least one halo substituent;
R$^a$ is hydrogen, C$_1$-C$_6$alkyl, or C$_0$-C$_3$alkylC$_3$-C$_6$cycloalkyl; wherein the alkyl and alkylcycloalkyl is optionally substituted by cyano or at least one halo substituent;
R$^b$ is hydrogen, C$_1$-C$_6$alkyl, C$_3$-C$_6$cycloalkyl, C$_0$-C$_3$alkylphenyl, C$_0$-C$_3$alkylheteroaryl, or C$_0$-C$_3$alkylheterocycle, each optionally substituted, where chemically possible, with at least one substituent selected from hydroxyl, cyano, halo, or —S(O)$_p$R;
R$^c$ is C$_1$-C$_6$alkyl, C$_1$-C$_6$haloalkyl, C$_1$-C$_6$haloalkylC$_3$-C$_6$cycloalkyl, C$_0$-C$_3$alkylC$_3$-C$_6$cycloalkyl, C$_0$-C$_3$alkylphenyl, C$_0$-C$_3$alkylheteroaryl, or C$_0$-C$_3$alkylheterocycle each optionally substituted with at least one substituent selected from cyano, halo, hydroxyl, oxo, C$_1$-C$_6$alkoxy, C$_1$-C$_6$haloalkoxy, C$_1$-C$_6$haloalkyl, —S(O)$_p$R, —SH, —S(O)$_p$NR$^a$R$^b$, —NR$^a$R$^b$, —NR$^a$C(O)R$^b$, —SC(O)R, —SON, or —C(O)NR$^a$R$^b$;
each of R$^4$ and R$^5$ C$_1$-C$_6$alkyl or C$_0$-C$_6$alkylC$_3$-C$_6$cycloalkyl moiety can be optionally and independently substituted by at least one substituent selected from cyano, halo, hydroxyl, oxo, C$_1$-C$_6$alkoxy, $C_1$-$C_6$haloalkoxy, $C_1$-$C_6$haloalkyl, $C_1$-$C_6$alkyl, hydroxyl$C_1$-$C_6$alkyl-, —S(O)$_p$R$^c$, —SH, —S(O)$_p$N-R$^a$R$^b$, —NR$^a$R$^b$, —NR$^a$C(O)R$^b$, —SC(O)R, —SON, or —C(O)NR$^a$R$^b$; and wherein each of R$^4$ and R$^5$ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =NR$^7$, hydroxyl, $C_1$-$C_6$alkoxy, hydroxyl$C_1$-$C_6$alkyl-, $C_1$-$C_6$alkyl, $C_1$-$C_6$haloalkyl, —SH, —S(O)$_p$R, and $C_1$-$C_6$haloalkoxy;

n is the integer 0, 1, or 2, and when n is 2, each R$^2$ may be identical or different from each other;

p is the integer 0, 1, or 2; and

"----" is a single or double bond;

stereoisomers thereof, and veterinary acceptable salts thereof, to treat a parasitic infection or infestation in an animal.

14. A compound of claim 1 selected from a compound of Formula, (2.2A), (3.2A), (4.2A), (5.2A), or (6.2A), (2.2A)
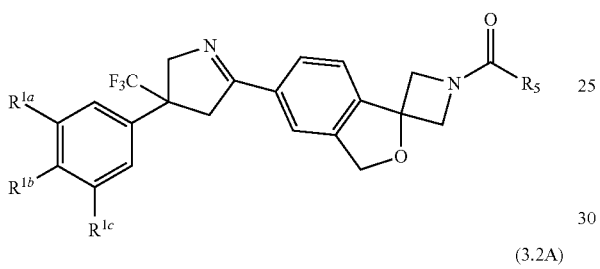

(3.2A)
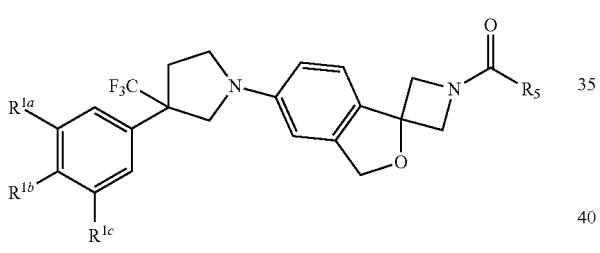

(4.2A)
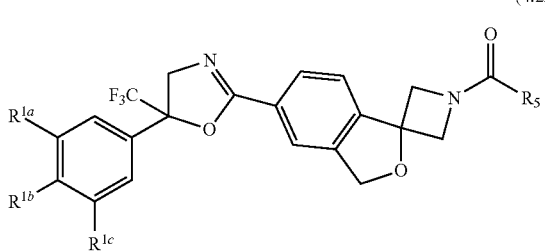

(5.2A)
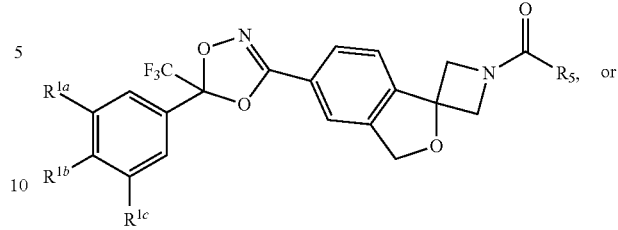

(6.2A)
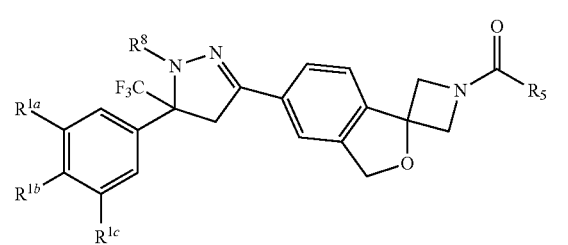

wherein

R$^{1a}$ and R$^{1c}$ are both Cl;

R$^{1b}$ is H, Cl, or F;

R$^5$ is selected from the group consisting of methyl, ethyl, propyl, isobutyl, —CH$_2$cyclopropyl, —CH$_2$cyclobutyl, —CH$_2$cyclopropyl, —CH$_2$cyclobutyl, —CH$_2$CF$_3$, —CH$_2$SCH$_3$, —CH$_2$S(O) CH$_3$, —CH$_2$S(O)$_2$CH$_3$, thietan-3-yl, 1-oxidothietan-3-yl, 1,1-dioxidothietan-3-yl, 1-cyclopropanol-1-yl, 1-trifluoromethylcyclopropan-1-yl, 1H-pyrazol-1-ylmethyl, 3-methyl-1H-pyrazol-1-ylmethyl, 1,1-difluorocycloprop-2-yl, and pyridin-2-ylmethyl;

R$^8$ is H or methyl, and stereoisomers thereof, and veterinary acceptable salts thereof.

15. The method of claim 13 wherein said animal is a companion animal or livestock.

16. The method of claim 15 wherein said companion animal is a cat or dog and wherein said livestock is cattle.

17. The method of claim 13 wherein the therapeutically effective amount of a compound of Formula (V.1) or (V.2) is administered orally, topically, or by injection.

* * * * *